(12) United States Patent
Fink et al.

(10) Patent No.: US 11,427,610 B2
(45) Date of Patent: Aug. 30, 2022

(54) CYCLIC DINUCLEOTIDES AS ANTICANCER AGENTS

(71) Applicant: BRISTOL-MYERS SQUIBB COMPANY, Princeton, NJ (US)

(72) Inventors: Brian E. Fink, Yardley, PA (US); Yufen Zhao, Pennington, NJ (US); Libing Chen, Newtown, PA (US); Audris Huang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 293 days.

(21) Appl. No.: 16/849,091

(22) PCT Filed: Oct. 16, 2018

(86) PCT No.: PCT/US2018/056030
§ 371 (c)(1),
(2) Date: Apr. 15, 2020

(87) PCT Pub. No.: WO2019/079261
PCT Pub. Date: Apr. 25, 2019

(65) Prior Publication Data
US 2021/0253624 A1    Aug. 19, 2021

Related U.S. Application Data

(60) Provisional application No. 62/572,884, filed on Oct. 16, 2017.

(51) Int. Cl.
| | | |
|---|---|---|
| *A01N 43/04* | (2006.01) |
| *A61K 31/70* | (2006.01) |
| *C07H 21/02* | (2006.01) |
| *A61K 45/06* | (2006.01) |
| *C07K 16/28* | (2006.01) |
| *C07H 21/04* | (2006.01) |
| *A61K 39/00* | (2006.01) |

(52) U.S. Cl.
CPC ............ *C07H 21/02* (2013.01); *A61K 45/06* (2013.01); *C07H 21/04* (2013.01); *C07K 16/2818* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2006/0167241 A1* | 7/2006 | Hayakawa | C07H 19/10 536/26.2 |
| 2014/0341976 A1* | 11/2014 | Dubensky, Jr. | A61K 31/7084 424/278.1 |

FOREIGN PATENT DOCUMENTS

WO     2017161349 A1     9/2017

OTHER PUBLICATIONS

Chiba, Junya, et al., "Furanose ring conformations in a 10-alkynyl C-nucleoside and the dinucleotide", Tetrahedron, 2012, vol. 68, pp. 9045-9049.

Siegel, Dustin, et al., "Discovery and Synthesis of a Phosphoramidate Prodrug of a Pyrrolo[2,1-f][triazin-4-amino]Adenine C-Nucleoside (GS-5734) for the Treatment of Ebola and Emerging Viruses", J. Med. Chem. 2017, vol. 60, pp. 1648-1661.

* cited by examiner

*Primary Examiner* — Patrick T Lewis
(74) *Attorney, Agent, or Firm* — Elliott Korsen

(57) ABSTRACT

The present invention is directed to compounds of the formula

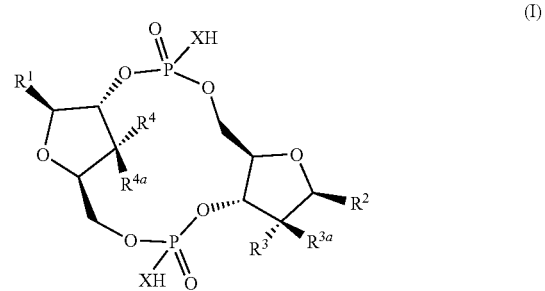

(I)

wherein all substituents are defined herein, as well as pharmaceutically acceptable compositions comprising compounds of the invention and methods of using said compositions in the treatment of various disorders.

23 Claims, No Drawings
Specification includes a Sequence Listing.

SEQUENCE LISTING

```
<160> NUMBER OF SEQ ID NOS: 2

<210> SEQ ID NO 1
<211> LENGTH: 210
<212> TYPE: PRT
<213> ORGANISM: Artificial Sequence
<220> FEATURE:
<223> OTHER INFORMATION: Homosapien

<400> SEQUENCE: 1

Met Gly Ser Ser His His His His His His Ser Ser Gly Glu Thr Val
1               5                   10                  15

Arg Phe Gln Gly His Met Ser Val Ala His Gly Leu Ala Trp Ser Tyr
            20                  25                  30

Tyr Ile Gly Tyr Leu Arg Leu Ile Leu Pro Glu Leu Gln Ala Arg Ile
        35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65                  70                  75                  80

Leu Ser Met Ala Asp Pro Asn Ile Arg Phe Leu Asp Lys Leu Pro Gln
```

```
            85                  90                  95
Gln Thr Gly Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
            115                 120                 125

Glu Tyr Ala Thr Pro Leu Gln Thr Leu Phe Ala Met Ser Gln Tyr Ser
            130                 135                 140

Gln Ala Gly Phe Ser Arg Glu Asp Arg Leu Glu Gln Ala Lys Leu Phe
145                 150                 155                 160

Cys Arg Thr Leu Glu Asp Ile Leu Ala Asp Ala Pro Glu Ser Gln Asn
                165                 170                 175

Asn Cys Arg Leu Ile Ala Tyr Gln Glu Pro Ala Asp Asp Ser Ser Phe
                180                 185                 190

Ser Leu Ser Gln Glu Val Leu Arg His Leu Arg Gln Glu Glu Lys Glu
                195                 200                 205

Glu Val
    210

<210> SEQ ID NO 2
<211> LENGTH: 210
<212> TYPE: PRT
<213> ORGANISM: Artificial Sequence
<220> FEATURE:
<223> OTHER INFORMATION: Homosapien

<400> SEQUENCE: 2

Met Gly Ser Ser His His His His His His Ser Ser Gly Glu Thr Val
1               5                   10                  15

Arg Phe Gln Gly His Met Ser Val Ala His Gly Leu Ala Trp Ser Tyr
            20                  25                  30

Tyr Ile Gly Tyr Leu Arg Leu Ile Leu Pro Glu Leu Gln Ala Arg Ile
            35                  40                  45

Arg Thr Tyr Asn Gln His Tyr Asn Asn Leu Leu Arg Gly Ala Val Ser
        50                  55                  60

Gln Arg Leu Tyr Ile Leu Leu Pro Leu Asp Cys Gly Val Pro Asp Asn
65                  70                  75                  80

Leu Ser Met Ala Asp Pro Asn Ile Arg Phe Leu Asp Lys Leu Pro Gln
                85                  90                  95

Gln Thr Ala Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
            115                 120                 125

Glu Tyr Ala Thr Pro Leu Gln Thr Leu Phe Ala Met Ser Gln Tyr Ser
            130                 135                 140

Gln Ala Gly Phe Ser Arg Glu Asp Arg Leu Glu Gln Ala Lys Leu Phe
145                 150                 155                 160

Cys Gln Thr Leu Glu Asp Ile Leu Ala Asp Ala Pro Glu Ser Gln Asn
                165                 170                 175

Asn Cys Arg Leu Ile Ala Tyr Gln Glu Pro Ala Asp Asp Ser Ser Phe
                180                 185                 190

Ser Leu Ser Gln Glu Val Leu Arg His Leu Arg Gln Glu Glu Lys Glu
                195                 200                 205

Glu Val
    210
```

CYCLIC DINUCLEOTIDES AS ANTICANCER AGENTS

CROSS-REFERENCE TO RELATED APPLICATIONS

This application is a national phase application under 35 U.S.C. § 371 of International Patent Application No. PCT/US2018/056030, filed Oct. 16, 2018, which claims priority to U.S. Provisional Application Ser. No. 62/572,884, filed Oct. 16, 2017, the contents of which are specifically incorporated fully herein by reference.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

Immunotherapy is a rapidly expanding area of medical treatment in which a patient's immune system is deliberately activated, suppressed or otherwise modulated for a positive therapeutic effect. Immunotherapy agents include such things as cells, antigens, antibodies, nucleic acids, proteins, peptides, naturally occurring ligands and synthetically prepared molecules. Cytokines are small glycoprotein molecules known for their role in causing immune response through complex signaling networks. Cytokines have been explored as immunotherapy agents but their direct administration is hampered by many factors including their short half-life in blood which can only be compensated with frequent and often high doses. One highly promising approach is cytokine induction in which the patient is treated with an immunomodulatory agent that triggers the production of one or more therapeutically beneficial cytokines in their body.

One agent in the production of cytokines is the adaptor protein STING (STimulator of INterferon Genes; also known as MPYS, TMEM173, MITA and ERIS). STING is an intracellular receptor situated on the endoplasmic reticulum. The binding to STING by an agonist activates a signaling pathway culminating in the induction of Type I IFNs, which are secreted and protect the secreting and nearby cells. STING can be activated by two different pathways, each involving a different type of cyclic dinucleotide ("CDN") agonist. In the first pathway, the agonist is an exogenous CDN used by bacterial pathogens as a second messenger (Burdette et al. 2013). In the second pathway the enzyme cyclic GMP-AMP synthase (cGAS) detects cytosolic DNA and, in response, synthesizes a CDN that functions as an endogenous STING agonist (Ablasser et al. 2013; Gao et al. 2013; Sun et al. 2013).

Activation of STING results in up-regulation of IRF3 and NF-κB pathways leading to induction of Interferon-β and other cytokines. STING is crucial for responses to cytosolic DNA of pathogen or host origin.

Two exogenous bacterial STING agonist CDNs are 3'3'-cGAMP and c-GMP. The endogenous STING agonist CDN made by cGAS is 2'3'-cGAMP. The bacterial CDNs are characterized by two 3'5' phosphodiester bridges, while the cGAS-produced CDN is characterized by one 2'5' and one 3'5' phosphodiester bridge. As a shorthand, the former CDNs are referred to as 3'3' CDNs and the latter as 2'3' CDNs. For historical reasons, 3'3' CDNs also are referred to as the "canonical" form and 2'3' CDNs are referred to as the "non-canonical" form.

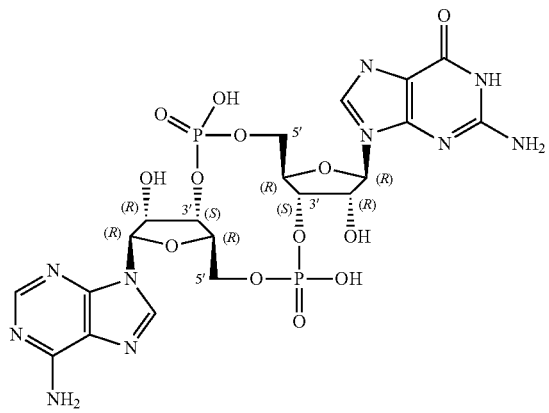

3'3'-cGAMP

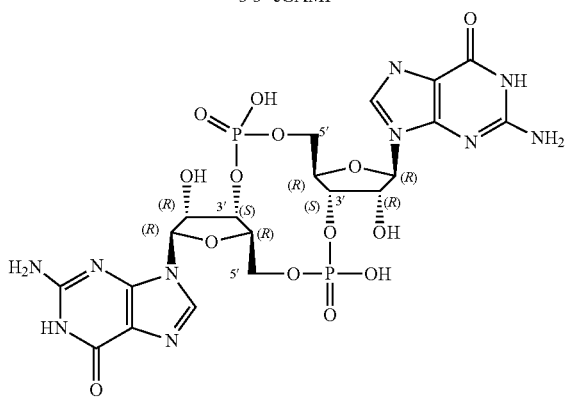

c-di-GMP

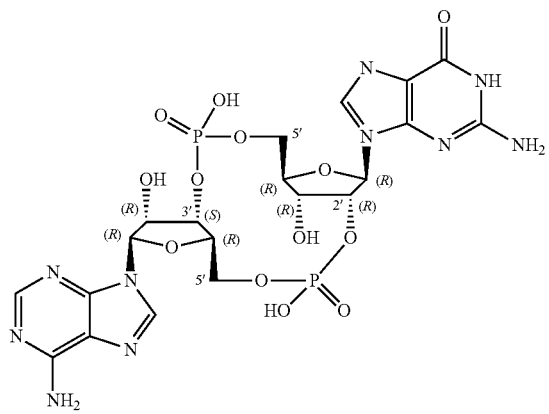

2'3'-cGAMP

In addition to protecting an organism against pathogen infection, STING activation has also been reported to be beneficial in the treatment of inflammatory diseases and, in an area of particular current interest, cancer. Administration of a synthetic CDN in combination with the cancer vaccine STINGVAX demonstrated enhanced antitumor efficacy in multiple therapeutic models (Fu et al. 2015). Administration of STING agonists alone has been reported to show potent antitumor immune efficacy in a mouse model (Corrales et al.

2015a). For reviews on the role of STING in infection, inflammation, and/or cancer, see Ahn et al. 2015; Corrales et al. 2015b and 2016; and Barber 2015.

The present invention, therefore, provides novel cyclic dinucleotides which may be useful for the treatment of cancer.

SUMMARY OF THE INVENTION

There is provided a compound of formula (I)

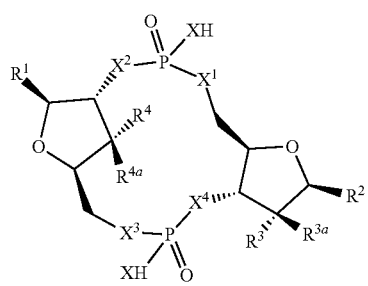

(I)

wherein
each X is independently O or S;
$X^1$, $X^2$, $X^3$ and $X^4$ are each independently O or NH;
$R^1$ and $R^2$ are independently

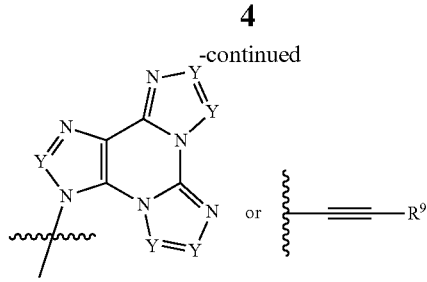

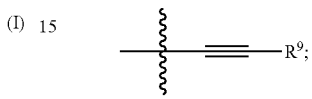

with the proviso that one of $R^1$ and $R^2$ must be $$\text{---}\equiv\text{---}R^9;$$

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;
m is 0, 1, 2 or 3;

or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a method of treating cancer which comprises administering to a subject in need thereof a therapeutically effective amount of an activator of STING (of Formula I).

DETAILED DESCRIPTION OF THE INVENTION

In a first aspect of the invention, there is provided a compound of formula (I)

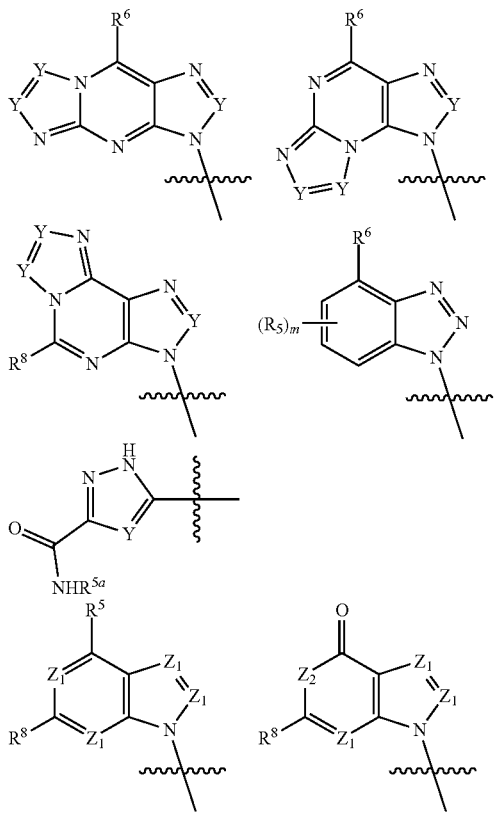

(I)

wherein
each X is independently O or S;
$X^1$, $X^2$, $X^3$ and $X^4$ are each independently O or NH;
$R^1$ and $R^2$ are independently

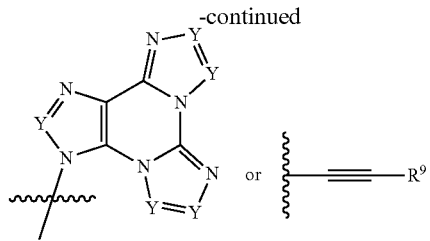

-continued

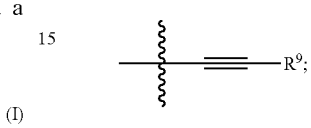

with the proviso that one of $R^1$ and $R^2$ must be

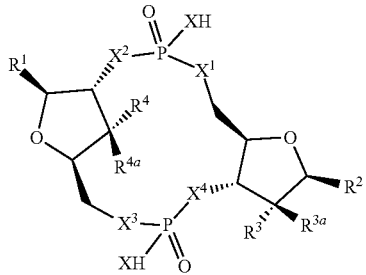

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$.
$R^{a1}$ is H or $C_{1-3}$ alkyl substituted with 0-6 $R^5$;
$R^3$ and $R^4$ are independently H, $CH_3$, halogen, $NH_2$ or OH;
$R^{3a}$ and $R^{4a}$ are independently H, $CH_3$, halogen, $NH_2$ or OH; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a C=$CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;
Y is $CR^5$ or N;
m is 0, 1, 2 or 3;

or a pharmaceutically acceptable salt, tautomer or stereoisomer thereof.
In a second aspect of the invention, there is provided a compound of formula (I) wherein
R¹ is
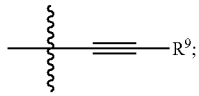
and
R² is
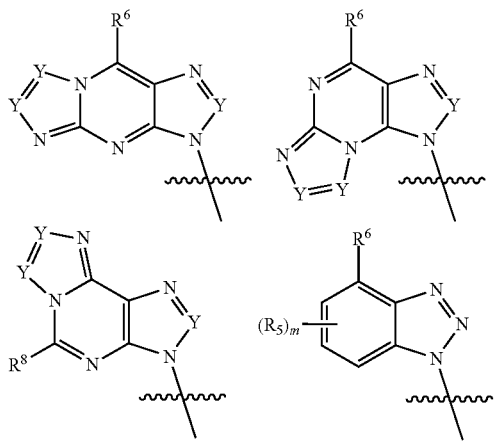
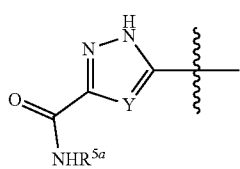
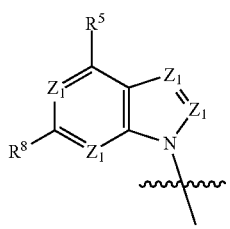 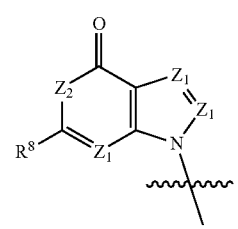
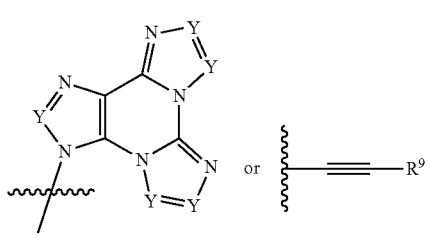
In a third aspect of the invention, there is provided a compound of formula (I) wherein
R¹ is
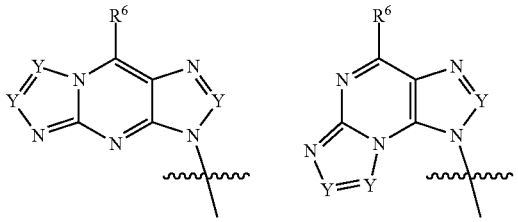
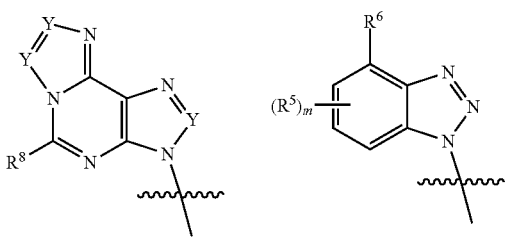
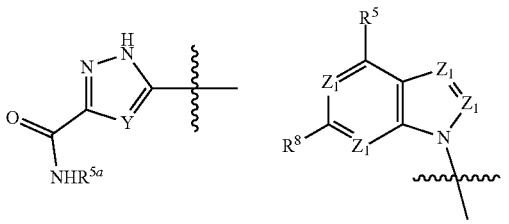
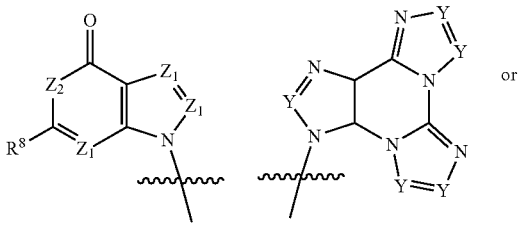
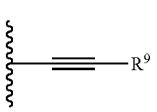
and
R² is
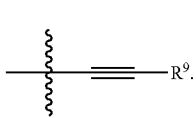
In a 4th aspect of the invention, there is provided a compound of formula (I)

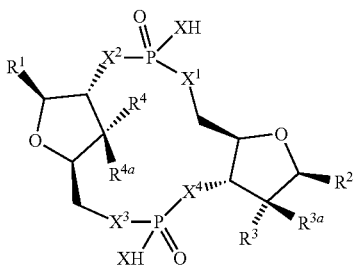

(I)

wherein
each X is independently O or S;
$X^1$, $X^2$, $X^3$ and $X^4$ are each independently O or NH;
$R^1$ and $R^2$ are independently

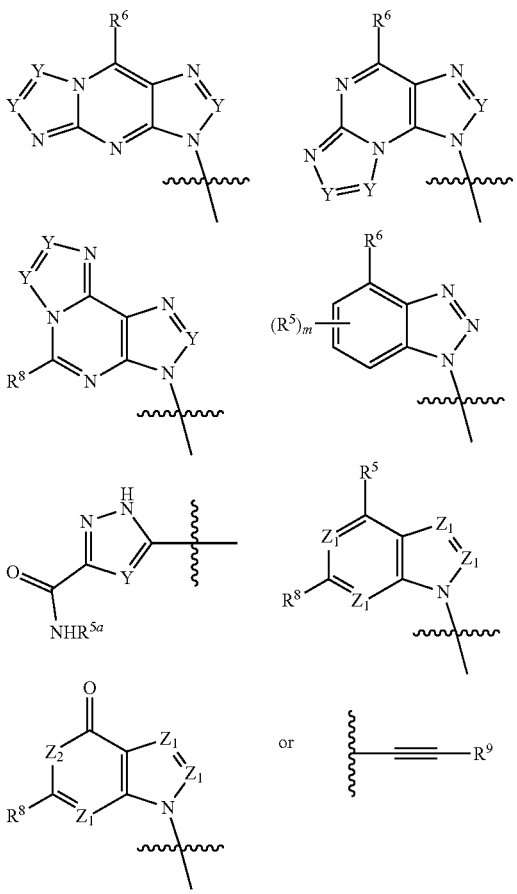

with the proviso that one of $R^1$ and $R^2$ must be

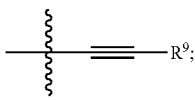

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$; Y is $CR^5$ or N;

or a pharmaceutically acceptable salt, tautomer or stereoisomer thereof.

In a fifth aspect of the invention, there is provided a compound of formula (I)

(I)

wherein
X is S;
$X^1$, $X^2$, $X^3$ and $X^4$ are each independently O or NH;

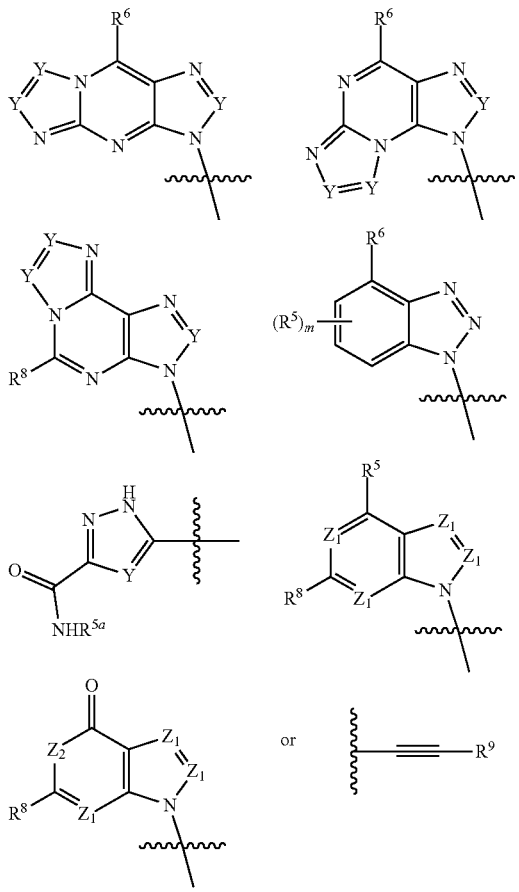

with the proviso that one of $R^1$ and $R^2$ must be

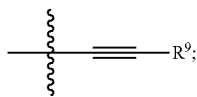

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a sixth aspect of the invention, there is provided a compound of the formula

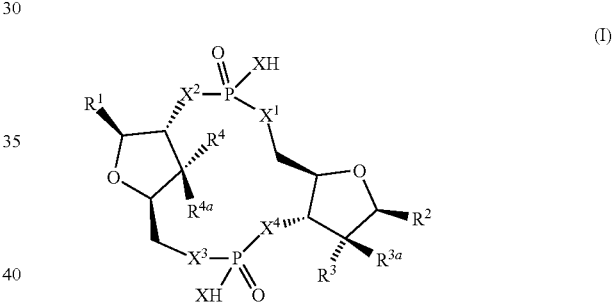

(I)

wherein

X is O;

$X^1$, $X^2$, $X^3$ and $X^4$ are each independently O or NH;

$R^1$ and $R^2$ are independently

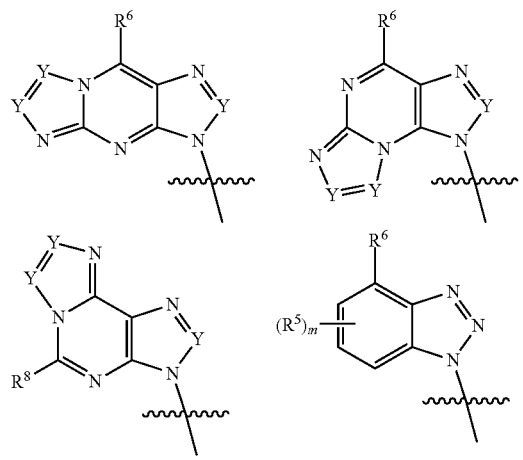

-continued

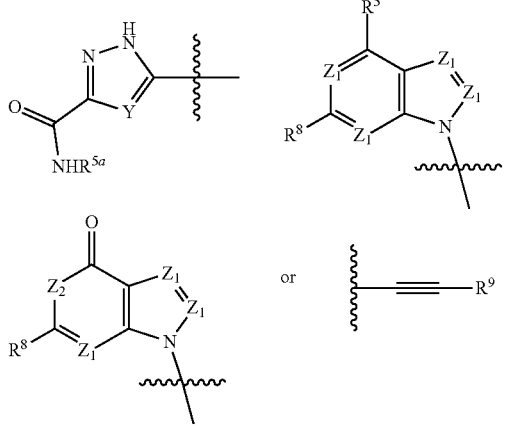

with the proviso that one of $R^1$ and $R^2$ must be

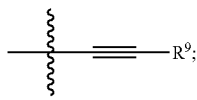

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$.
$R^{a1}$ is H or $C_{1-3}$ alkyl substituted with 0-6 $R^5$;
$R^3$ and $R^4$ are independently H, $CH_3$, halogen, $NH_2$ or OH;
$R^{3a}$ and $R^{4a}$ are independently H, $CH_3$, halogen, $NH_2$ or OH; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a $C=CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a seventh aspect of the invention, there is provided a compound of the formula

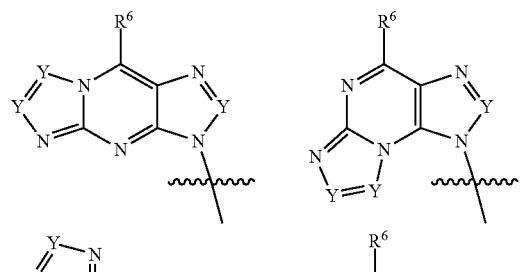

wherein $X^1$, $X^2$, $X^3$ and $X^4$ are each independently O or NH;

$R^1$ and $R^2$ are independently

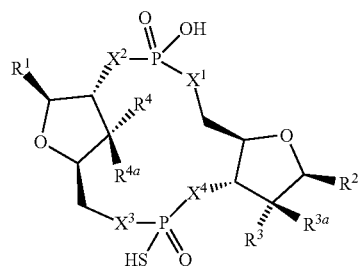

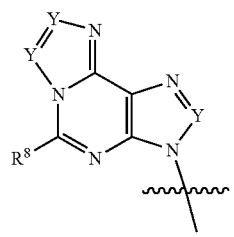

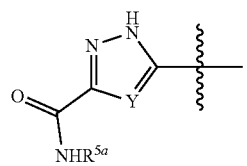

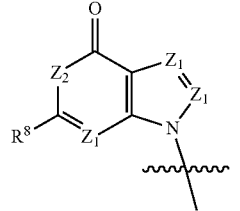

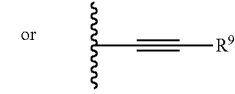

with the proviso that one of $R^1$ and $R^2$ must be

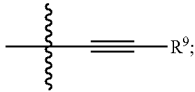

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In an 8th aspect of the invention, there is provided a compound of the formula

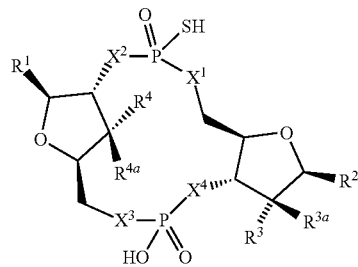

wherein $X^1$, $X^2$, $X^3$ and $X^4$ are each independently O or NH;

$R^1$ and $R^2$ are independently

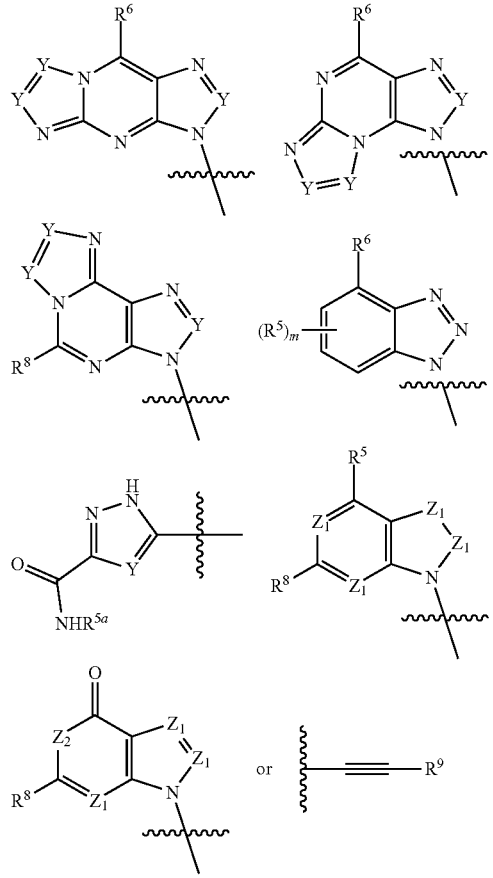

with the proviso that one of $R^1$ and $R^2$ must be

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^4$ are independently H, CH$_3$, halogen, NH$_2$ or OH;

R$^{3a}$ and R$^{4a}$ are independently H, CH$_3$, halogen, NH$_2$ or OH; or

R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, C$_{1-6}$ alkyl substituted with 0-6 R$^5$, C$_{3-6}$ cycloalkyl substituted with 0-6 R$^5$, aryl substituted with 0-6 R$^5$ or heteroaryl substituted with 0-6 R$^5$;

Y is CR$^5$ or N;

or a pharmaceutically acceptable salt, tautomer or stereoisomer thereof.

In a ninth aspect of the invention, there is provided a compound of the formula

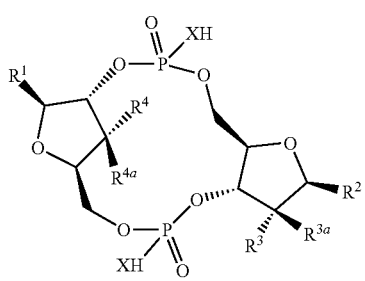

wherein each X is independently O or S;

R$^1$ and R$^2$ are independently

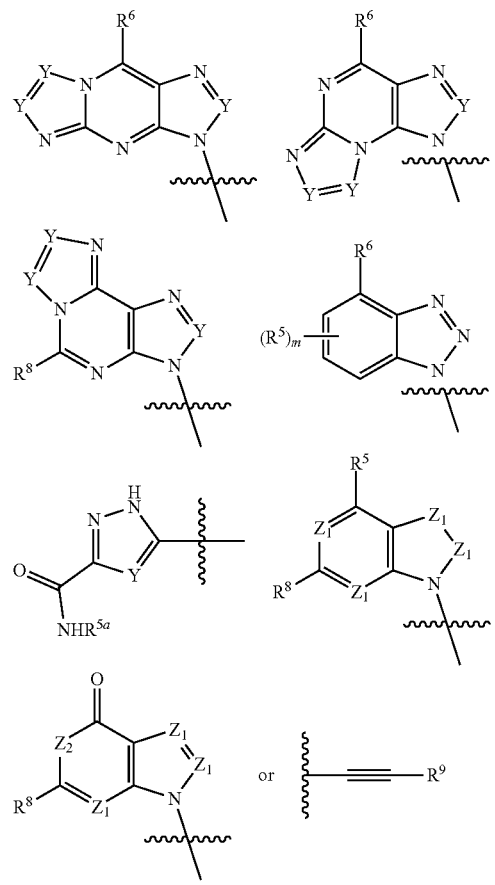

with the proviso that one of R$^1$ and R$^2$ must be

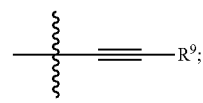

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$.

R$^{a1}$ is H or C$_{1-3}$ alkyl substituted with 0-6 R$^5$;

R$^3$ and R$^4$ are independently H, CH$_3$, halogen, NH$_2$ or OH;

R$^{3a}$ and R$^{4a}$ are independently H, CH$_3$, halogen, NH$_2$ or OH; or

R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6

$R^a$ or heteroaryl substituted with 0-6 $R^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or C$_{1-3}$ alkyl substituted with 0-6 R$^5$;

$R^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^9$ is H, C$_{1-6}$ alkyl substituted with 0-6 R$^5$, C$_{3-6}$ cycloalkyl substituted with 0-6 R$^5$, aryl substituted with 0-6 R$^5$ or heteroaryl substituted with 0-6 R$^5$;

Y is CR$^5$ or N;

or a pharmaceutically acceptable salt, tautomer or stereoisomer thereof.

In a tenth aspect of the invention, there is provided a compound of the formula

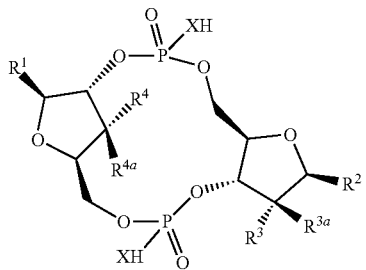

wherein

X is S;

$R^1$ and $R^2$ are independently

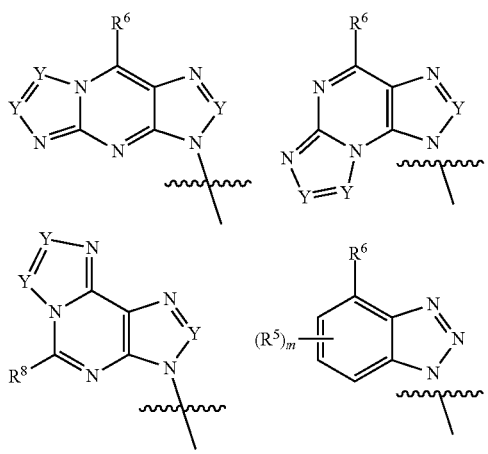

-continued

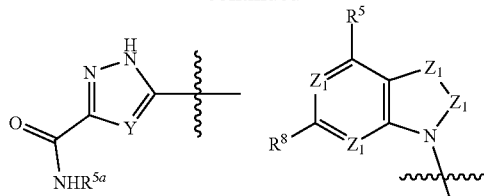

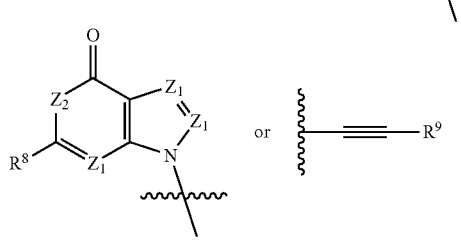

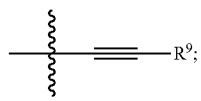

with the proviso that one of $R^1$ and $R^2$ must be

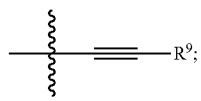

$Z^1$ is N or CR$^a$;

$Z^2$ is NR$^b$;

$R^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H or C$_{1-3}$ alkyl substituted with 0-6 R$^5$;

$R^3$ and $R^4$ are independently H, CH$_3$, halogen, NH$_2$ or OH;

$R^{3a}$ and $R^{4a}$ are independently H, CH$_3$, halogen, NH$_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=CH$_2$ substituent;

$R^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or C$_{1-3}$ alkyl substituted with 0-6 R$^5$;

$R^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, C$_{1-6}$ alkyl substituted with 0-6 R$^5$, C$_{3-6}$ cycloalkyl substituted with 0-6 R$^5$, aryl substituted with 0-6 R$^5$ or heteroaryl substituted with 0-6 R$^5$;

Y is CR$^5$ or N;

or a pharmaceutically acceptable salt, tautomer or stereoisomer thereof.

In an 11th aspect of the invention, there is provided a compound of the formula

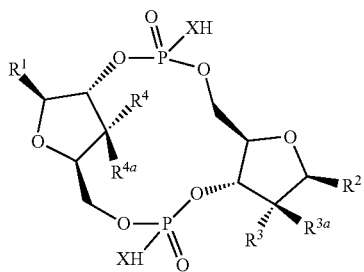

wherein

X is O;

R$^1$ and R$^2$ are independently

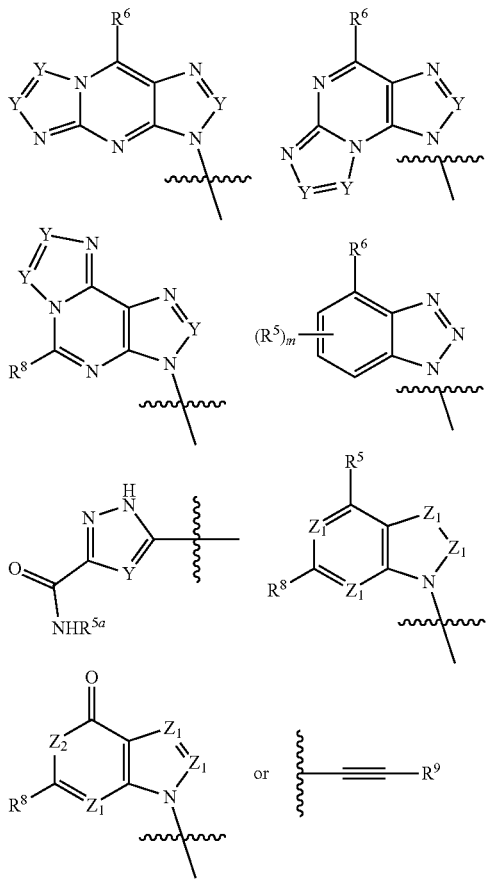

with the proviso that one of R$^1$ and R$^2$ must be

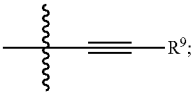

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^4$ are independently H, CH$_3$, halogen, NH$_2$ or OH;

R$^{3a}$ and R$^{4a}$ are independently H, CH$_3$, halogen, NH$_2$ or OH; or

R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, C$_{1-6}$ alkyl substituted with 0-6 R$^5$, C$_{3-6}$ cycloalkyl substituted with 0-6 R$^5$, aryl substituted with 0-6 R$^5$ or heteroaryl substituted with 0-6 R$^5$;

Y is CR$^5$ or N;

or a pharmaceutically acceptable salt, tautomer or stereoisomer thereof.

In a 12$^{th}$ aspect of the invention, there is provided a compound of the formula

23

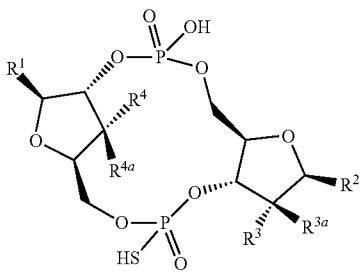

wherein
R¹ and R² are independently

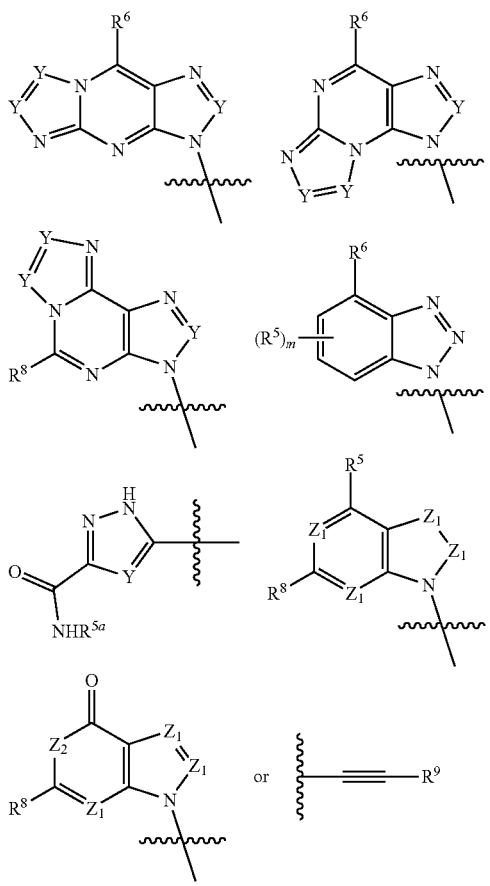

with the proviso that one of R¹ and R² must be

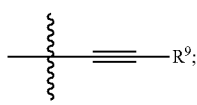

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 13$^{th}$ aspect of the invention, there is provided a compound of the formula

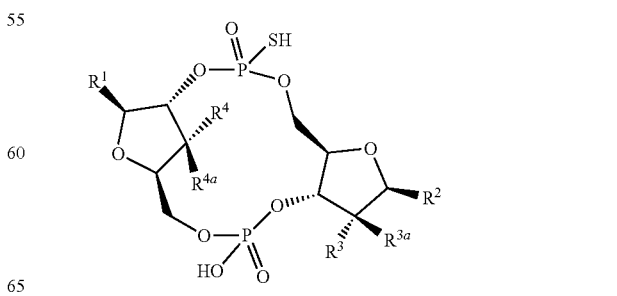

wherein
R¹ and R² are independently

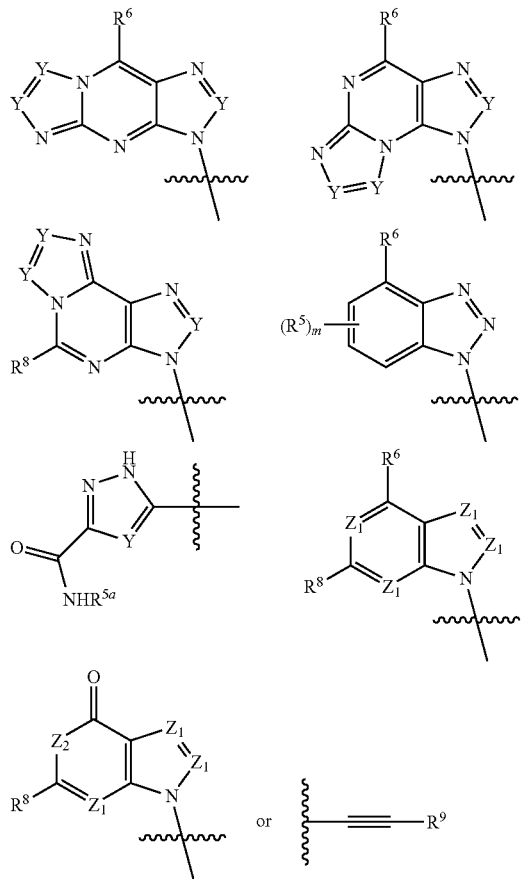

with the proviso that one of R¹ and R² must be

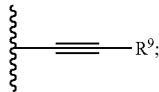

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;
$R^{a1}$ is H or $C_{1-3}$ alkyl substituted with 0-6 $R^5$;
$R^3$ and $R^4$ are independently H, CH$_3$, halogen, NH$_2$ or OH;
$R^{3a}$ and $R^{4a}$ are independently H, CH$_3$, halogen, NH$_2$ or OH; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a C=CH$_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^8$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;
Y is CR$^5$ or N;
or a pharmaceutically acceptable salt, tautomer or stereoisomer thereof.

In a 14$^{th}$ aspect of the invention, there is provided a compound of the formula

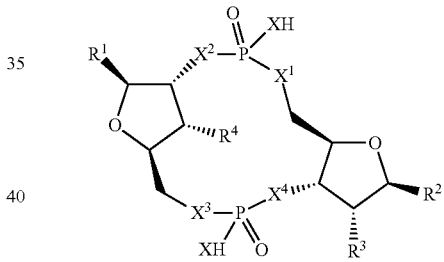

wherein
each X is independently O or S;
X$^1$, X$^2$, X$^3$ and X$^4$ are each independently O or NH;
R$^1$ and R$^2$ are independently

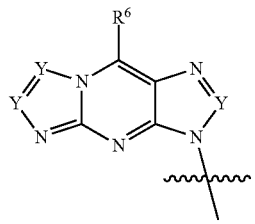 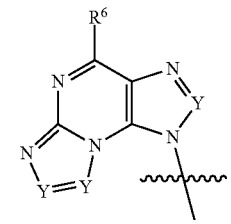

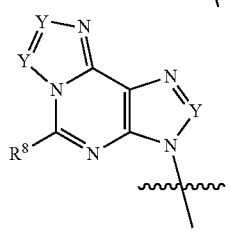 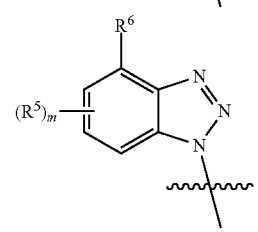

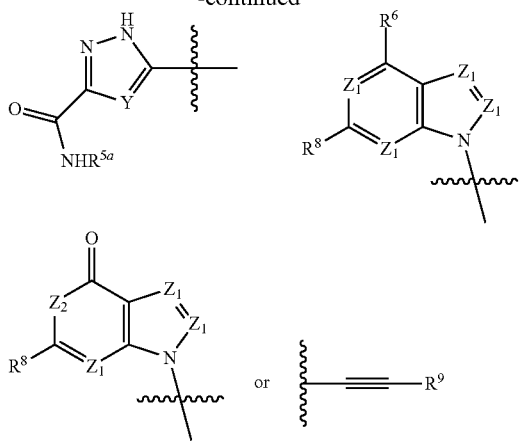

with the proviso that one of $R^1$ and $R^2$ must be

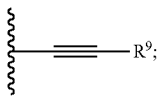

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl substituted with 0-6 $R^5$;
$R^3$ and $R^4$ are independently H, $CH_3$, halogen, $NH_2$ or OH;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;
or a pharmaceutically acceptable salt, tautomer or stereoisomer thereof.

In a 15th aspect of the invention, there is provided a compound of the formula

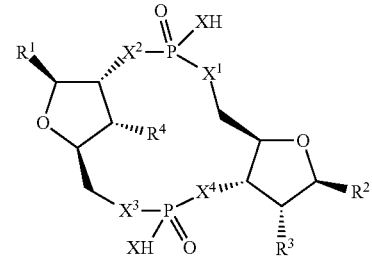

(I)

wherein
X is S;
$X^1$, $X^2$, $X^3$ and $X^4$ are each independently O or NH;
$R^1$ and $R^2$ are independently

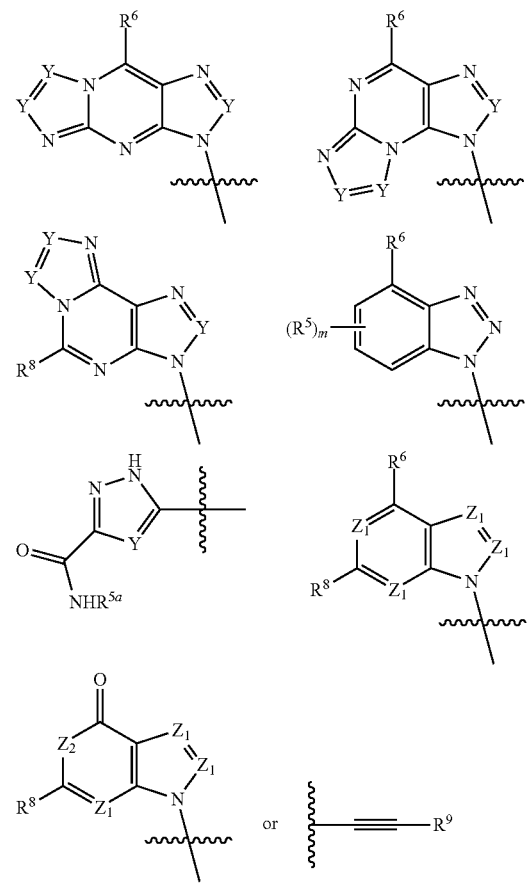

with the proviso that one of $R^1$ and $R^2$ must be

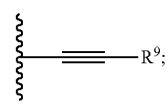

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 16th aspect of the invention, there is provided a compound of the formula

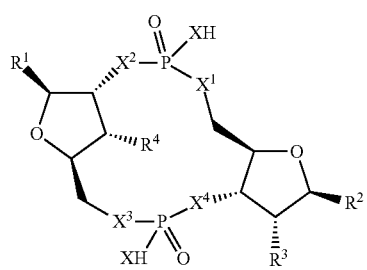

wherein

X is O;

$X^1$, $X^2$, $X^3$ and $X^4$ are each independently O or NH;

$R^1$ and $R^2$ are independently

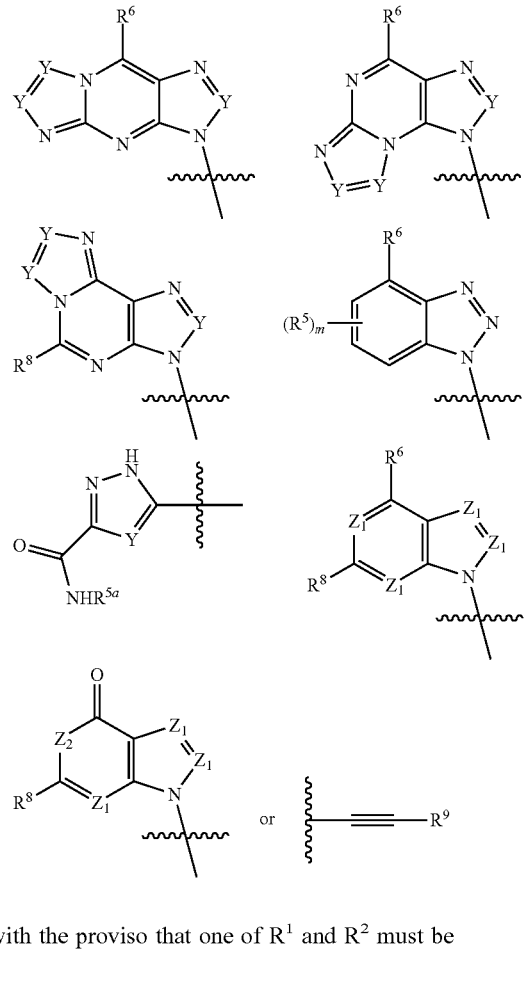

with the proviso that one of $R^1$ and $R^2$ must be

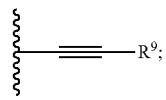

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 17$^{th}$ aspect of the invention, there is provided a compound of the formula

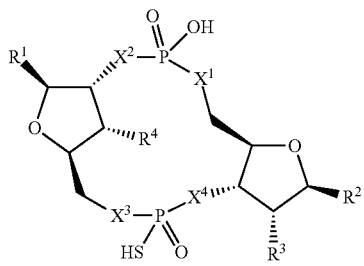

(I)

wherein $X^1$, $X^2$, $X^3$ and $X^4$ are each independently O or NH;

$R^1$ and $R^2$ are independently

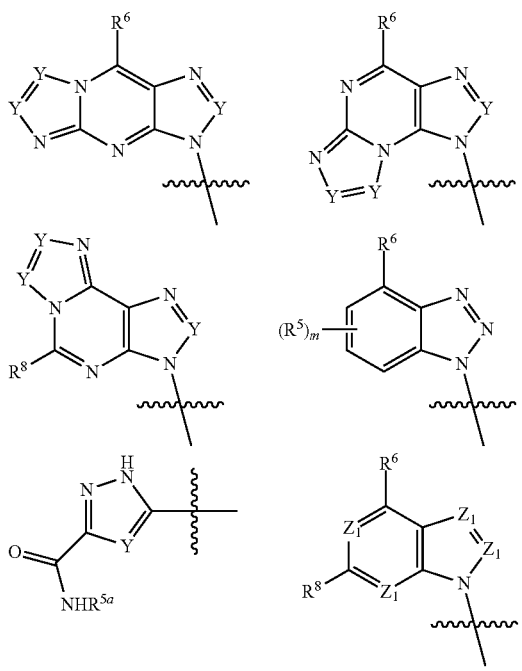

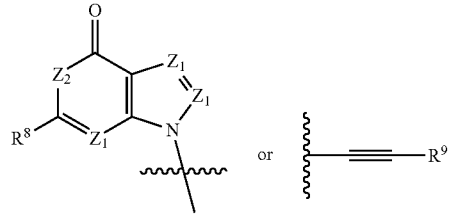

or with the proviso that one of $R^1$ and $R^2$ must be

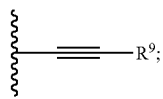

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^5$ is H, halogen, $C_{1-3}$ alkyl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^5$ is H, halogen, $C_{1-3}$ alkyl substituted with 0-6 $R^5$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In an 18$^{th}$ aspect of the invention, there is provided a compound of the formula

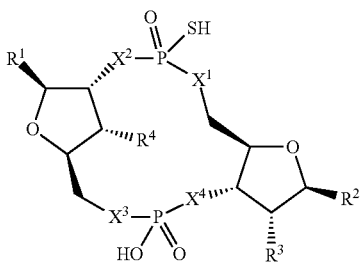

wherein
$X^1$, $X^2$, $X^3$ and $X^4$ are each independently O or NH;
$R^1$ and $R^2$ are independently

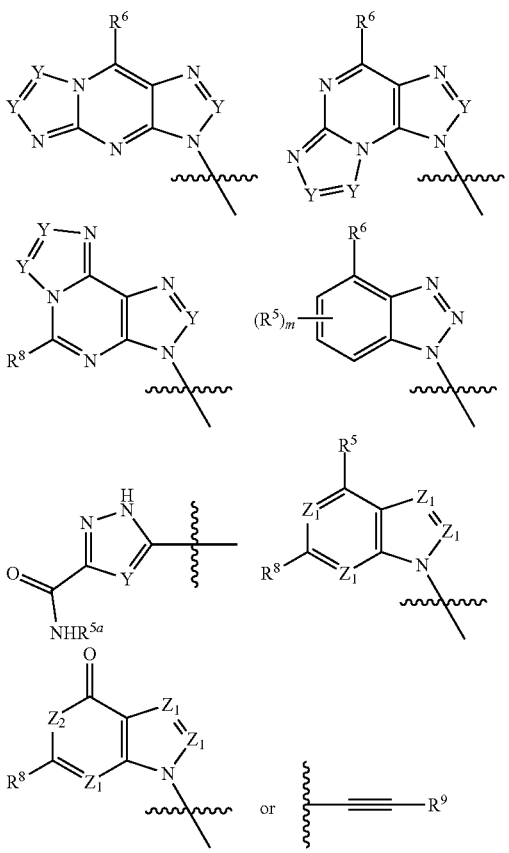

with the proviso that one of $R^1$ and $R^2$ must be

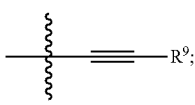

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$.

$R^{a1}$ is H or $C_{1-3}$ alkyl substituted with 0-6 $R^5$;

$R^3$ and $R^4$ are independently H, $CH_3$, halogen, $NH_2$ or OH;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 19th aspect of the invention, there is provided a compound of the formula

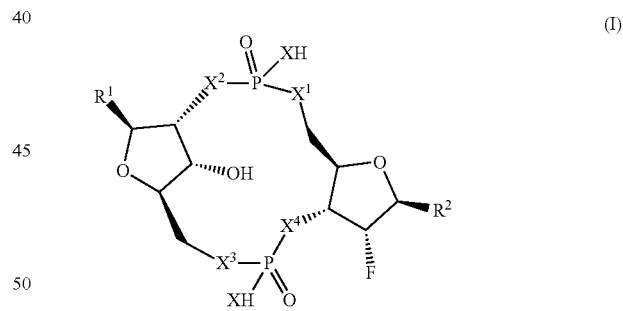

wherein
X is S;
$X^1$, $X^2$, $X^3$ and $X^4$ are each independently O or NH;
$R^1$ and $R^2$ are independently

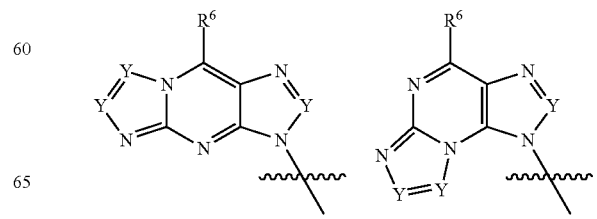

-continued

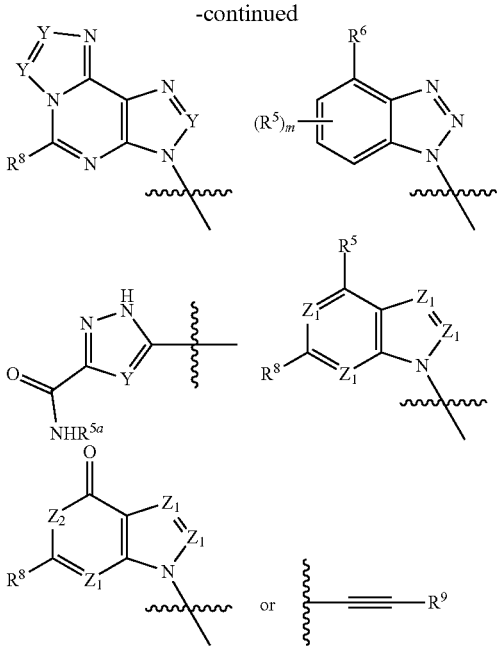

with the proviso that one of $R^1$ and $R^2$ must be

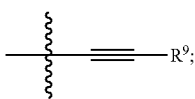

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 20th aspect of the invention, there is provided a compound of the formula

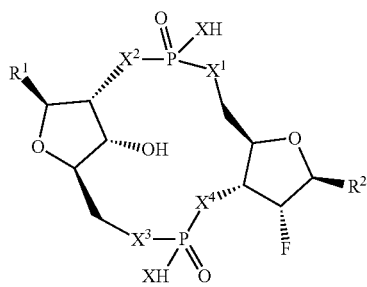

wherein

X is O;

$X^1$, $X^2$, $X^3$ and $X^4$ are each independently O or NH;

$R^1$ and $R^2$ are independently

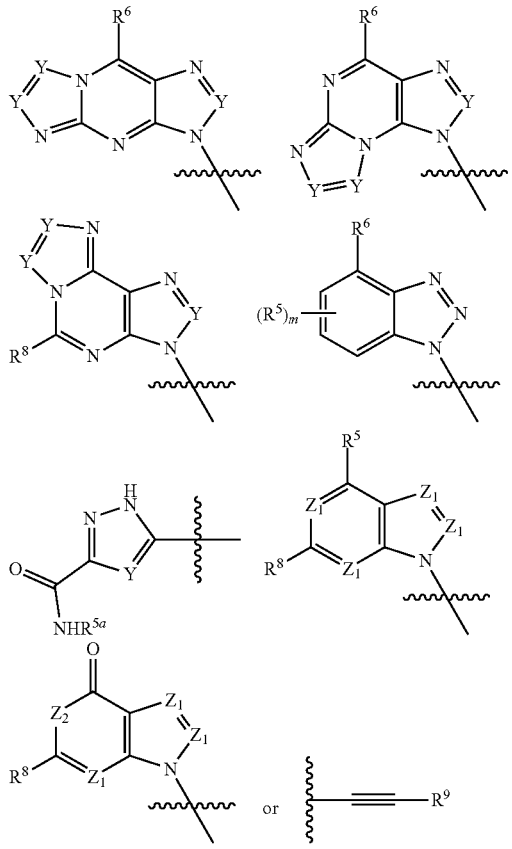

with the proviso that one of R¹ and R² must be

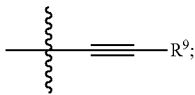

Z¹ is N or CR$^a$;
Z² is NR$^b$;
R$^a$ is H, halogen, $C_{1-6}$ alkyl substituted with 0-6 R⁵, $C_{3-6}$ cycloalkyl substituted with 0-6 R⁵, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R$^b$ is H, $C_{1-6}$ alkyl substituted with 0-6 R⁵, $C_{3-6}$ cycloalkyl substituted with 0-6 R⁵, —C(O)R$^{a1}$, —C(O)NR$^{a1}$R$^{a1}$, —S(O)₂R$^{a1}$ or S(O)₂NR$^{a1}$R$^{a1}$;

R$^{a1}$ is H or $C_{1-3}$ alkyl substituted with 0-6 R⁵;

R⁵ is H, halogen, $C_{1-3}$ alkyl substituted with 0-6 R$^a$, $C_{3-6}$ cycloalkyl substituted with 0-6 R$^a$, aryl substituted with 0-6 R$^a$ or heteroaryl substituted with 0-6 R$^a$, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R$^{5a}$ is H or $C_{1-3}$ alkyl substituted with 0-6 R⁵;

R⁶ is H, halogen, $C_{1-3}$ alkyl substituted with 0-6 R⁵, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R⁸ is H, halogen, $C_{1-3}$ alkyl substituted with 0-6 R⁵, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R⁹ is H, $C_{1-6}$ alkyl substituted with 0-6 R⁵, $C_{3-6}$ cycloalkyl substituted with 0-6 R⁵, aryl substituted with 0-6 R⁵ or heteroaryl substituted with 0-6 R⁵;

Y is CR⁵ or N;

or a pharmaceutically acceptable salt, tautomer or stereoisomer thereof.

In a 21st aspect of the invention, there is provided a compound of the formula

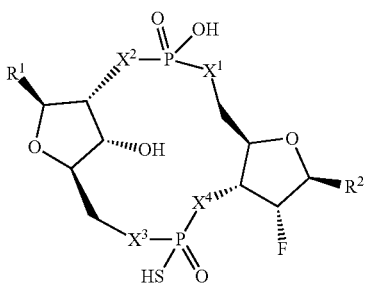

(I)

wherein
X¹, X², X³ and X⁴ are each independently O or NH;

R¹ and R² are independently

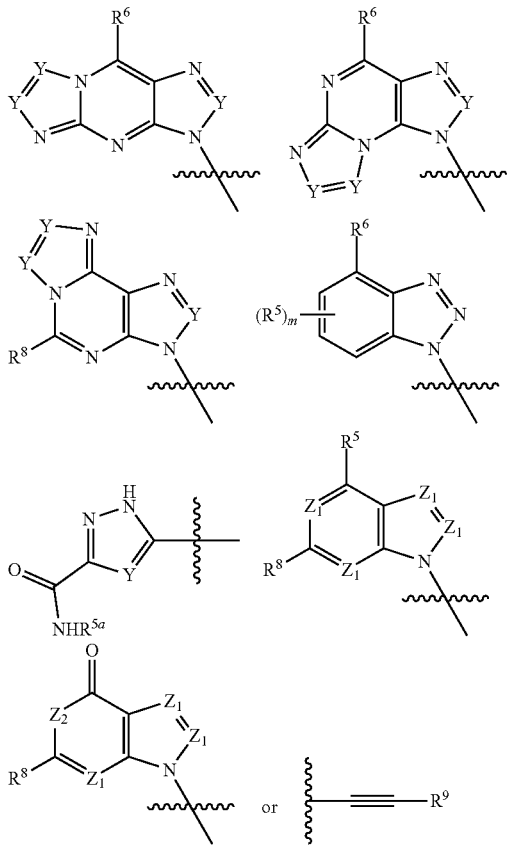

with the proviso that one of R¹ and R² must be

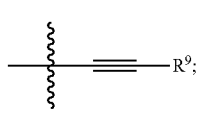

Z¹ is N or CR$^a$;
Z² is NR$^b$;
R$^a$ is H, halogen, $C_{1-6}$ alkyl substituted with 0-6 R⁵, $C_{3-6}$ cycloalkyl substituted with 0-6 R⁵, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R$^b$ is H, $C_{1-6}$ alkyl substituted with 0-6 R⁵, $C_{3-6}$ cycloalkyl substituted with 0-6 R⁵, —C(O)R$^{a1}$, —C(O)NR$^{a1}$R$^{a1}$, —S(O)₂R$^{a1}$ or S(O)₂NR$^{a1}$R$^{a1}$;

R$^{a1}$ is H or $C_{1-3}$ alkyl substituted with 0-6 R⁵;

R⁵ is H, halogen, $C_{1-3}$ alkyl substituted with 0-6 R$^a$, $C_{3-6}$ cycloalkyl substituted with 0-6 R$^a$, aryl substituted with 0-6 R$^a$ or heteroaryl substituted with 0-6 R$^a$, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R$^{5a}$ is H or $C_{1-3}$ alkyl substituted with 0-6 R⁵;

$R^6$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is CR$^5$ or N;

or a pharmaceutically acceptable salt, tautomer or stereoisomer thereof.

In the 22nd aspect of the invention, there is provided a compound of the formula

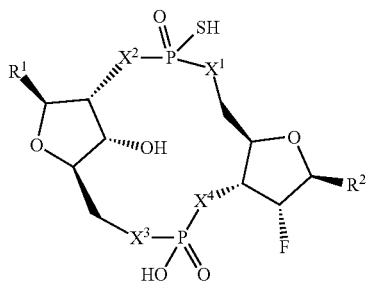

(I)

wherein $X^1$, $X^2$, $X^3$ and $X^4$ are each independently O or NH;

$R^1$ and $R^2$ are independently

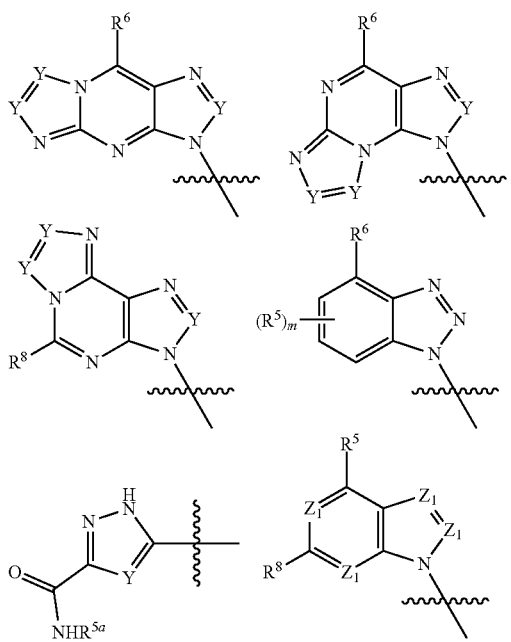

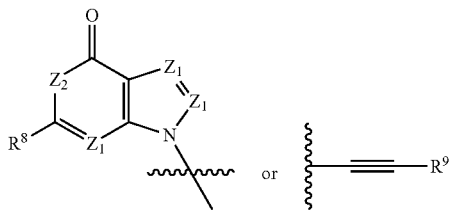

with the proviso that one of $R^1$ and $R^2$ must be

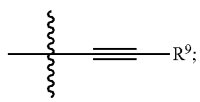

$Z^1$ is N or CR$^a$;

$Z^2$ is NR$^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$.

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is CR$^5$ or N;

or a pharmaceutically acceptable salt, tautomer or stereoisomer thereof.

In the 23rd aspect of the invention, there is provided a compound of the formula

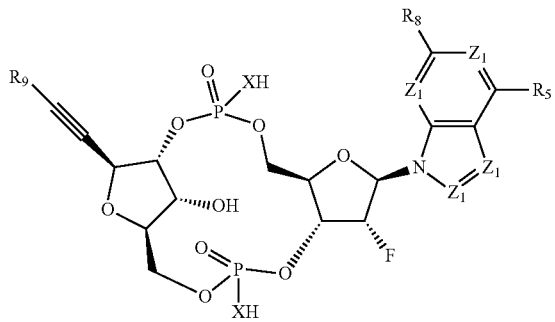

wherein each X is independently O or S;

$Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In the 24th aspect of the invention, there is provided a compound of the formula

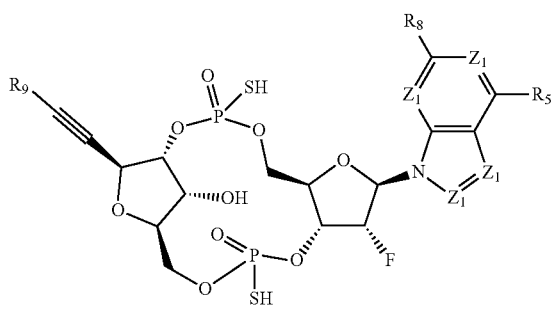

wherein $Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In the 25th aspect of the invention, there is provided a compound of the formula

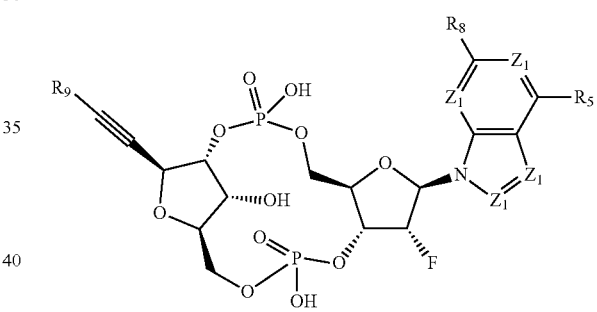

wherein $Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 26th aspect of the invention, there is provided a compound of the formula

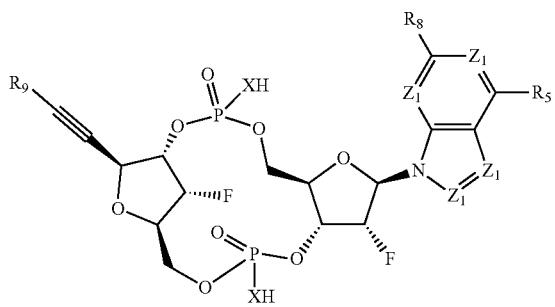

wherein
each X is independently O or S;
$Z^1$ is N or $CR^a$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 27th aspect of the invention, there is provided a compound of the formula

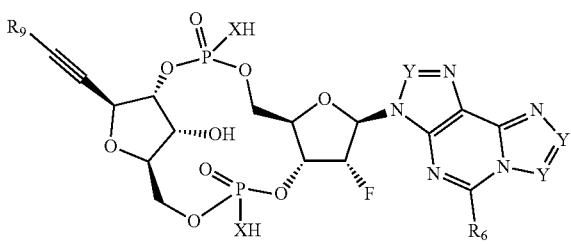

wherein
each X is independently O or S;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 28th aspect of the invention, there is provided a compound of the formula

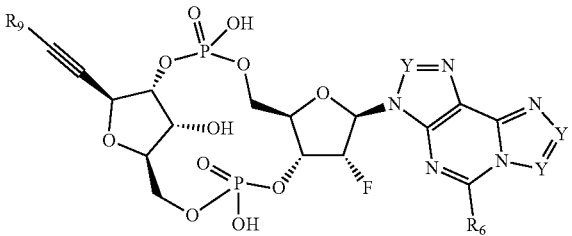

wherein
$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

In a 29th aspect of the invention, there is provided a compound of the formula

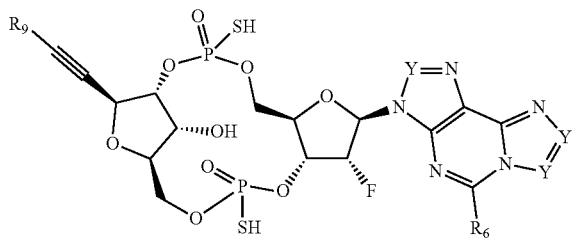

wherein
$R^{a1}$ is H or $C_{1-3}$ alkyl substituted with 0-6 $R^5$;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;
Y is $CR^5$ or N;
or a pharmaceutically acceptable salt, tautomer or stereoisomer thereof.

In a 30th aspect of the invention, there is provided a compound of the formula

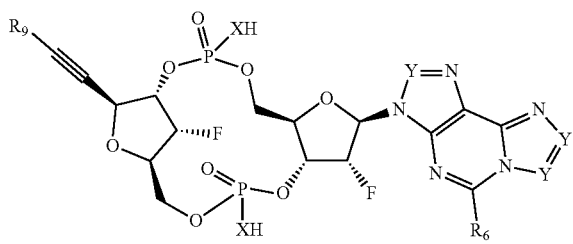

wherein
each X is independently O or S;
$R^{a1}$ is H or $C_{1-3}$ alkyl substituted with 0-6 $R^5$;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;
or a pharmaceutically acceptable salt, tautomer or stereoisomer thereof.

In another aspect of the invention, there are provided compounds of the formula

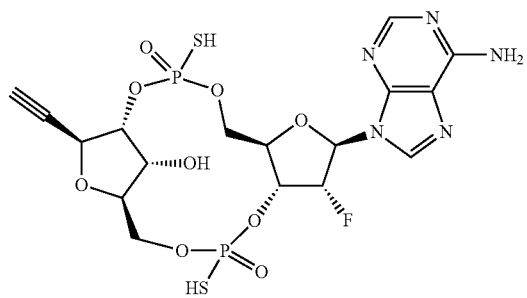

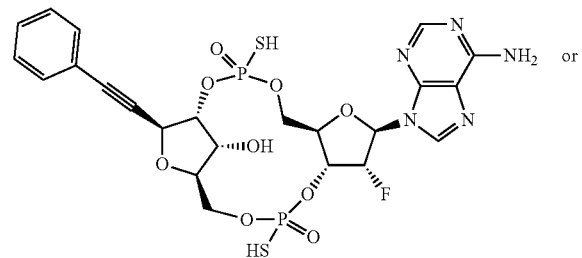 or

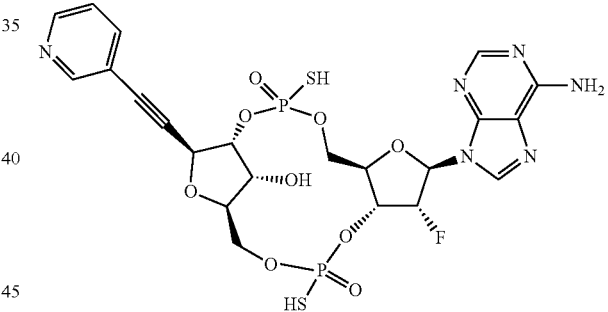

or a pharmaceutically acceptable salt, tautomer or stereoisomer thereof.

In another aspect of the invention, there is provided a compound of the formula (I)

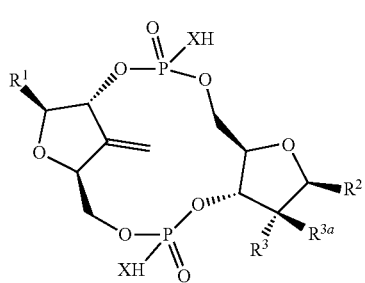

wherein
each X is independently O or S;
$R^1$ and $R^2$ are independently

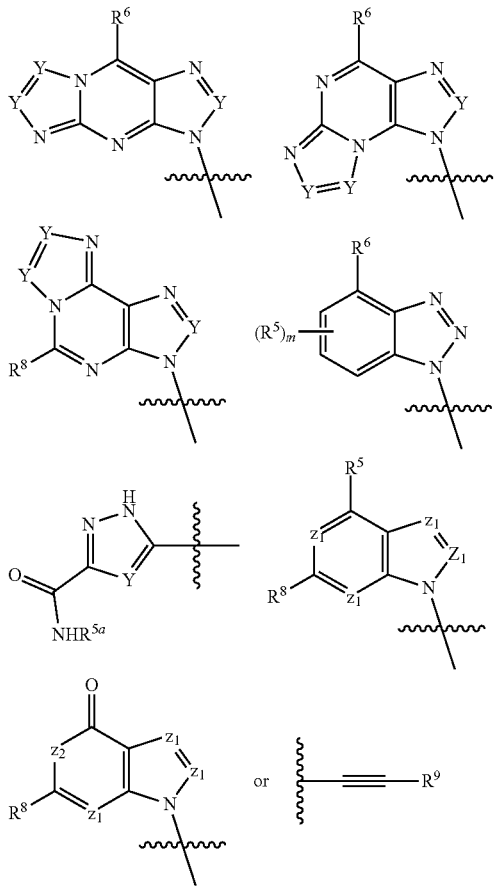

with the proviso that one of $R^1$ and $R^2$ must be

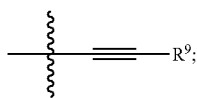

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl substituted with 0-6 $R^5$;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;
Y is $CR^5$ or N;
or a pharmaceutically acceptable salt, tautomer or stereoisomer thereof.

In another aspect of the invention, there are provided compounds of the formula

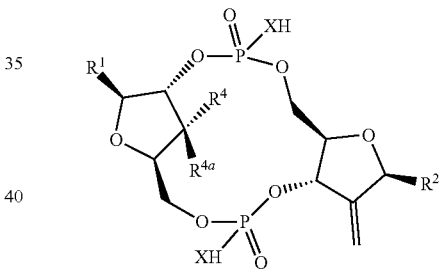

wherein
each X is independently O or S;
$R^1$ and $R^2$ are independently

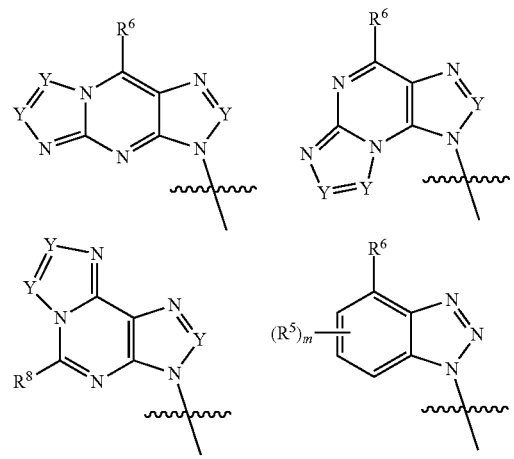

-continued

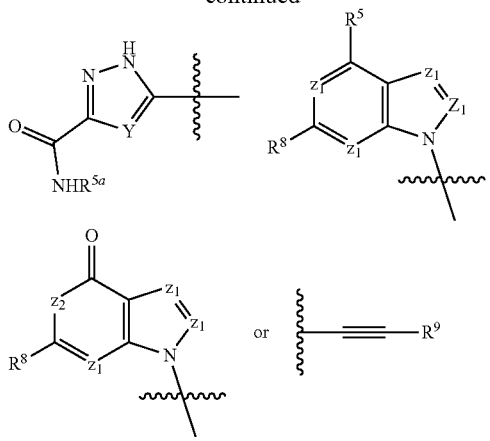

with the proviso that one of $R^1$ and $R^2$ must be

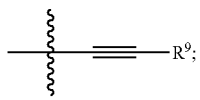

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}$COO$R^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl substituted with 0-6 $R^5$;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —C(O)$NR^{a1}R^{a1}$, —COO$R^{a1}$, —OC(O)$R^a$, —OC(O)$NR^{a1}R^{a1}$, —$NR^{a1}R^{a1}$, —$NR^{a1}C(O)R^{a1}$, —$NR^{a1}$COO$R^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}$COO$R^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}$COO$R^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;
Y is $CR^5$ or N;
or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect of the invention, there is provided a compound which is (1R,6R,8R,9R,10R,15R,17S,18R)-8-(6-amino-9H-purin-9-yl)-17-ethynyl-9-fluoro-18-hydroxy-3,12-disulfanyl-2,4,7,11,13,16-hexaoxa-3$\lambda^5$,12$\lambda^5$-diphosphatricyclo [13.2.1.0$^{6,10}$]octadecane-3,12-dione, (1S,6R,8R,9R,10R,15R,17S,18R)-8-(6-amino-9H-purin-9-yl)-17-ethynyl-9,18-difluoro-3,12-disulfanyl-2,4,7,11,13,16-hexaoxa-3$\lambda^5$,12$\lambda^5$-diphosphatricyclo [13.2.1.0$^{6,10}$]octadecane-3,12-dione, (1S,6R,8R,9R,10R,15R,17S,18R)-8-(6-amino-9H-purin-9-yl)-17-ethynyl-9,18-difluoro-3,12-dihydroxy-2,4,7,11,13,16-hexaoxa-3$\lambda^5$,12$\lambda^5$-diphosphatricyclo [13.2.1.0$^{6,10}$]octadecane-3,12-dione, (1R,6R,8R,9R,10R,15R,17S,18R)-8-(6-amino-9H-purin-9-yl)-9-fluoro-18-hydroxy-17-[2-(1H-imidazol-2-yl)ethynyl]-3,12-disulfanyl-2,4,7,11,13,16-hexaoxa-3$\lambda^5$,12$\lambda^5$-diphosphatricyclo[13.2.1.0$^{6,10}$]octadecane-3,12-dione, (1R,6R,8R,9R,10R,15R,17S,18R)-8-(6-amino-9H-purin-9-yl)-9-fluoro-3,12,18-trihydroxy-17-[2-(1H-imidazol-2-yl)ethynyl]-2,4,7,11,13,16-hexaoxa-3$\lambda^5$,12$\lambda^5$-diphosphatricyclo[13.2.1.0$^{6,10}$]octadecane-3,12-dione, (1R,6R,8R,9R,10R,15R,17S,18R)-8-(6-amino-9H-purin-9-yl)-9-fluoro-18-hydroxy-17-[2-(4-phenyl-1H-imidazol-5-yl)ethynyl]-3,12-disulfanyl-2,4,7,11,13,16-hexaoxa-3$\lambda^5$,12$\lambda^5$-diphosphatricyclo[13.2.1.0$^{6,10}$]octadecane-3,12-dione, (1R,6R,8R,9R,10R,15R,17S,18R)-8-(6-amino-9H-purin-9-yl)-9-fluoro-3,12,18-trihydroxy-17-[2-(4-phenyl-1H-imidazol-5-yl)ethynyl]-2,4,7,11,13,16-hexaoxa-3$\lambda^5$,12$\lambda^5$-diphosphatricyclo[13.2.1.0$^{6,10}$]octadecane-3,12-dione, (1R,6R,8R,9R,10R,15R,17S,18R)-8-(6-amino-9H-purin-9-yl)-9-fluoro-18-hydroxy-17-[2-(pyridin-3-yl)ethynyl]-3,12-disulfanyl-2,4,7,11,13,16-hexaoxa-3$\lambda^5$,12$\lambda^5$-diphosphatricyclo[13.2.1.0$^{6,10}$]octadecane-3,12-dione, (1R,6R,8R,9R,10R,15R,17S,18R)-8-(6-amino-9H-purin-9-yl)-9-fluoro-18-hydroxy-17-[2-(1H-pyrazol-4-yl)ethynyl]-3,12-disulfanyl-2,4,7,11,13,16-hexaoxa-3$\lambda^5$,12$\lambda^5$-diphosphatricyclo[13.2.1.0$^{6,10}$]octadecane-3,12-dione, (1R,6R,8R,9R,10R,15R,17S,18R)-8-(6-amino-9H-purin-9-yl)-9-fluoro-18-hydroxy-17-(2-phenylethynyl)-3,12-disulfanyl-2,4,7,11,13,16-hexaoxa-3$\lambda^5$,12$\lambda^5$-diphosphatricyclo[13.2.1.0$^{6,10}$]octadecane-3,12-dione, (1S,6R,8R,9R,10R,15R,17S,18R)-17-ethynyl-9,18-difluoro-3,12-dihydroxy-8-{3H-imidazo[2,1-f]purin-3-yl}-2,4,7,11,13,16-hexaoxa-3$\lambda^5$,12$\lambda^5$-diphosphatricyclo [13.2.1.0$^{6,10}$]octadecane-3,12-dione, (1S,6R,8R,9R,10R,15R,17S,18R)-17-ethynyl-9,18-difluoro-8-{3H-imidazo[2,1-f]purin-3-yl}-3,12-disulfanyl-2,4,7,11,13,16-hexaoxa-3$\lambda^5$,12$\lambda^5$-diphosphatricyclo [13.2.1.0$^{6,10}$]octadecane-3,12-dione, (1R,6R,8R,9R,10R,15R,17S,18R)-17-ethynyl-9-fluoro-3, 12,18-trihydroxy-8-{3H-imidazo[2,1-f]purin-3-yl}-2,4,7, 11,13,16-hexaoxa-3$\lambda^5$,12$\lambda^5$-diphosphatricyclo [13.2.1.0$^{6,10}$]octadecane-3,12-dione, (1R,6R,8R,9R,10R,15R,17S,18R)-17-ethynyl-9-fluoro-18-hydroxy-8-{3H-imidazo[2,1-f]purin-3-yl}-3,12-disulfanyl-2,4,7,11,13,16-hexaoxa-3$\lambda^5$,12$\lambda^5$-diphosphatricyclo [13.2.1.0$^{6,10}$]octadecane-3,12-dione, (1R,6R,8R,9R,10R,15R,17S,18R)-17-[2-(4-amino-2-hydroxypyrimidin-5-yl)ethynyl]-8-(6-amino-9H-purin-9-yl)-9-fluoro-18-hydroxy-3,12-disulfanyl-2,4,7,11,13,16-hexaoxa-3$\lambda^5$,12$\lambda^5$-diphosphatricyclo[13.2.1.0$^{6,10}$] octadecane-3,12-dione, or a pharmaceutically acceptable salt thereof or stereoisomer thereof.

OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The cyclic dinucleotides of the invention induce Type I interferons and/or pro-inflammatory cytokines in vitro in human cells, animal cells and human blood. The cytokine-inducting activity of these CDNs requires the presence of STING, as confirmed by in vitro experiments in human or animal cells.

The CDNs of the invention are agonists of the receptor STING.

The term "agonist" refers to any substance that activates a biologic receptor in vitro or in vivo to provoke a physiological response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively.

Another object of the present invention is the cyclic dinucleotides of Formula (I), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the cyclic dinucleotide of Formula (I) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the cyclic dinucleotides of the present invention can be used for cytokine induction immunotherapy of immunosuppressed individuals.

In this example, a cyclic dinucleotide of Formula (I) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a cyclic dinucleotide of Formula (I) or a pharmaceutically acceptable salt or prodrug thereof.

In another embodiment, the cyclic dinucleotides of the present invention can be used for cytokine induction immunotherapy in combination with chemotherapy. In this example, a cyclic dinucleotide of Formula (I) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof: a chemotherapeutic agent; and a cyclic dinucleotide of Formula (I) or a pharmaceutically acceptable salt or prodrug thereof.

Another object of the present invention is the cyclic dinucleotides of Formula (I) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof a cyclic dinucleotide of Formula (I) or a pharmaceutically acceptable salt or prodrug thereof.

Another object of the present invention is the cyclic dinucleotides of Formula (I) for use in the treatment of a pathology that may be alleviated by the induction of an immune response via the STING pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM4-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG, called AMP-224 In one aspect, In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1B) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any ele-

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

Additionally, the phosphorothioate group can be drawn as either

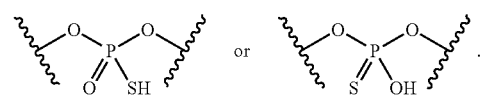 [SMILES: *OP(=O)(S)O* ; *OP(O)(=S)O*]

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, CF$_3$, CF$_2$CF$_3$, CN, halogen, haloalkyl, NO$_2$, sulfone, sulfoxide, ester, sulfonamide, carboxamide, alkoxy, alkoxyether, alkenyl, alkynyl, OH, C(O)alkyl, CO$_2$H, phenyl, heteroaryl, —O-phenyl, and —O— heteroaryl. Preferred examples of EWG include, but are not limited to, CF$_3$, CF$_2$CF$_3$, CN, halogen, SO$_2$(C$_{1-4}$ alkyl), CONH(C$_{1-4}$ alkyl), CON(C$_{1-4}$ alkyl)$_2$, and heteroaryl. More preferred examples of EWG include, but are not limited to, CF$_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, CD3 denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy,* 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J (Editor). *Prodrugs and Targeted Delivery* (*Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2007).

Compounds of Formula (I) may be prepared by reference to the methods illustrated in the following Scheme. As shown therein, the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

Scheme 1
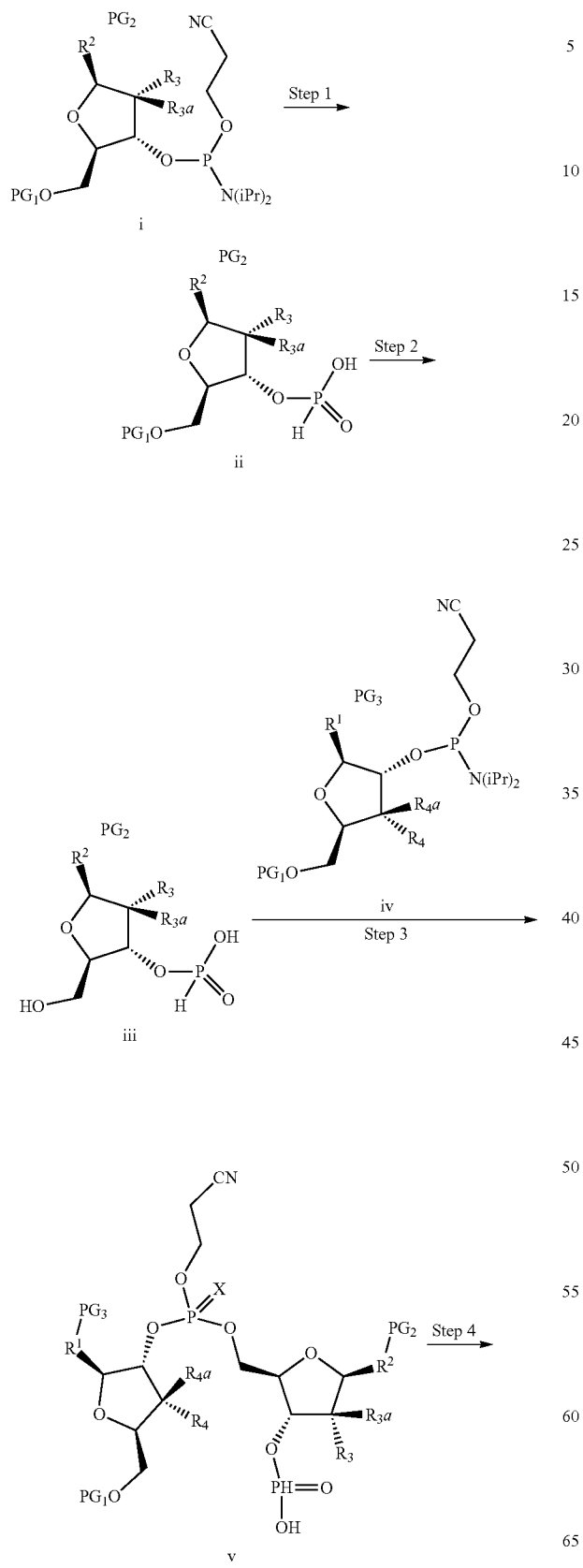
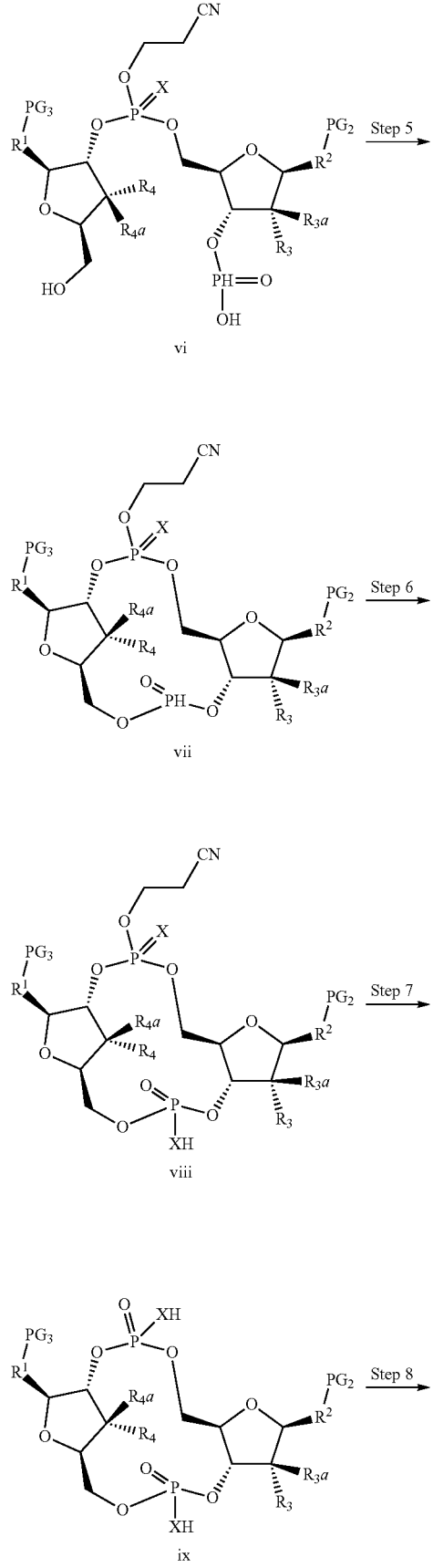

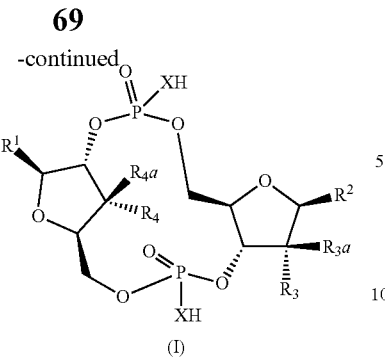

One method for preparation of examples of the present disclosure is described in Scheme1. The method starts from a ribo-nucleoside (i), wherein the nucleobase ($R^1$ or $R^2$) is appropriately protected (PG2 or PG3) when necessary, such as with a benzoyl group, and the 5'-hydroxy group is appropriately protected ($PG_1$), such as with a DMTr ether, and the 3'-position is a phosphoramidite functionality. In step 1, treatment with appropriate reagents, such as pyridine trifluoroacetate followed by butylamine, affords the H-phosphonate (ii). Subsequent removal of the 5'-OH protecting group in step 2, under acidic conditions ($PG_1$=DMTr) affords compounds of formula iii. The resulting compound of formula iii may be reacted with a fully protected 2'-phosphoramidite (iv) in step 3 and then immediately thiolated, for example with DDTT (X=S), to provide compounds of formula v. Alternatively, treatment with an oxidant such as t-butyl hydroperoxide affords compounds of formula v where X=O. Removal of the 5'-protecting group from the second ribo-nucleoside in step 4, under acidic conditions ($PG_1$=DMTr) provides compounds of formula vi. Treatment of compounds vi with an appropriate cyclization reagent in step 5, such as DMOCP provides compounds of formula vii. This material may then be immediately thiolated with an appropriate reagent, such as 3H-1,2-benzodithiol-3-one to afford compounds of formula viii in step 6. Compounds of formula viii may be treated with an appropriate reagent to remove the protecting groups of the nucleobase, for example $NH_4OH$/MeOH ($PG_2$ and $PG_3$=benzoyl) to afford compounds of formula ix. Compounds of formula (I) may be prepared in step 8 by removal of any remaining protecting group from using methods known to one skilled in the art.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

The following abbreviations may be used in the example section below and elsewhere herein:

| Abbreviation | Full Name |
| --- | --- |
| Ac | acetyl |
| ACN | acetonitrile |
| aq. | aqueous |
| DCM | dichloromethane |
| DDTT | ((dimethylamino-methylidene)amino)-3H-1,2,4-dithiazoline-3-thione |
| DMSO | dimethylsulfoxide |
| DMOCP | 2-chloro-5,5-dimethyl-1,3,2-dioxaphosphorinane 2-oxide |
| DMTr | 4,4'-dimethoxytrityl |
| EtOAc | ethyl acetate |
| $Et_3N$ or TEA | triethylamine |
| EtOH | ethanol |
| HPLC | high-performance liquid chromatography |
| iPr | isopropyl |
| MeOH | methanol |
| RT | room temperature |
| satd. or sat'd | saturated |
| TBS | tButyldimethylsilyl |
| TFA | Trifluoroacetic acid |
| $t_R$ | retention time |

Preparation of Intermediate I-1

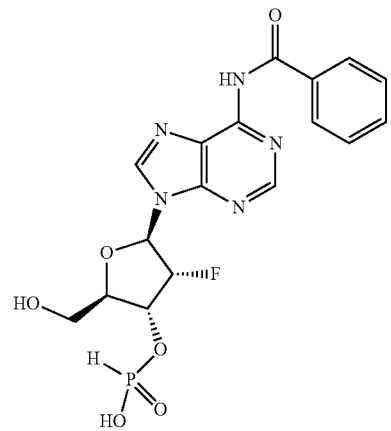

A solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl 2-cyanoethyl diisopropylphosphoramidite (Sigma-Aldrich, 2 g, 2.3 mmol) in ACN (5 mL) was treated with water (0.05 mL, 2.7 mmol), followed by pyridine trifluoroacetate (0.53 g, 2.7 mmol) The colorless solution was stirred for 10 min. and then concentrated in vacuo to afford a light pink foam. The resulting solid was dissolved in MeCN (5 mL) and concentrate to dryness. The resulting material was again dissolved in MeCN (5 mL). A solution of DBU (2.75 mL, 18.3 mmol) in ACN (6 mL) and nitromethane (1 mL, 18.3 mmol.) was prepared. To this DBU solution was added the ACN solution from above in one portion and the mixture was stirred for 20 min. The reaction was then poured into a 15 wt % aqueous solution of $KH_2PO_4$ (25 mL) and 2-MeTHF (20 mL) and agitated. The aqueous layer was extracted with 2-MeTHF (20 mL) and the combined organic layers were washed with a 15 wt % aqueous solution of $KH_2PO_4$ (2×20 mL), then a solution of brine (20 mL). The organic layer was dried over sodium sulfate, filtered and concentrated in vacuo. The resulting gel was dried by azeotropic distillation with 2-MeTHF (30-40 mL/g total, charged in 8-10 mL amounts). The crude material was then dissolved in DCM (20 mL). Methanol (1 mL) was added, followed by dichloroacetic acid (0.8 mL, 10.8 mmol). The reaction was stirred for 3 h. To this mixture was added pyridine (2 mL, 27 mmol) and then the mixture was concentrated in vacuo to a gel-like residue. Dimethoxy ethane (10 mL) was added and a white solid precipitated. The solids were collected by filtration and re-suspended in DME (2.5 mL/g) and agitated carefully with a spatula on the filter. The solids were again filtered and the process was repeated two more times to afford Intermediate I-1 as a white powder. (1 g, 72%).

Example 1

(1R,6R,8R,9R,10R,15R,17S,18R)-8-(6-amino-9H-purin-9-yl)-17-ethynyl-9-fluoro-18-hydroxy-3,12-disulfanyl-2,4,7,11,13,16-hexaoxa-3$\lambda^5$,12$\lambda^5$-diphosphatricyclo[13.2.1.0$^{6,10}$]octadecane-3,12-dione

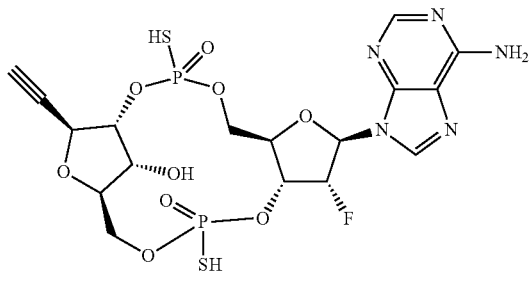

Diastereomer 1 (1-1)
Diastereomer 2 (1-2)

Preparation of Intermediate 1A

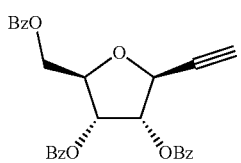

1A

To a solution of ethynyltrimethylsilane (5.84 g, 59.5 mmol) in toluene (50 mL) at 0° C. was added 1.6 M nBuLi (31.0 mL, 49.6 mmol) in hexane, and then the mixture was stirred at 0° C. for 30 min. To this mixture was added 25% diethyl aluminum chloride (26.9 mL, 49.6 mmol) in toluene and the resulting mixture was stirred for another 30 min, and then a solution of (2S,3R,4R,5R)-2-acetoxy-5-((benzoyloxy)methyl)tetrahydrofuran-3,4-diyl dibenzoate (10 g, 19.82 mmol) in DCM (25 mL) was added dropwise. The resulting mixture was stirred at 0° C. for 1h, and then slowly warmed to room temperature. After stirring for 4 h, the reaction was diluted with EtOAc, cooled to 0° C., and quenched carefully with 1N HCl (60 mL). The reaction mixture was extracted with EtOAc, and the combined extracts were washed with sat. aq. NaHCO$_3$ and brine, dried over MgSO$_4$, filtered and concentrated to an oil. The resulting oil was dissolved in THF (100 mL), cooled to 0° C., and 1.0 M TBAF (19.72 mL, 19.72 mmol) in THF was slowly added. The reaction was stirred for 30 min, and then sat. aq. NH$_4$Cl solution was added. The mixture was extracted with EtOAc, and the organic layer was washed with brine, dried over MgSO$_4$ filtered and concentrated. The residue was purified by silica column chromatography (220 g ISCO column, EtOAc/hexane=0-15% for 25 min, then 15-40% for 10 min) to give Intermediate 1A (4.13 g, 44.5% yield). HPLC: Retention time=1.14 min (H$_2$O/ACN with 0.05% TFA, Waters Acquity HPLC BEH C18, 2.1×50 mm, 1.7-μm particles, gradient=2 min, wavelength=220 nm); MS (ES): m/z=471 [M+H]$^+$. $^1$H NMR (499 MHz, CHLOROFORM-d) δ 8.12 (dd, J=8.3, 1.3 Hz, 2H), 8.04-8.00 (m, 2H), 7.93 (dd, J=8.4, 1.3 Hz, 2H), 7.62-7.53 (m, 3H), 7.46-7.41 (m, 4H), 7.39-7.34 (m, 2H), 5.89 (dd, J=6.3, 5.2 Hz, 1H), 5.86-5.81 (m, 1H), 4.97 (dd, J=3.9, 2.2 Hz, 1H), 4.77 (dd, J=11.8, 3.6 Hz, 1H), 4.66 (dt, J=6.3, 4.0 Hz, 1H), 4.62-4.57 (m, 1H), 2.64 (d, J=2.2 Hz, 1H).

Preparation of Intermediate 1B

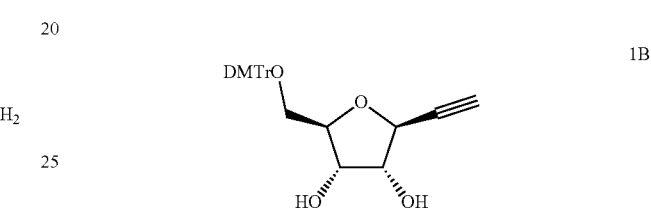

1B

To a solution of Intermediate 1A (3.8 g, 8.08 mmol) in MeOH (50 mL) was added sodium methoxide (0.218 g, 4.04 mmol) and the resulting mixture was stirred at room temperature overnight and then concentrated. The resulting residue was azeotroped with CH$_3$CN two times, and then dissolved in pyridine (40 mL), and then concentrated to about 30 mL final volume. To this solution was added 4,4'-(chloro(phenyl) methylene)bis(methoxybenzene) (4.10 g, 12.11 mmol) and the mixture was stirred at room temperature overnight. The reaction was then quenched with EtOH (5 mL) and stirred for 30 min. The mixture was then concentrated, and the residue was dissolved in DCM, and washed with sat aq. NaHCO$_3$. The organic layer was concentrated and the residue was purified by silica column chromatography (80 g ISCO column, EtOAc/hexane=0-100%) to give Intermediate 1B (0.99 g, 27% yield). HPLC: retention time=1.03 min (H$_2$O/ACN with 0.05% TFA, Waters Acquity HPLC BEH C18, 2.1×50 mm, 1.7-μm particles, gradient=2 min, wavelength=220 nm); MS (ES): m/z=483 [M+Na]$^+$. $^1$H NMR (499 MHz, CHLOROFORM-d) δ 7.48 (dd, J=8.4, 1.3 Hz, 2H), 7.42-7.34 (m, 4H), 7.33-7.29 (m, 2H), 7.24 (d, J=7.3 Hz, 1H), 6.85 (dd, J=8.9, 0.7 Hz, 4H), 4.59-4.47 (m, 1H), 4.36 (br s, 1H), 4.25 (t, J=4.7 Hz, 1H), 4.02 (q, J=4.8 Hz, 1H), 3.81 (s, 6H), 3.42-3.31 (m, 1H), 3.32-3.22 (m, 1H), 2.73 (br s, 1H), 2.57 (d, J=2.1 Hz, 1H), 2.50 (br s, 1H).

Preparation of Intermediate 1C

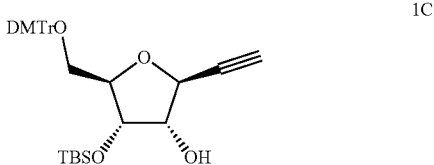

1C

To a solution of Intermediate 1B (0.99 g, 2.15 mmol) in DMF (4 mL) was added imidazole (0.439 g, 6.45 mmol) and TBSCl (0.340 g, 2.257 mmol). The mixture was stirred at room temperature overnight. Additional TBSCl (120 mg) was then added and the mixture was stirred for 40 min. The mixture was then diluted with ether, washed with sat. aq. NaHCO$_3$ and brine, dried over MgSO$_4$, filtered and then concentrated. The residue was purified by silica column chromatography (80 g GOLD ISCO column, EtOAc/hexane, 0-10% for 20 min, then hold at 10% for 30 min to give Intermediate 1C (373 mg, 30%). HPLC: retention time=1.36 min (H$_2$O/ACN with NH$_4$OAc, Waters Acquity HPLC BEH C18, 2.1×50 mm, 1.7-µm particles, gradient=2 min, wavelength=220 nm); MS (ES): m/z=573 [M−H]$^-$. $^1$H NMR (700 MHz, DMSO-d6) δ 7.45-7.38 (m, 2H), 7.33-7.24 (m, 6H), 7.23-7.18 (m, 1H), 6.86 (d, J=8.7 Hz, 4H), 5.19 (s, 1H), 4.35 (dd, J=4.7, 2.2 Hz, 1H), 4.12 (t, J=5.1 Hz, 1H), 3.98 (t, J=4.7 Hz, 1H), 3.81 (q, J=5.0, 4.6 Hz, 1H), 3.72 (s, 6H), 3.57 (d, J=2.1 Hz, 1H), 3.18 (dd, J=10.4, 3.2 Hz, 1H), 2.86 (dd, J=10.4, 4.4 Hz, 1H), 0.74 (s, 9H), −0.03 (s, 3H), −0.10 (s, 3H).

Preparation of Intermediate 1D

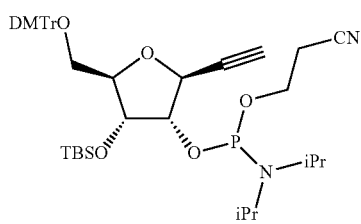

1D

To a solution of Intermediate 1C (373 mg, 0.649 mmol) in DCM (4 mL) was added 1.0 M 1H-imidazole-4,5-dicarbonitrile (0.454 mL, 0.454 mmol) in acetonitrile, followed by 3-((bis(diisopropylamino)phosphanyl)oxy)propanenitrile (313 mg, 1.038 mmol), and the reaction mixture was stirred at room temperature overnight. The reaction was quenched with MeOH (0.1 mL), and stirred for 3 min. The mixture was then diluted with DCM, and washed with sat. aq. NaHCO$_3$, then dried over MgSO$_4$ filtered and concentrated. The residue was purified by silica gel chromatography (12 g ISCO column, column was pretreated with 1% TEA/hexane, then run with EtOAc/hexane=0-40%) to give Intermediate 1D (398 mg, 79% yield) as mixture of two diastereomers. HPLC: retention time=1.49 min and 1.60 min (H$_2$O/ACN with NH$_4$OAc, Waters Acquity HPLC BEH C18, 2.1×50 mm, 1.7-µm particles, gradient=2 min, wavelength=220 nm); MS (ES): m/z=775 [M+H]$^+$.

Preparation of Intermediate 1E

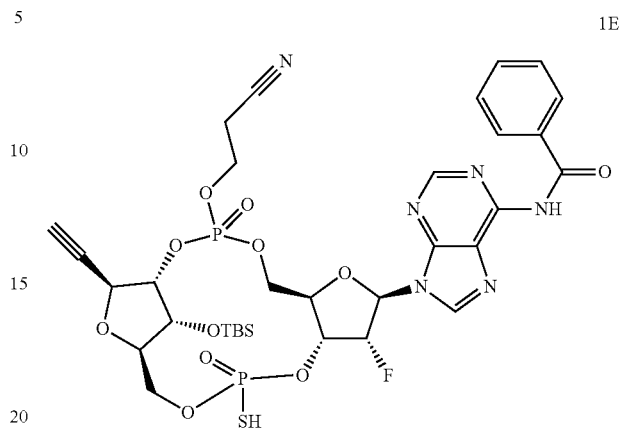

1E

Intermediate 1D (398 mg, 0.514 mmol) was dissolved in anhydrous ACN (8 mL) and dried by co-evaporation (3×8 mL), the final time leaving ~4 mL of ACN. Molecular sieve (4 Å) were added and the mixture was set aside under a nitrogen atmosphere. To Intermediate I-1 (225 mg, 0.514 mmol) was added pyridine (10 mL) and the mixture was concentrated to dryness. Pyridine trifluoroacetate (109 mg, 0.565 mmol) and a stirbar were added and the mixture was concentrated to dryness. This procedure was repeated two more times. Then ACN (8 mL) was added and the mixture was co-evaporated three times. The final time, the mixture was concentrated to ~2 mL final volume. To the solution of Intermediate I-1 was added the above solution of Intermediate 1D (398 mg, 0.514 mmol) by cannula. The mixture was stirred for 5 min, then ((dimethylamino-methylidene)amino)-3H-1,2,4-dithiazoline-3-thione (116 mg, 0.565 mmol) was added and the mixture was stirred for 30 min at room temperature. The reaction mixture was then filtered, and the solid was washed with ACN, and the filtrate was concentrated. The residue was dissolved in DCM (6 mL) and then water (93 µl, 5.14 mmol) and 6% (v/v) Cl$_2$CHCO$_2$H (6 mL) were added, and the reaction was stirred for 10 min at room temperature. Pyridine (1 mL) was added, and the resulting mixture was concentrated to dryness. The resulting residue was dissolved in pyridine (10 mL), and then concentrated to a volume of approximately 6 mL. 2-Chloro-5,5-dimethyl-1,3,2-dioxaphosphorinane 2-oxide (DMOCP) (349 mg, 1.890 mmol) was added and the reaction was stirred at room temperature for 5 min. Water (324 µl, 17.97 mmol) was added immediately followed by the addition of ((dimethylamino-methylidene)amino)-3H-1,2,4-dithiazoline-3-thione (116 mg, 0.565 mmol), and the reaction was stirred at room temperature for 5 min. The reaction mixture was then poured into 50 mL of water containing NaHCO$_3$ (1.6 g) and stirred for 10 min. The mixture was extracted with (EtOAc/Et$_2$O=1/1) (3×40 mL). The combined extracts were concentrated and azeotroped with toluene two times. The residue was then dissolved in a small volume of DCM and purified by silica gel chromatography (12 g column, first EtOAc/hexane=0-100%, then MeOH=0-20%). The desired fractions were combined and concentrated to give Intermediate 1E (90 mg) as a mixture of two major diasteremers. HPLC: RT=0.99 min and 1.05 min (H$_2$O/ACN with 0.05%

TFA, Waters Acquity HPLC BEH C18, 2.1×50 mm, 1.7-μm particles, gradient=2 min, wavelength=220 nm); MS (ES): m/z=855 [M+H]+.

Preparation of Examples 1-1 and 1-2

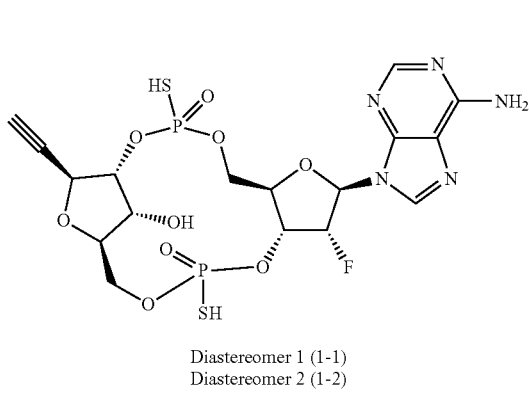 [SMILES: C#C[C@@H]1O[C@@H]2COP(=O)(S)O[C@H]3[C@@H](F)[C@H](n4cnc5c(N)ncnc54)O[C@@H]3COP(=O)(S)O[C@@H]1[C@@H]2O]

Diastereomer 1 (1-1)
Diastereomer 2 (1-2)

Intermediate 1E (80 mg, 0.094 mmol) was treated with 7N NH$_3$ in MeOH (5 mL) and stirred at room temperature overnight. The reaction mixture was concentrated, and the residue was purified by reverse phase ISCO chromatography (50 g C18 column, 0-50% ACN/H$_2$O, NH$_4$OAc). The desired fractions were combined and concentrated. The residue was then treated with 3HF.TEA (0.2 mL), heated at 55° C. for 2h, and then cooled to room temperature. The mixture was then diluted with 1M triethylammonium acetate and the crude material was purified via preparative LC/MS (Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-40% B over 20 minutes, then a 4-minute hold at 100% B; Flow: 20 mL/min.) to give Examples 1-1 and 1-2.

Example 1-1: HPLC: retention time=1.99 min: (Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm); MS (ES): m/z=584 [M+H]+.

Example 1-2: HPLC: retention time=2.06 min: (Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm); MS (ES): m/z=584 [M+H]+.

An alternative synthesis of Example 1, including an additional diastereomer is provided below.

Examples 1-1, 1-2, and 1-3

(1R,6R,8R,9R,10R,15R,17S,18R)-8-(6-amino-9H-purin-9-yl)-17-ethynyl-9-fluoro-3,12,18-trihydroxy-2,4,7,11,13,16-hexaoxa-3λ$^5$,12λ$^5$-diphosphatricyclo[13.2.1.0$^{6,10}$]octadecane-3,12-dithione

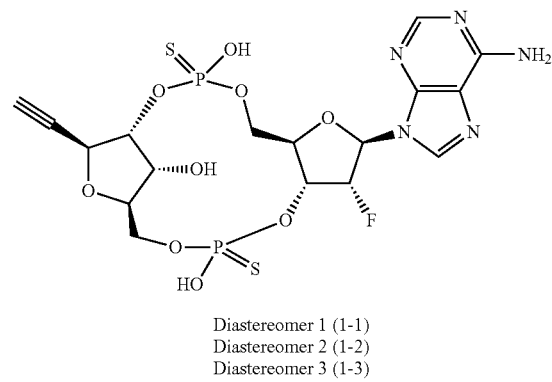 [SMILES: C#C[C@@H]1O[C@@H]2COP(O)(=S)O[C@H]3[C@@H](F)[C@H](n4cnc5c(N)ncnc54)O[C@@H]3COP(O)(=S)O[C@@H]1[C@@H]2O]

Diastereomer 1 (1-1)
Diastereomer 2 (1-2)
Diastereomer 3 (1-3)

Preparation of Intermediate 1F

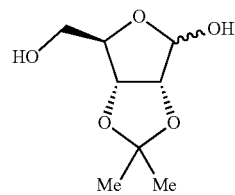

1F

To a suspension of D-ribose (20.0 g, 133 mmol) in acetone (250 mL) was added concentrated sulfuric acid (0.60 mL, 11.3 mmol) dropwise via syringe. The resulting suspension was stirred vigorously at room temperature for 1 hour, during which time all the solids gradually went into solution. The reaction was then neutralized with solid sodium bicarbonate (added in excess) and filtered. The filtrate was concentrated in vacuo to afford Intermediate 1F (26.7 g) as a clear pale yellow oil. The crude product was carried forward without further purification. $^1$H NMR (500 MHz, CHLOROFORM-d, major anomer) δ 5.42 (d, J=6.3 Hz, 1H), 4.85 (d, J=6.0 Hz, 1H), 4.69 (d, J=6.4 Hz, 1H), 4.59 (d, J=6.0 Hz, 1H), 4.42 (t, J=2.4 Hz, 1H), 3.79-3.71 (m, 2H), 3.59-3.50 (m, 1H), 1.49 (s, 3H), 1.33 (s, 3H).

Preparation of Intermediate 1G

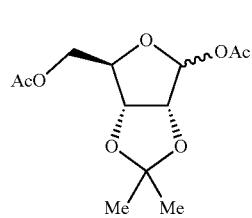

1G

To a solution of crude Intermediate 1F (25.3 g, ~133 mmol) in pyridine (80 mL) was added acetic anhydride (37.7 mL, 400 mmol). The resulting mixture was stirred at room temperature under nitrogen atmosphere for 6 hours. The reaction was then quenched carefully with MeOH (20 mL) and concentrated in vacuo. The crude product was dissolved in a small amount of DCM, adsorbed onto a plug of $SiO_2$, and purified by flash chromatography ($SiO_2$, 0 to 50% EtOAc/hexanes) to afford Intermediate 1G (33 g, 120 mmol, 90% yield) as a clear colorless oil. $^1$H NMR (500 MHz, CHLOROFORM-d) δ 6.23 (s, 1H), 4.72 (s, 2H), 4.47 (t, J=6.7 Hz, 1H), 4.19-4.07 (m, 2H), 2.10 (s, 3H), 2.07 (s, 3H), 1.51 (s, 3H), 1.34 (s, 3H). LCMS: RT=0.75 min. $[M+Na]^+$ =297. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 220 nm.

Preparation of Intermediate 1H

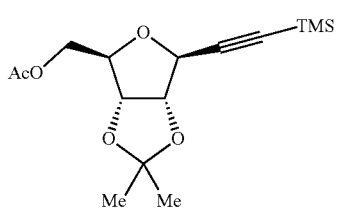

1H

A suspension of indium powder (10.0 g, 88 mmol) in DCE (50 mL) was stirred at room temperature for 20 min under nitrogen atmosphere. A solution of Intermediate 1G (10.0 g, 36.5 mmol) and (iodoethynyl)trimethylsilane (11 mL, 72.9 mmol) in DCE (10 mL) was added to the reaction flask via syringe, followed by 2×5 mL rinses with DCE (10 mL). The reaction flask was outfitted with a reflux condenser and the entire setup was evacuated and backfilled with nitrogen 3 times. The reaction was then stirred at reflux for 4 hours under nitrogen atmosphere. The crude reaction mixture was filtered through a pad of Celite (rinsed copiously with acetone) and the filtrate was concentrated in vacuo to afford a tarry dark oil. The crude product was purified by flash chromatography ($SiO_2$, 750 g column, 0% to 30% EtOAc/hexanes, 44 min gradient, 300 mL/min) to afford Intermediate 1H (4.56 g, 14.6 mmol, 40% yield). H NMR (500 MHz, CHLOROFORM-d) δ 4.82 (dd, J=6.2, 2.4 Hz, 1H), 4.70-4.66 (m, 2H), 4.34-4.19 (m, 3H), 2.10 (s, 3H), 1.52 (s, 3H), 1.35 (s, 3H), 0.17 (s, 9H).

Preparation of Intermediate 1I

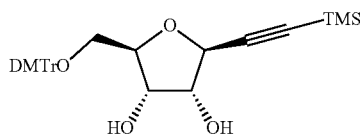

1I

To a solution of Intermediate 1H (2.0 g, 6.40 mmol) in MeOH (20 mL) was added concentrated aqueous HCl (3.7 mL, 44.8 mmol). The resulting suspension was stirred at 60° C. for 1 h. The reaction was then allowed to cool to room temperature and concentrated in vacuo. The residue was co-evaporated with pyridine 2× then dried under high vacuum to afford the crude triol (1.53 g). This material was carried into the next step without further purification. To a solution of the crude triol in pyridine (33 mL) was added 4,4'-(chloro(phenyl)methylene)bis(methoxybenzene) (2.76 g, 8.14 mmol). The resulting mixture was stirred at room temperature overnight. The reaction was then quenched by adding MeOH (10 mL). The mixture was stirred for another 5 min and then concentrated in vacuo. The residue was treated with water and extracted with EtOAc (3×). The combined organic layers were dried ($Na_2SO_4$), filtered, and concentrated in vacuo. The crude product was dissolved in a minimal amount of DCM and purified by flash chromatography ($SiO_2$, 80 g column [pre-treated with successive washes of 5% $Et_3N$ in DCM, 100% EtOAc, and 100% hexanes], 0% to 100% EtOAc/hexanes) to afford Intermediate 1I (3.1 g, 5.82 mmol, 89% yield over 2 steps) as a white foam. $^1$H NMR (500 MHz, METHANOL-$d_4$) δ 7.55-7.49 (m, 2H), 7.42-7.35 (m, 4H), 7.32-7.26 (m, 2H), 7.23-7.17 (m, 1H), 6.90-6.82 (m, 4H), 4.48 (d, J=5.4 Hz, 1H), 4.28 (t, J=5.1 Hz, 1H), 4.13-4.10 (m, 1H), 4.02-3.96 (m, 1H), 3.79 (s, 6H), 3.30 (dd, J=10.3, 3.1 Hz, 1H), 3.08 (dd, J=10.2, 4.6 Hz, 1H), 0.12 (s, 9H). LCMS: RT=1.15 min. $[M+K]^+$=571. Column: Waters BEH C18 2.1×50 mm 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 5% B to 95% B over 1 min, then a 0.5 min hold at 95% B; Flow: 0.8 mL/min; Detection: UV at 220 nm.

Preparation of Intermediate 1B

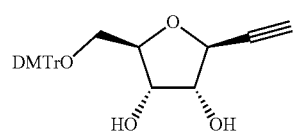

1B

To a cooled (0° C.) solution of Intermediate 1I (1.77 g, 3.32 mmol) in THF (17 ml) was added TBAF (1M soln in THF) (3.3 mL, 3.3 mmol). The reaction immediately turned a dark red color. After 30 min, the reaction was quenched with sat. aq. $NH_4Cl$ and extracted with EtOAc (3×). The organic layers were combined, dried ($Na_2SO_4$), filtered, and concentrated in vacuo to afford a brown residue. The crude product was dissolved in a small amount of DCM and purified by flash chromatography ($SiO_2$, 120 g column, 0% to 100% EtOAc/hexanes, 19 min gradient, 40 mL/min) to afford Intermediate 1B (1.37 g, 2.97 mmol, 90% yield) as a pink foam. LCMS: RT=0.98 min. $[M+acetate]^-$=519. Column: Waters BEH C18 2.1×50 mm 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 5% B to 95% B over 1 min, then a 0.5 min hold at 95% B; Flow: 0.8 mL/min; Detection: UV at 220 nm.

Intermediates 1C and 1D were prepared from Intermediate 1B as described above.

Preparation of Intermediate 1J

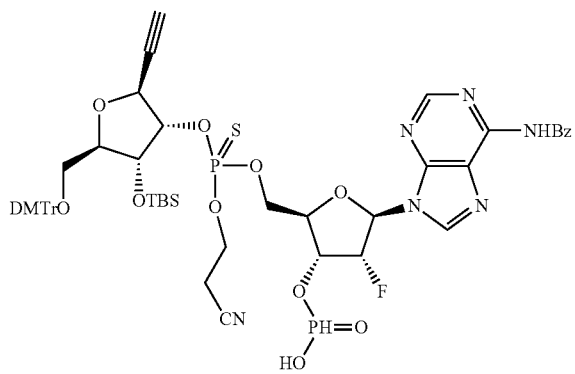

Intermediate 1D (320 mg, 0.413 mmol) was azeotroped with acetonitrile (3×10 mL), leaving ~5 mL acetonitrile when evaporating the final time. Molecular sieves (4 Å, 150 mg) were added and the mixture was set aside under nitrogen atmosphere. In a separate flask, Intermediate I-1 (181 mg, 0.413 mmol) and 1H-tetrazole (87 mg, 1.24 mmol) were azeotroped with acetonitrile (15 mL). A stirbar was added, then the mixture was azeotroped with acetonitrile (2×15 mL), leaving ~10 mL acetonitrile when evaporating the final time. Molecular sieves (4 Å, 150 mg) were added, then the solution of Intermediate 1D prepared earlier was added via syringe. The reaction was monitored by LCMS. Upon consumption of Intermediate 1D, solid (E)-N,N-dimethyl-N'-(3-thioxo-3H-1,2,4-dithiazol-5-yl)formimidamide (DDTT) (85 mg, 0.413 mmol) was then added and stirring was continued for 10 min. The yellow solution was carefully concentrated in vacuo. The residue was taken up in dichloromethane and washed with 6% (m/v) aqueous sodium bicarbonate. The organic phase was then dried over $Na_2SO_4$, filtered, and concentrated. The crude product was purified by flash chromatography ($SiO_2$, 40 g RediSep Rf Gold column [pre-treated with successive washes of 5% $Et_3N$ in DCM, 100% EtOAc, and 100% hexanes], 0 to 100% EtOAc/hexanes followed by 0 to 50% MeOH/DCM) to afford Intermediate 1J (231 mg, 0.202 mmol, 49% yield). LCMS: RT=1.14 min. $[M+Na]^+$=1143. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 1K

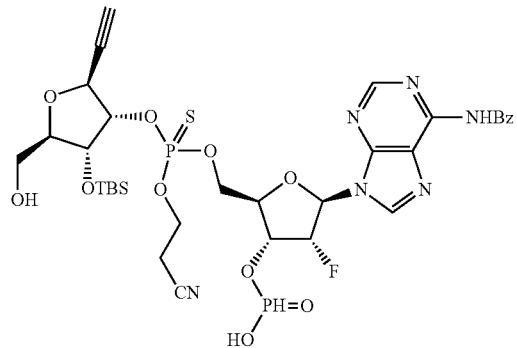

To a solution of Intermediate 1J (81 mg, 0.096 mmol) and triethylsilane (0.277 mL, 1.73 mmol) in DCM (1 mL) was added dichloroacetic acid (0.048 mL, 0.577 mmol) dropwise. The solution turned a bright pink color, which gradually faded and became colorless over about one hour. The reaction was quenched with pyridine (2 mL) and stirred for 10 minutes, then concentrated in vacuo. The residue was azeotroped with pyridine (2×2 mL). The crude product was purified by reversed phase MPLC (C18, 50 g RediSep Rf Gold column, 0-60% acetonitrile/water containing 10 mM ammonium acetate) to afford Intermediate 1K (81 mg, 0.096 mmol, 50% yield). LCMS: RT=0.86, 0.87 min. $[M+Na]^+$=841. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 1L

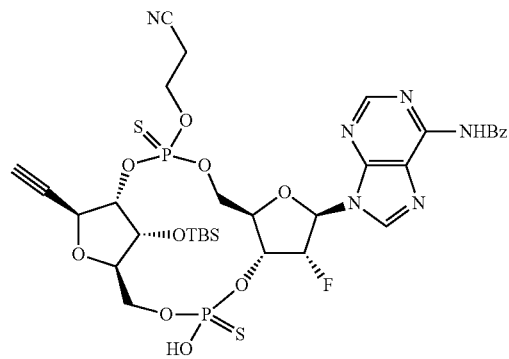

To a solution of Intermediate 1K (81 mg, 0.096 mmol; azeotroped with pyridine 3×) in pyridine (2 mL) was added a solution of 2-chloro-5,5-dimethyl-1,3,2-dioxaphosphinane 2-oxide (DMOCP) (71.1 mg, 0.385 mmol; azeotroped with pyridine 1×) in pyridine (0.5 mL). The reaction was stirred for 20 min at room temperature, then solid (E)-N,N-dimethyl-N'-(3-thioxo-3H-1,2,4-dithiazol-5-yl)formimidamide (39.6 mg, 0.193 mmol) was added. The resulting solution was stirred for 30 minutes, then 1 mL of water was added and stirring was continued for 10 min. The reaction mixture was then poured into 50 mL water containing NaHCO$_3$ (1.6 g) and stirred for 10 min. The mixture was extracted with EtOAc (3×40 mL) and the combined organic layers were concentrated and co-evaporated with toluene twice to remove residual pyridine. The crude product was dissolved in a small amount of DCM and purified by flash chromatography (SiO$_2$, 12 g RediSep Rf Gold column, 0 to 50% MeOH/DCM, 25 min gradient) to afford Intermediate 1L (57 mg, 0.067 mmol, 69% yield) as a mixture of 4 diastereomers. LCMS: RT=0.96, 1.03 min (major isomers). [M+Na]$^+$ =855. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 1M

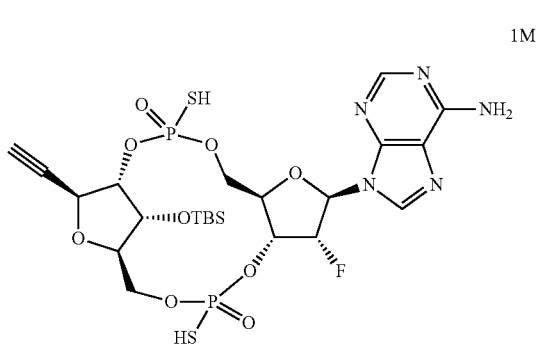 [SMILES: C#C[C@@H]1O[C@@H]2COP(=O)(S)O[C@H]3[C@@H](F)[C@H](n4cnc5c(N)ncnc54)O[C@@H]3COP(=O)(S)O[C@@H]1[C@@H]2O[Si](C)(C)C(C)(C)C]

1M

A solution of Intermediate 1L (57 mg, 0.067 mmol) in MeOH (1 mL) and conc. NH$_4$OH (1 mL) was heated in a sealed pressure vessel at 50° C. overnight. The reaction vessel was cooled in an ice-water bath for 10 min before opening. The reaction mixture was transferred to a round-bottom flask and evaporated to dryness. The crude product Intermediate 1M (50 mg) was carried into the next step without further purification. LCMS: RT=0.72, 0.81 min (major isomers). [M+Na]$^+$=698. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Examples 1-1, 1-2, and 1-3

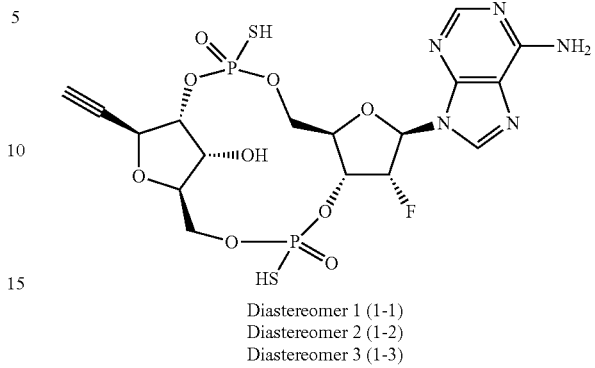

Diastereomer 1 (1-1)
Diastereomer 2 (1-2)
Diastereomer 3 (1-3)

Crude Intermediate 1M (50 mg, ~0.072 mmol) was treated with pyridine (0.2 mL) and TEA.3HF (0.8 mL) at 50° C. for 5 h. The reaction mixture was then added dropwise to a cooled solution of 1M triethylammonium acetate (10 mL) (note: gas evolution) and concentrated. The crude material was purified via preparative LC/MS with the following conditions: Column: Agilent Bonus RP 21.2×100 mm, 5 μm particles; Mobile Phase A: water with 20-mM ammonium acetate; Mobile Phase B: acetonitrile; Gradient: 0% B hold 0-6 minute. 0%-25% B over 16 minutes, then a 4-minute hold at 100% B; Flow: 20 mL/min. Fractions containing the desired product were combined and dried to afford Examples 1-1 (3.1 mg), 1-2 (3.7 mg), and 1-3 (1.1 mg).

Example 1-1: LCMS: RT=1.74 min. [M+H]$^+$=584.
Example 1-2: LCMS: RT=1.92 min. [M−H]$^-$=582.
Example 1-3: LCMS: RT=2.14 min. [M+H]$^+$=584.

Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 and 254 nm).

Examples 2-1, 2-2, 2-3, and 2-4

(1R,6R,8R,9R,10R,15R,17S,18R)-8-(6-amino-9H-purin-9-yl)-9-fluoro-3,12,18-trihydroxy-17-(2-phenylethynyl)-2,4,7,11,13,16-hexaoxa-3λ$^5$,12λ$^5$-diphosphatricyclo[13.2.1.0$^{6,10}$]octadecane-3,12-dithione

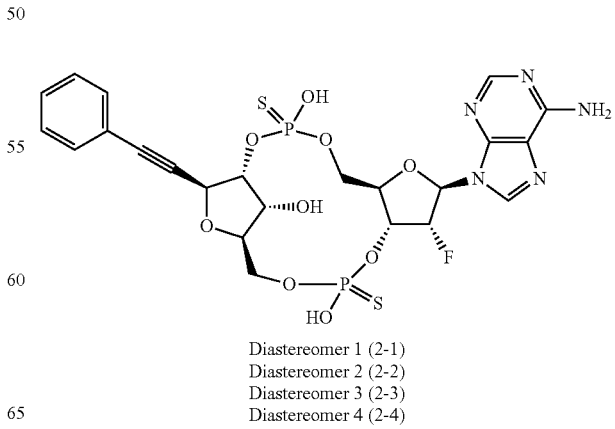

Diastereomer 1 (2-1)
Diastereomer 2 (2-2)
Diastereomer 3 (2-3)
Diastereomer 4 (2-4)

Preparation of Intermediate 2A

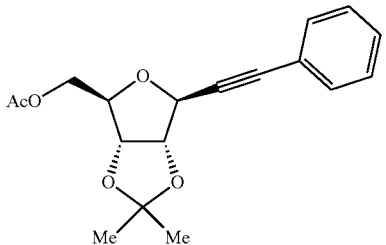

2A

A stirred suspension of indium powder (502 mg, 4.38 mmol) in anhydrous DCE (10 mL) was bubbled with nitrogen at room temperature for 20 min. A solution of Intermediate 1B (2.00 g, 7.29 mmol) and (iodoethynyl) benzene (3.33 g, 14.6 mmol) (prepared as described in Meng, L. G., et al. Synth. Commun. 2008, 38, 225) in DCE (10 mL) was bubbled with nitrogen and then transferred to the vessel containing the indium suspension. The resulting mixture was bubbled with nitrogen for a few minutes, then the cap was sealed and the sealed tube was stirred for 6 h at 90° C. The mixture was then allowed to cool to room temperature, filtered through Celite, and washed with DCM (50 mL). To the filtrate was added 10% NaHCO$_3$ (20 mL) and the mixture was extracted with DCM (2×10 mL). The combined organic layers were dried (Na$_2$SO$_4$), filtered, and concentrated in vacuo. The crude product was purified by flash chromatography (SiO$_2$, 80 g column, 0% to 50% EtOAc/hexanes) to afford Intermediate 2A (1.08 g, 3.40 mmol, 47% yield). LCMS: RT=0.99 min. [M+H]$^+$=317. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 220 nm.

Preparation of Intermediate 2B

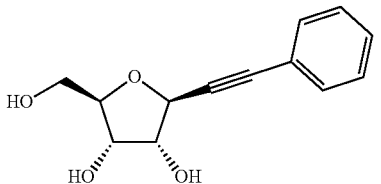

2B

To a solution of Intermediate 2A (1.00 g, 3.16 mmol) in MeOH (10 mL) was added concentrated aqueous HCl (1.8 mL, 22.1 mmol). The resulting suspension was stirred at 60° C. for 1 h. The reaction was then allowed to cool to room temperature and concentrated in vacuo. The remaining aqueous suspension was diluted with brine (25 mL) and extracted with EtOAc (2×100 mL). The combined organic layers were washed with 10% NaHCO$_3$, dried (Na$_2$SO$_4$), filtered, and concentrated in vacuo. The crude product was purified by flash chromatography (SiO$_2$, 80 g column, 0% to 100% EtOAc/hexanes) to afford Intermediate 2B (637 mg, 2.72 mmol, 86% yield). $^1$H NMR (500 MHz, CHLOROFORM-d) δ 7.44-7.40 (m, 2H), 7.31-7.27 (m, 3H), 4.79-4.64 (m, 1H), 4.38 (br s, 1H), 4.32 (br s, 1H), 4.30-4.21 (m, 2H), 3.99-3.93 (m, 1H), 3.84 (br d, J=12.2 Hz, 1H), 3.78-3.68 (m, 2H).

Preparation of Intermediate 2C

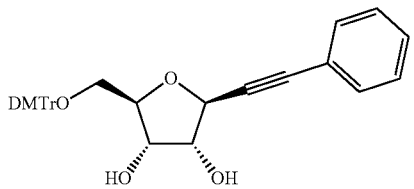

2C

To a cooled (0° C.) solution of Intermediate 2B (1.23 g, 5.25 mmol) in pyridine (12 mL) was added 4,4'-(chloro (phenyl)methylene)bis(methoxybenzene) (2.31 g, 6.83 mmol). The resulting mixture was stirred at room temperature for 1.5 h. The reaction was then quenched by adding ethanol (3 mL). The mixture was stirred for another 10 min and then concentrated in vacuo. The residue was extracted with EtOAc and washed with sat. aq. NaHCO$_3$, then brine. The organic layer was dried (Na$_2$SO$_4$), filtered, and concentrated in vacuo. The crude product was purified by flash chromatography (SiO$_2$, 80 g column [pre-treated with successive washes of 5% Et$_3$N in DCM, 100% EtOAc, and 100% hexanes], 0% to 100% EtOAc/hexanes followed by 10% MeOH/DCM) to afford Intermediate 2C (2.33 g, 4.34 mmol, 83% yield). $^1$H NMR (500 MHz, CHLOROFORM-d) δ 7.51-7.46 (m, 2H), 7.39-7.35 (m, 6H), 7.31-7.23 (m, 5H), 7.22-7.16 (m, 1H), 6.83-6.76 (m, 4H), 4.76 (d, J=4.9 Hz, 1H), 4.49-4.40 (m, 1H), 4.34-4.27 (m, 1H), 4.05 (q, J=4.6 Hz, 1H), 3.75 (s, 3H), 3.74 (s, 3H), 3.38 (dd, J=10.0, 4.7 Hz, 1H), 3.27 (dd, J=10.0, 4.1 Hz, 1H), 2.79 (br d, J=3.7 Hz, 1H), 2.54 (br d, J=3.0 Hz, 1H).

Preparation of Intermediate 2D

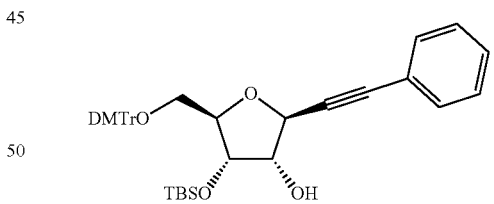

2D

To a solution of Intermediate 2C in DMF (10 mL) was added imidazole (0.609 g, 8.94 mmol) and TBSCl (0.472 g, 3.13 mmol). The reaction was stirred at room temperature overnight. The mixture was then diluted with EtOAc (30 mL), washed with sat. aq. NaHCO$_3$, brine, dried (MgSO$_4$), filtered, and concentrated in vacuo. The crude product (a mixture of 2'-OTBS and 3'-OTBS regioisomers) was dissolved in 1:1 i-PrOH/CH$_3$CN with 0.1% NH$_4$OH and purified by SFC (Chiralpak IC, 5×25 cm, 5 μm, 69:31 CO$_2$/i-PrOH:CH$_3$CN [1:1 (v/v)] with 0.1% NH$_4$OH, 280 mL/min, monitored at 236 nm) to afford Intermediate 2D (second eluting peak; 0.83 g, 1.28 mmol, 43% yield) and its regioisomer Intermediate 2D' (first eluting peak; 0.95 g, 1.46 mmol, 49% yield). Intermediate 2D (2'-OTBS regioisomer):

¹H NMR (500 MHz, CHLOROFORM-d) δ ppm −0.06 (s, 3H) 0.04 (s, 3H) 0.85 (s, 9H) 2.79 (d, J=6.24 Hz, 1H) 3.06 (dd, J=10.39, 3.79 Hz, 1H) 3.40 (dd, J=10.51, 3.30 Hz, 1H) 3.74 (s, 3H) 3.74 (s, 3H) 3.98 (q, J=3.67 Hz, 1H) 4.25-4.31 (m, 1H) 4.37 (t, J=4.89 Hz, 1H) 4.76 (d, J=4.77 Hz, 1H) 6.77 (d, J=6.24 Hz, 2H) 6.79 (d, J=6.24 Hz, 2H) 7.15-7.20 (m, 1H) 7.22-7.25 (m, 2H) 7.25-7.28 (m, 1H) 7.28 (br d, J=6.97 Hz, 1H) 7.36-7.39 (m, 2H) 7.39 (d, J=5.99 Hz, 2H) 7.41 (d, J=5.87 Hz, 2H) 7.50-7.52 (m, 2H). Intermediate 2D' (3'-OTBS regioisomer): ¹H NMR (500 MHz, CHLOROFORM-d) δ ppm 0.19 (s, 3H) 0.23 (s, 3H) 0.94 (br d, J=5.99 Hz, 1H) 2.59-2.87 (m, 1H) 3.07 (dd, J=10.33, 3.36 Hz, 1H) 3.43 (dd, J=10.27, 3.30 Hz, 1H) 3.74 (s, 3H) 3.74 (s, 3H) 4.06 (dd, J=4.95, 2.63 Hz, 1H) 4.10 (q, J=3.14 Hz, 1H) 4.62 (dd, J=6.72, 5.01 Hz, 1H) 4.65-4.71 (m, 1H) 6.78 (d, J=3.30 Hz, 2H) 6.80 (d, J=3.30 Hz, 2H) 7.15-7.20 (m, 1H) 7.22-7.27 (m, 3H) 7.27-7.30 (m, 1H) 7.29-7.32 (m, 2H) 7.36-7.40 (m, 3H) 7.39-7.41 (m, 5H) 7.41 (brd, J=2.08 Hz, 1H) 7.51 (dd, J=8.38, 1.28 Hz, 2H).

Preparation of Intermediate 2E

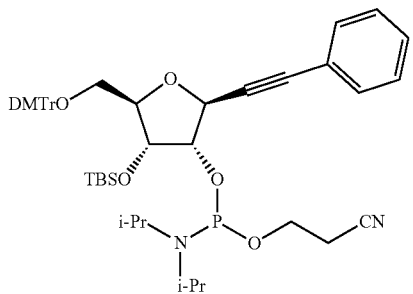

2E

To a solution of 1H-imidazole-4,5-dicarbonitrile (0.163 g, 1.383 mmol) in anhydrous DCM (7.5 mL) was added a solution of Intermediate 2D (0.9 g, 1.383 mmol) in DCM (7.5 mL), followed by dropwise addition of 3-((bis(diisopropylamino)phosphanyl)oxy)propanenitrile (0.417 g, 1.383 mmol). The resulting mixture was then stirred overnight at room temperature under a nitrogen atmosphere. The reaction was quenched with methanol (3 mL), diluted with DCM (100 mL), and washed with saturated aqueous sodium bicarbonate solution (100 mL). The organic layer was then dried (Na₂SO₄), filtered, and concentrated in vacuo. The crude product was purified by flash chromatography (SiO₂, 80 g column [pre-treated with successive washes of 5% Et₃N in DCM, 100% EtOAc, and 100% hexanes], 0% to 100% EtOAc/hexanes) to afford Intermediate 2E (0.853 g, 1.00 mmol, 72% yield) as a mixture of two diastereomers. LCMS: RT=1.29, 1.30 min. [M-(i-Pr)]⁺=807. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 2F

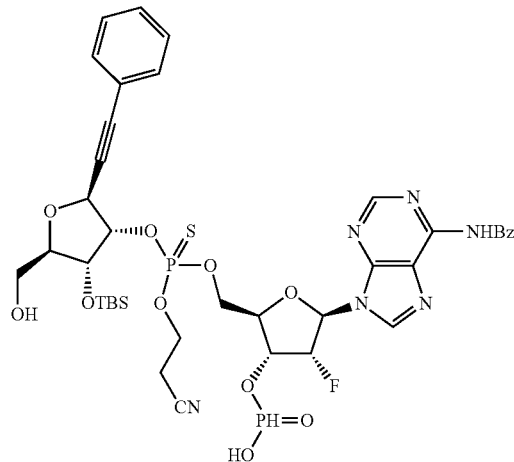

2F

Intermediate 2E (253 mg, 0.297 mmol) was azeotroped with acetonitrile (3×5 mL), leaving ~2 mL acetonitrile when evaporating the final time. Molecular sieves (4 Å, 150 mg) were added and the mixture was set aside under nitrogen atmosphere. In a separate flask, Intermediate I-1 (130 mg, 0.297 mmol) and 1H-tetrazole (62.5 mg, 0.892 mmol) were azeotroped with acetonitrile (10 mL). A stirbar was added, then the mixture was azeotroped with acetonitrile (2×10 mL), leaving ~5 mL acetonitrile when evaporating the final time. Molecular sieves (4 Å, 150 mg) were added, then the solution of Intermediate 2E prepared earlier was added via syringe. The reaction was monitored by LCMS. Upon consumption of Intermediate 2E, solid (E)-N,N-dimethyl-N'-(3-thioxo-3H-1,2,4-dithiazol-5-yl)formimidamide (DDTT) (61.0 mg, 0.297 mmol) was then added and stirring was continued for 10 min. The yellow solution was carefully concentrated in vacuo. The residue was taken up in dichloromethane and washed with 6% (m/v) aqueous sodium bicarbonate. The organic phase was then dried over Na₂SO₄, filtered, and concentrated. The crude product was purified by flash chromatography (SiO₂, 40 g RediSep Rf Gold column [pre-treated with successive washes of 5% Et₃N in DCM, 100% EtOAc, and 100% hexanes], 0 to 100% EtOAc/hexanes followed by 0 to 100% MeOH/DCM) to afford the coupled product (137 mg, 0.112 mmol, 38% yield). To a solution of the coupled product (75 mg, 0.082 mmol) and triethylsilane (0.162 mL, 1.011 mmol) in DCM (1 mL) was added dichloroacetic acid (0.028 mL, 0.337 mmol) dropwise. The solution turned a bright pink color, which gradually faded and became colorless over about one hour. The reaction was quenched with pyridine (5 mL) and stirred for 10 minutes, then concentrated in vacuo. The crude product was purified by reversed phase MPLC (C18, 50 g RediSep Rf Gold column, 0-60% acetonitrile/water containing 10 mM ammonium acetate) to afford Intermediate 2F (75 mg, 0.082 mmol, 73% yield). LCMS: RT=0.96 min. [M+H]⁺=917. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 2G

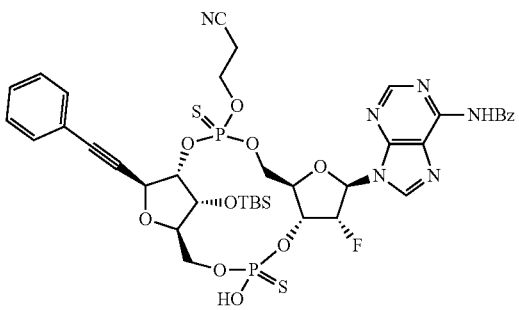

To a solution of Intermediate 2F (75 mg, 0.082 mmol; azeotroped with pyridine 3×) in pyridine (1 mL) was added a solution of 2-chloro-5,5-dimethyl-1,3,2-dioxaphosphinane 2-oxide (DMOCP) (60.4 mg, 0.327 mmol; azeotroped with pyridine 1×) in pyridine (0.5 ml). The reaction was stirred for 20 min at room temperature, then solid (E)-N,N-dimethyl-N'-(3-thioxo-3H-1,2,4-dithiazol-5-yl)formimidamide (33.6 mg, 0.164 mmol) was added. The resulting solution was stirred for 30 minutes, then 1 mL of water was added and stirring was continued for 10 min. The reaction mixture was then poured into 50 mL water containing NaHCO$_3$ (1.6 g) and stirred for 10 min. The mixture was extracted with EtOAc (3×30 mL) and the combined organic layers were concentrated and co-evaporated with toluene twice to remove residual pyridine. The crude product was dissolved in a small amount of DCM and purified by flash chromatography (SiO$_2$, 24 g RediSep Rf Gold column, 0 to 100% EtOAc/hexanes followed by 0 to 30% MeOH/DCM, 35 min gradient) to afford Intermediate 2G (69 mg, 0.074 mmol, 91% yield) as a mixture of 4 diastereomers. LCMS: RT=1.05, 1.11 min (major peaks). [M+H]$^+$=931. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 2H

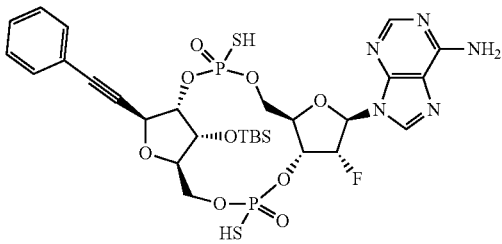

A solution of Intermediate 2G (69 mg, 0.074 mmol) in MeOH (1 mL) and conc. NH$_4$OH (1 mL) was heated in a sealed pressure vessel at 50° C. for 3 hours. The reaction vessel was cooled in an ice-water bath for 10 min before opening. The reaction mixture was transferred to a round-bottom flask and evaporated to dryness. The crude product Intermediate 2H (50 mg) was carried into the next step without further purification. LCMS: RT=0.90 min. [M+H]$^+$=774. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Examples 2-1, 2-2, 2-3, and 2-4

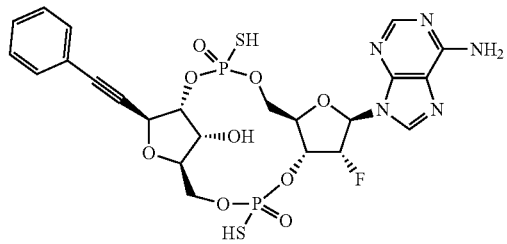

Diastereomer 1 (2-1)
Diastereomer 2 (2-2)
Diastereomer 3 (2-3)
Diastereomer 4 (2-4)

Crude Intermediate 2H (50 mg, ~0.065 mmol) was treated with pyridine (0.2 mL) and TEA.3HF (0.8 mL) at 50° C. for 5 h. The mixture was then diluted with 1M triethylammonium acetate (2 mL) (note: gas evolution) and concentrated. The crude material was purified via preparative LC/MS with the following conditions: Column: Waters Xselect RP Prep C18 OBD Column, 19 mm×150 mm, 5 μm particles; Mobile Phase A: 20 mM TEAA in water (pH 6.5); Mobile Phase B: acetonitrile; Gradient: 7-14% B over 17 minutes; Flow Rate: 20 mL/min. Fractions containing the desired product were combined and dried to afford Examples 2-1 (0.7 mg), 2-2 (1.8 mg), 2-3 (0.8 mg), and 2-4 (1.5 mg).

Example 2-1: LCMS: RT=7.69 min. [M+H]$^+$=660.

Example 2-2: LCMS: RT=7.97 min. [M+H]$^+$=660.

Example 2-3: LCMS: RT=8.37 min. [M+H]$^+$=660.

Example 2-4: LCMS: RT=8.59 min. [M+H]$^+$=660.

Column: Waters XSelect CSH C18 3.0×150 mm 3.5 μm particles; Mobile Phase A: 10 mM TEAA in water (pH 6.5); Mobile Phase B: 80:20 acetonitrile/10 mM TEAA in water (pH 6.5); Gradient: 5% B to 50% B over 15 min; Column Temperature: 25° C.; Flow: 0.5 mL/min; Detection: UV at 260 nm.

Example 3

(1R,6R,8R,9R,10R,15R,17S,18R)-8-(6-amino-9H-purin-9-yl)-9-fluoro-3,12,18-trihydroxy-17-[2-(pyridin-3-yl)ethynyl]-2,4,7,11,13,16-hexaoxa-3λ$^5$,12λ$^5$-diphosphatricyclo[13.2.1.0$^{6,10}$]octadecane-3,12-dithione

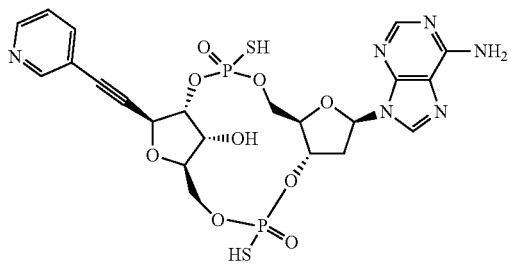

Diastereomer 1 (3-1)
Diastereomer 2 (3-2)
Diastereomer 3 (3-3)
Diastereomer 4 (3-4)

Preparation of Intermediate 3A

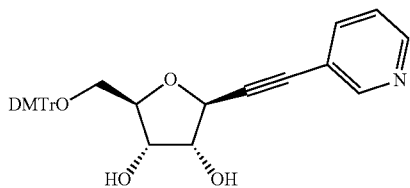

3A

To a solution of 3-iodopyridine (0.993 g, 4.84 mmol), bis(triphenylphosphine) palladium(II) dichloride (0.162 g, 0.231 mmol), and copper(I) iodide (0.044 g, 0.231 mmol) in Et$_2$NH (22 mL) was added Intermediate 1B (2.124 g, 4.61 mmol). The reaction was stirred at rt for 4d. Then, the solvent was evaporated and the crude material was dissolved in a minimal amount of CH$_2$Cl$_2$ and chromatographed. Purification by silica gel chromatography using an ISCO machine (80 g column, 60 mL/min, 0-100% EtOAc in hexanes over 24 min, t$_r$=14 min) gave Intermediate 3A (1.137 g, 2.115 mmol, 45.9% yield) as a tan foam. HPLC: RT=0.97 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=538.0 [M+H]+.

Preparation of Intermediate 3B

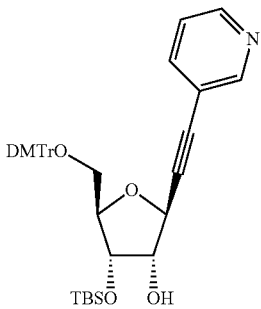

3B

To a solution of Intermediate 3A (456 mg, 0.700 mmol, 33.1% yield) in DMF (7.86 ml) was added imidazole (0.432 g, 6.34 mmol) and TBS-Cl (0.414 g, 2.75 mmol). The mixture was stirred at rt overnight. Additional TBSCl (232 mg) and imidazole (262 mg) were added. The reaction was stirred an additional 3d. The reaction was diluted with ether, washed with sat. aq. NaHCO$_3$ and brine, dried over Na$_2$SO$_4$, filtered, and concentrated to afford a yellow residue. The crude material was dissolved in a minimal amount of CH$_2$Cl$_2$ and chromatographed. Purification by silica gel chromatography using an ISCO machine (80 g column, 60 mL/min, 0-100% EtOAc in hexanes over 28 min, t$_r$=15 min) gave Intermediate 3B (388 mg, 0.595 mmol, 28.1% yield) as a colorless residue. HPLC: RT=1.35 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=652.1 [M+H]+.

Preparation of Intermediate 3C

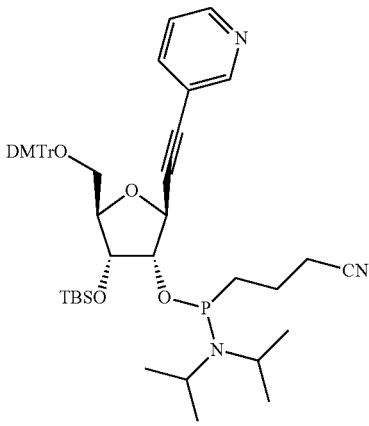

3C

To a solution of Intermediate 3B (0.244 g, 0.374 mmol) in anhydrous DCM (1.872 ml) was added 1.0 M 1H-imidazole-4,5-dicarbonitrile (0.262 ml, 0.262 mmol) in acetonitrile (syringe rinsed with 50 uL MeCN), followed by dropwise addition of 3-((bis(diisopropylamino)phosphaneyl)oxy)propanenitrile (0.271 ml, 0.898 mmol). After addition, the mixture was stirred at rt overnight. The reaction was quenched with anhydrous MeOH (1.0 mL) and stirred for 10 min. The mixture was diluted with DCM, washed with sat NaHCO$_3$, dried over Na$_2$SO$_4$, filtered and concentrated. The crude material was dissolved in a minimal amount of CH$_2$Cl$_2$ and chromatographed. An ISCO column was pre-treated with 5% Et$_3$N in 99% CH$_2$Cl$_2$, then washed successively with 100% EtOAc followed by 100% hexanes. Purification by silica gel chromatography using an ISCO machine (40 g column, 40 mL/min, 0-70% EtOAc in hexanes over 15 min, t$_r$=10.5 min) gave Intermediate 3C (130.2 mg, 0.153 mmol, 40.8% yield) as a white foam. HPLC: RT=2.52 min (Waters Acquity UPLC BEH C18, 2.1×50 mm, 1.7-μm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=852.2 [M+H]+.

Preparation of Intermediate 3D

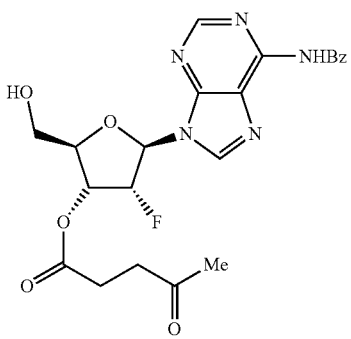

3D

N-(9-((2R,3R,4R,5R)-5-((bis(4-methoxyphenyl)(phenyl) methoxy)methyl)-3-fluoro-4-hydroxytetrahydrofuran-2-yl)-9H-purin-6-yl)benzamide (4 g, 5.92 mmol) in 10 mL of pyridine was added 4-oxopentanoic anhydride (1.268 g, 5.92 mmol), followed by a catalytic amount of DMAP (40 mg). The reaction was stirred at rt for 2h, then the reaction was concentrated. The residue was dissolved in 50 mL of EtOAc, washed with sat. aq. NaHCO$_3$, sat. aq. NaCl, dried over Na$_2$SO$_4$, filtered, and concentrated. The crude material was dissolved in 20 mL of DCM, then 2,2-dichloroacetic acid (3.82 g, 29.6 mmol) was added. After 30 min, the reaction was diluted with 30 mL of DCM and washed with sat. aq. NaHCO$_3$. The aqueous phase was extracted with 30 mL of DCM (2×). The combined organic layers were dried over Na$_2$SO$_4$, filtered, then concentrated. Purification by silica gel chromatography using an ISCO machine (0-5% MeOH/DCM) gave Intermediate 3D (2.52 g, 5.35 mmol, 90% yield) as a white solid. 1H NMR (499 MHz, CHLOROFORM-d) δ 9.04 (s, 1H), 8.82 (s, 1H), 8.16 (s, 1H), 8.08-7.99 (m, 2H), 7.65 (m, 1H), 7.57 (d, J=7.9 Hz, 2H), 6.21 (dd, J=11.9, 6.7 Hz, 1H), 6.02-5.84 (m, 1H), 5.82-5.75 (m, 1H), 5.73-5.64 (m, 1H), 4.44 (t, J=1.5 Hz, 1H), 4.01 (br d, J=12.9 Hz, 1H), 3.85 (s, 1H), 2.97-2.63 (m, 4H), 2.25 (s, 3H).

Preparation of Intermediate 3E

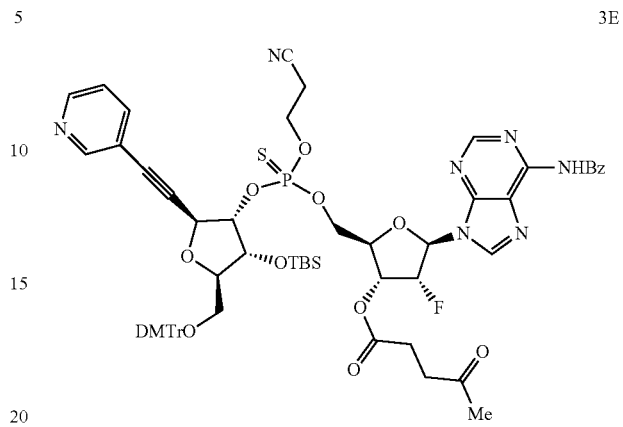

3E

To a solution of Intermediate 3C (86 mg, 0.183 mmol) (azeotroped 2× with ACN) and tetrazole (12.85 mg, 0.183 mmol) in acetonitrile (1.0 mL) was added 4A MS (30 mg) followed by Intermediate 3D (130.2 mg, 0.153 mmol) in acetonitrile (0.3 mL). The syringe was rinsed with additional acetonitrile (0.3 mL). The reaction was allowed to stir at rt for 3 h, then quenched with (E)-N,N-dimethyl-N'-(3-thioxo-3H-1,2,4-dithiazol-5-yl)formimidamide (37.6 mg, 0.183 mmol). The crude material was dissolved in a minimal amount of CH$_2$Cl$_2$ and chromatographed. Purification by silica gel chromatography using an ISCO machine (40 g column, 40 mL/min, 0-20% MeOH in CH$_2$Cl$_2$ over 11 min, t$_r$=6.5 min) gave Intermediate 3E (192 mg, 0.153 mmol, 100% yield) as a yellow solid.

Preparation of Intermediate 3F

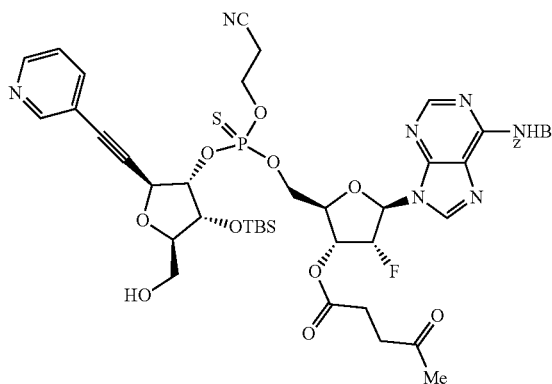

3F

In a 10 mL round bottom flask was added Intermediate 3E (192 mg, 0.153 mmol) in CH$_2$Cl$_2$ (1531 μl), then 2,2-dichloroacetic acid (60.9 μl, 0.765 mmol) was added. The reaction was stirred at rt for 4 h. Additional DCA (80 uL) was added. The reaction was quenched with triethylsilane (122 μl, 0.765 mmol) and pyridine (495 μl, 6.12 mmol), then concentrated in vacuo (water bath 34° C.). The resultant residue was azeotroped with CH$_3$CN (2×1 mL). The crude material was chromatographed, then re-subjected to the reaction conditions again. This time the reaction was allowed to run longer (~4h). The crude material was dissolved in a minimal amount of CH$_2$Cl$_2$ and chromatographed. Purification by silica gel chromatography using an ISCO machine (40 g column, 40 mL/min, 0-50% MeOH in CH$_2$Cl$_2$ over 14 min, t$_r$=9 min) gave Intermediate 3F (146 mg, 0.153 mmol, 100% yield) as a yellow solid.

Preparation of Intermediate 3G

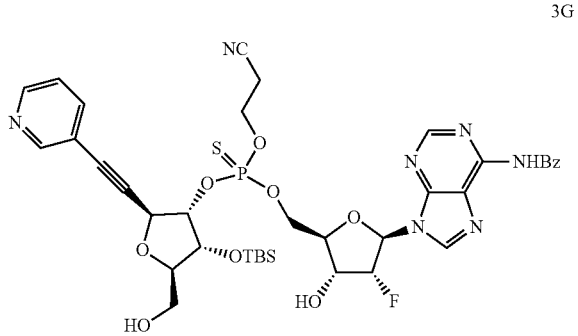

3G

Intermediate 3F (146 mg, 0.153 mmol) was treated with 0.5 M hydrazine monohydrate in a mixture of 3:2 pyridine:acetic acid (0.92 mL of 3:2 pyridine/acetic acid containing 9.7 uL or 3.0 equiv of hydrazine hydrate) The reaction was stirred at rt for 30 min. Acetylacetone (31.5 µl, 0.307 mmol) was added to quench unreacted hydrazine hydrate. The reaction was concentrated under high vacuum overnight, then dried onto Celite with minimal CH$_2$Cl$_2$. Purification using a reverse phase ISCO machine (50 g GOLD column, 40 mL/min, 0-100% ACN in H$_2$O+NH$_4$OAc over 21 min, t$_r$=15 min) gave Intermediate 3G (36.9 mg, 0.043 mmol, 28.2% yield) as a white solid after lyophilization for 2 d. HPLC: RT=0.94 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=854.1 [M+H]+.

Preparation of Intermediates 3H, 3I, 3J, and 3K

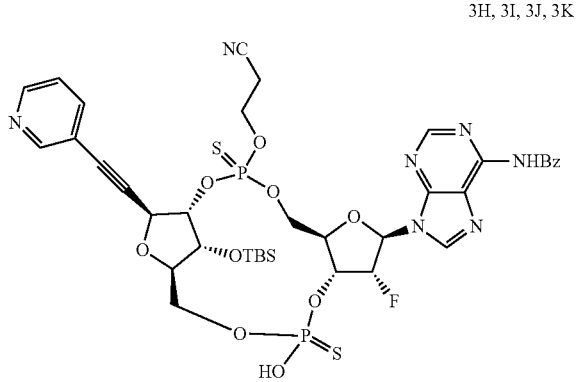

3H, 3I, 3J, 3K

Intermediate 3G (20.4 mg, 0.024 mmol) was azeotroped in pyridine (2×), then pyridine (4077 µl) was added. To this solution was added a solution of diphenyl phosphonate (5.99 µl, 0.031 mmol) in one portion. After 1 h, additional diphenyl phosphite (3 uL) was added. (E)-N,N-dimethyl-N'-(3-thioxo-3H-1,2,4-dithiazol-5-yl)formimidamide (14.71 mg, 0.072 mmol) was added and the reaction was allowed to stir at rt overnight. The solvent was evaporated and the crude material was purified by chromatography. Purification using a reverse phase ISCO machine (50 g GOLD column, 40 mL/min, 0-100% ACN in H2O+NH$_4$OAc over 16 min, t$_r$=11, 13, 13.5 min) gave Intermediate 3H (10.5 mg, 47% yield), a mixture of Intermediates 3I and 3J (7.9 mg), and Intermediate 3K (6.3 mg, 28%) which were all obtained as white solids after lyophilization for 2 d. Intermediates 3I and 3J were separated by preparative SFC with the following conditions: Column: Chiral OD, 30×250 mm. 5-µm particles; Mobile Phase A: 75% CO2/25% MeOH w/0.1% DEA; Detector Wavelength: 220 nm; Flow: 100 mL/min. The fractions ("Peak-1" t$_r$=19.5 min, and "Peak-2" t$_r$=22.5 min; analytical conditions: Column: Chiralpak OD, 4.6×100 mm, 5-µm particles; Mobile Phase A: 75% CO2/25% MeOH w/0.1% DEA; Flow: 2.0 mL/min) were collected in MeOH. The stereoisomeric purity of each fraction was estimated to be greater than 95% (Peak-1, Intermediate 3I) and 95% (Peak-2, Intermediate 3J) based on the prep-SFC chromatograms.

Intermediate 3H: 10.5 mg, 47% yield, HPLC: RT=0.85 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=932.1 [M+H]+.

Intermediate 3I: 2.8 mg, 13% yield; HPLC: RT=0.88 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=932.0 [M+H]+.

Intermediate 3J: 1.9 mg, 9% yield; HPLC: RT=0.90 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=932.1 [M+H]+.

Intermediate 3K: 6.3 mg, 28%; HPLC: RT=0.94 min (Waters Acquity UPLC BEH C18, 2.1×50 mm, 1.7-µm particles; Mobile Phase A: 95:5% water:acetonitrile with 0.01M Ammonium Acetate; Mobile Phase B: 95:5% acetonitrile:water with 0.01M Ammonium Acetate; Temperature: 50° C.; Gradient: 5-95% B over 1 minute, then 95-5% B over 0.5 minute; Flow: 0.8 mL/min.); MS (ES): m/z=932.2 [M+H]+.

Preparation of Intermediate 3L

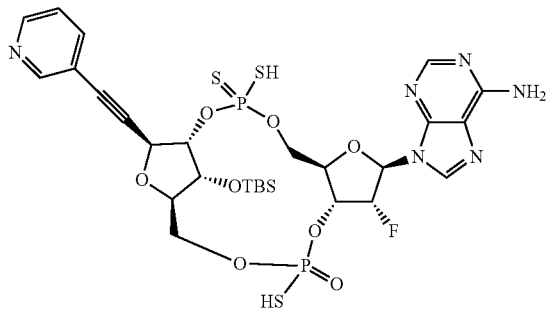
3L

In a 5 dram vial, Intermediate 31 (2.8 mg, 3.00 µmol) was dissolved in MeOH in ammonia (344 µl, 2.410 mmol). The reaction was stirred at rt overnight, then the solvent was evaporated to afford Intermediate 3L, which was carried forward without further purification. HPLC: RT=0.70 min (Waters Acquity UPLC BEH C18, 2.1×50 mm, 1.7 µm particles; Mobile Phase A: water with 0.05% TFA; Mobile Phase B: acetonitrile with 0.05% TFA; Temperature: 50° C.; Gradient: 2-98% B over 1 minute, then 98-2% B over 0.5 min; Flow: 0.8 mL/min.); MS (ES): m/z=775.4 [M+H]$^+$. Absolute stereochemistry not determined.

Preparation of Example 3-1

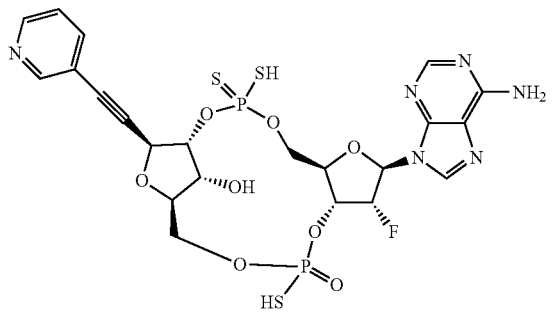
Example 3-1

A solution of Intermediate 3L (2.3 mg, 2.97 µmol) in neat triethylamine trihydrofluoride (4.48 µl, 0.027 mmol) was heated at 37° C. (300 uL) for 1 h, then allowed to cool to rt. The reaction was neutralized with an aqueous solution of 4N ammonium acetate buffer until ~pH 6.5 (2 mL). The aqueous phase was concentrated and dried under high vacuum overnight (to fully remove water) to afford a white solid. The solid was suspended in $CH_2Cl_2$ and MeOH, then filtered and washed with $CH_2Cl_2$ and MeOH. The filtrate was concentrated. The crude material was purified via via preparative LC/MS with the following conditions: Column: Agilent Bonus RP C18 2.6 uM, 200 mm×21.2 mm, 5-µm particles; Mobile Phase A: 5:95 acetonitrile:water with ammonium acetate; Mobile Phase B: 95:5 acetonitrile:water with ammonium acetate; Gradient: a 6-minute hold at 0% B, 0-25% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford Example 3-1 (1.5 mg, 76%). HPLC: RT=0.38 min (Waters Acquity UPLC BEH C18, 2.1×50 mm, 1.7-µm particles; Mobile Phase A: water with 0.05% TFA; Mobile Phase B: acetonitrile with 0.05% TFA; Temperature: 50° C.; Gradient: 2-98% B over 1 minute, then 98-2% B over 0.5 min; Flow: 0.8 mL/min.); MS (ES): m/z=661.2 [M+H]$^+$. Absolute stereochemistry not determined.

Examples 3-2, 3-3 and 3-3 were prepared according the procedures described for Example 3-1, from Intermediates 3J, 3K, and 3H, respectively.

Example 3-2 (1.3 mg). HPLC: RT=0.37 min (Waters Acquity UPLC BEH C18, 2.1×50 mm, 1.7-µm particles; Mobile Phase A: water with 0.05% TFA; Mobile Phase B: acetonitrile with 0.05% TFA; Temperature: 50° C.; Gradient: 2-98% B over 1 minute, then 98-2% B over 0.5 min; Flow: 0.8 mL/min.); MS (ES): m/z=661.3 [M+H]+.

Example 3-3 (3.1 mg). HPLC: RT=0.41 min (Waters Acquity UPLC BEH C18, 2.1×50 mm, 1.7-µm particles; Mobile Phase A: water with 0.05% TFA; Mobile Phase B: acetonitrile with 0.05% TFA; Temperature: 50° C.; Gradient: 2-98% B over 1 minute, then 98-2% B over 0.5 min; Flow: 0.8 mL/min.); MS (ES): m/z=661.2 [M+H]+.

Example 3-4 (0.9 mg). HPLC: RT=0.31 min (Waters Acquity UPLC BEH C18, 2.1×50 mm, 1.7-µm particles; Mobile Phase A: water with 0.05% TFA; Mobile Phase B: acetonitrile with 0.05% TFA; Temperature: 50° C.; Gradient: 2-98% B over 1 minute, then 98-2% B over 0.5 min; Flow: 0.8 mL/min.); MS (ES): m/z=661.3 [M+H]+.

Evaluation of Biological Activity

STING THP1 Reporter Assay Protocol

THP1-Dual™ cells were derived from the human THP-1 monocyte cell line by stable integration of two inducible reporter constructs. To this end, THP1-Dual™ cells allow the simultaneous study of the NF-κB pathway, by monitoring the activity of SEAP, and the IRF pathway by assessing the activity of a secreted luciferase (Lucia). Both reporter proteins are readily measurable in the cell culture supernatant when using QUANTI-Blue™, a SEAP detection reagent, and QUANTI-Luc™, a luciferase detection reagent.

THP1-Dual™ cells induce the activation of NF-κB in response to STING agonists. They also trigger the IRF pathway upon stimulation with STING agonists, such as cGAMP. Here, the THP-1-Dual cells were used to assess STING binders for function on the cellular level.

Serial dilutions of compounds in DMSO were added to low volume 384 well plates at 100 nl/well using an ECHO acoustic dispenser (Labcyte, model 550) to achieve final starting concentration of 100 µM in cell suspension. THP-1 Dual™ STING reporter cells (Invivogen, Dual cells cat #THPD-nfis) were added to the plates with compounds at 15,000 cells in 10 µL per well in RPMI media (Gibco, cat #11875) containing 10% human plasma in a low volume 384-well black wall clear bottom tissue culture plate (Corning, cat #3542) for SEAP assay and low volume solid white plate (Corning, cat #3826) for luciferase assay. One column of the plate was reserved for treatment with cGAMP at 100 µM for 100% activation calculation and one column for no treatment (DMSO only) for baseline activation. Plates were then incubated in 37° C. incubator at 5% $CO_2$ for 20 hours.

In the SEAP assay, 5 µl of 2× QuantiBlue (Invivogen, cat #Rep-qb2) is added to 384 well black plates seeded with THP1 cells and incubated at 37° C. for 2 hours. Plates were read on the Envision (Perkin Elmer) at 620 nm wavelength (OD620). In the luciferase assay, 5 μl of Quantiluc (Invivogen, Rep-qlc2) is added to white 384 well plates seeded with THP1 cells and read at 5 minutes on the Envision (Perkin Elmer) using a luminescence protocol (RLU). For both cell lines, 100% activation was determined by value (RLU) of THP-1 Dual STING cells stimulated with 100 μM cGAMP (Invivogen, cat #TLRL-NACGA23-5).

STING HTRF Binding Assays

A time resolved FRET-based competition binding assay was used to assess test article binding to STING WT and STING AQ. His-tagged STING cytoplasmic domain (WT or AQ) at a concentration of 20 nM was incubated with 2.5 nM Tb-labeled anti-His antibody, test compound, and fluorescein-labeled cGAMP analog probe (BioLog cat. no. C195) at a concentration of 200 nM (STING WT) or 40 nM (STING AQ) in PBS containing 0.005% Tween-20 and 0.1% BSA for one hour. Fluorescence at 495 nm and 520 nm was measured using an EnVision microplate reader to quantify FRET between Tb-labeled anti-His antibody and fluorescein-labeled probe. Background was defined as the signal obtained in the absence of STING protein, and background subtracted FRET ratios were normalized to the maximum signal obtained in the absence of test compound. These values were converted to a percent inhibition. Percent inhibition was determined for test compounds at 11 concentrations. The $IC_{50}$, defined as the concentration of competing test compound needed to reduce specific binding of the probe by 50%, was calculated using the 4 parameter logistic equation to fit the data

```
STING WT: His-TVMV-S-hSTING(155-341)-H232R
                                     (SEQ ID NO. 1)
MGSSHHHHHHSSGETVRFQGHMSVAHGLAWSYYIGYLRLILPELQARIRT

YNQHYNNLLRGAVSQRLYILLPLDCGVPDNLSMADPNIRFLDKLPQQTGD
```

-continued

```
RAGIKDRVYSNSIYELLENGQRAGTCVLEYATPLQTLFANISQYSQAGFSR

EDRLEQAKLFCRTLEDILADAPESQNNCRLIAYQEPADDSSFSLSQEVLRH

LRQEEKEEV

STING AQ: His-TVMV-S-hSTING(155-341)-G230A-R293Q
                                     (SEQ ID NO. 2)
MGSSHHHHHHSSGETVRFQGHMSVAHGLAWSYYIGYLRLILPELQARIRT

YNQHYNNLLRGAVSQRLYILLPLDCGVPDNLSMADPNIRFLDKLPQQTAD

RAGIKDRVYSNSIYELLENGQRAGTCVLEYATPLQTLFANISQYSQAGFSR

EDRLEQAKLFCQTLEDILADAPESQNNCRLIAYQEPADDSSFSLSQEVLRH

LRQEEKEEV
```

| | THP1 Reporter Assays | | HTRF Binding Assays $IC_{50}$ (μM) | |
|---|---|---|---|---|
| | $EC_{50}$ (μM) | | STING | STING |
| Example # | IRF3 | NFkB | WT | AQ |
| Example 1-1 | 23 | 37 | 1.4 | 0.06 |
| Example 1-2) | 24 | 42 | 1.7 | 0.03 |
| Example 1-3 | >100 | >100 | 55.3 | 1.9 |
| Example 2-1) | >100 | >100 | >100 | 19.4 |
| Example 2-2 | >100 | >100 | 9.6 | 0.5 |
| Example 2-3 | >100 | >100 | 20.5 | 0.7 |
| Example 2-4 | >100 | >100 | >100 | 17.0 |
| Example 3-1 | >100 | >100 | 67.4 | 1.3 |
| Example 3-2 | >100 | >100 | 3.4 | 0.2 |
| Example 3-3 | 6.0 | 8.1 | 1.1 | 0.04 |
| Example 3-4 | >100 | >100 | 29.6 | 1.4 |

We claim:

1. A compound of the formula

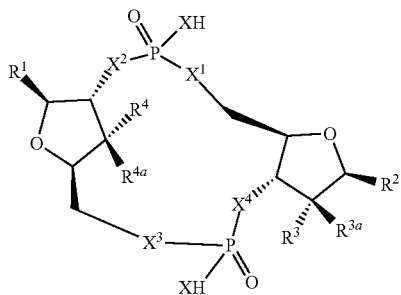
(I)

wherein
each X is independently O or S;
$X^1$, $X^2$, $X^3$ and $X^4$ are each independently O or NH;
$R^1$ and $R^2$ are independently

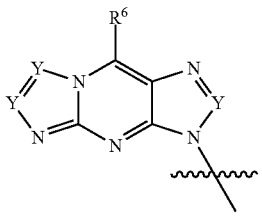 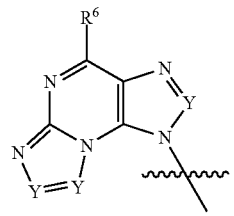

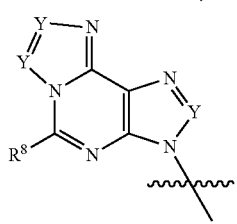 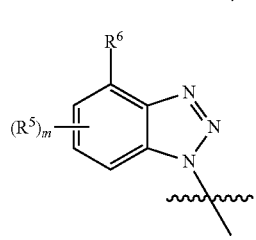

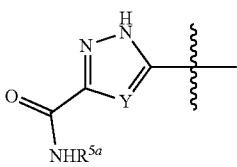 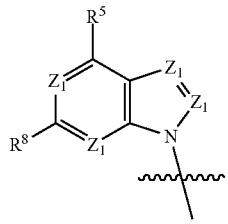

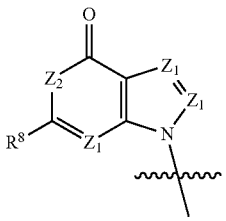 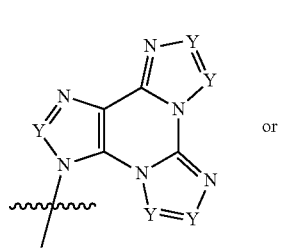 or

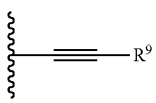

with the proviso that one of $R^1$ and $R^2$ must be

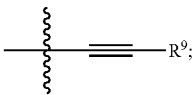

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $—C(O)R^{a1}$, $—C(O)NR^{a1}R^{a1}$, $—S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2 R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2 R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2 R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

m is 0, 1, 2 or 3;

or a pharmaceutically acceptable salt, tautomer or stereoisomer thereof.

2. The compound according to claim 1 wherein

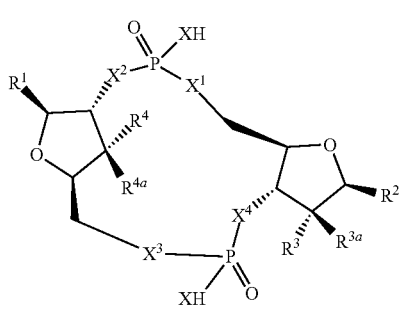
(I)

wherein
each X is independently O or S;
$X^1$, $X^2$, $X^3$ and $X^4$ are each independently O or NH;
$R^1$ and $R^2$ are independently

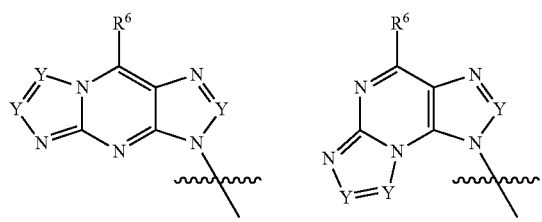

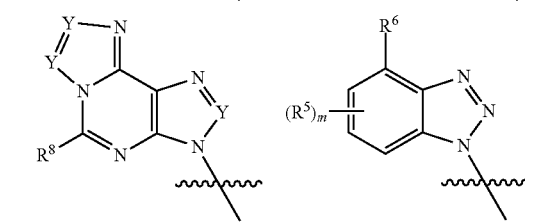

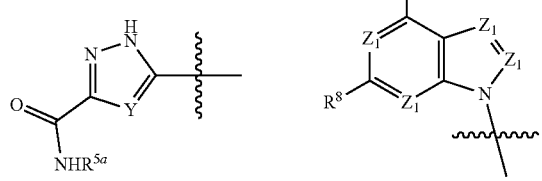

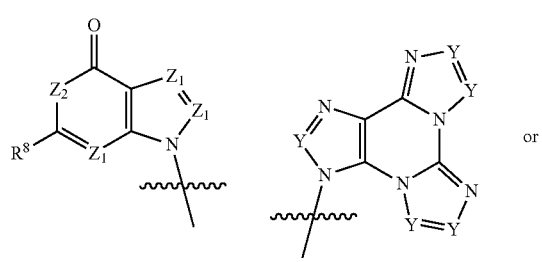 or

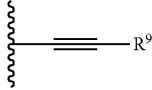

with the proviso that one of $R^1$ and $R^2$ must be

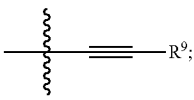

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $—C(O)R^{a1}$, $—C(O)NR^{a1}R^{a1}$, $—S(O)_2R^{a1}$ or $S(O)_2NR^{a1}R^{a1}$;

$R^{a1}$ is H or $C_{1-3}$ alkyl substituted with 0-6 $R^5$;

$R^3$ is H, $CH_3$, and halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

3. The compound according to claim 1 of the formula

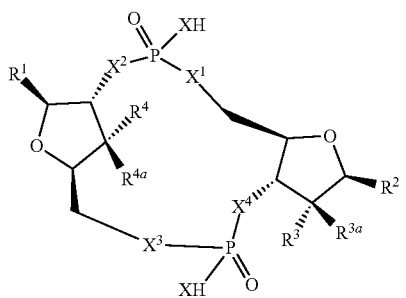 (I)

wherein
X is S;
$X^1$, $X^2$, $X^3$ and $X^4$ are each independently O or NH;
$R^1$ and $R^2$ are independently

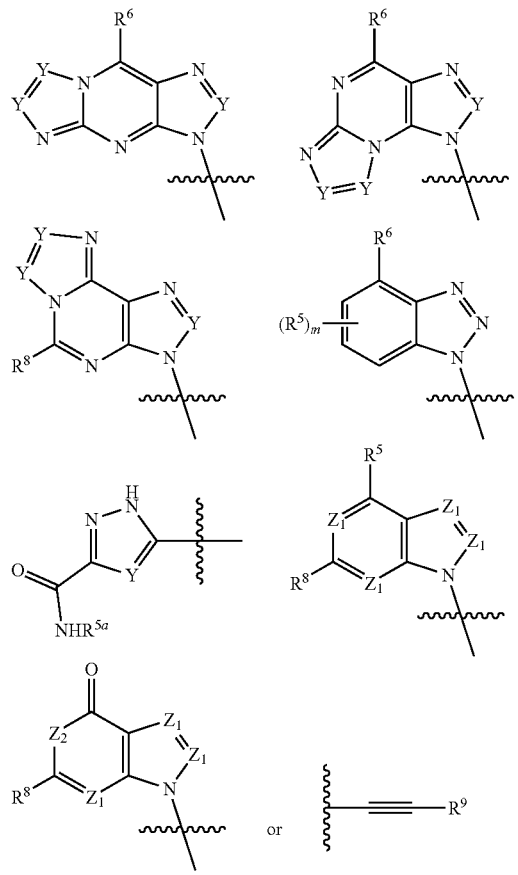

with the proviso that one of $R^1$ and $R^2$ must be

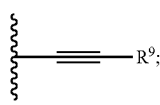

$Z^1$ is N or $CR^a$;
$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ is H, $CH_3$, and halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

4. The compound according to claim 1 of the formula

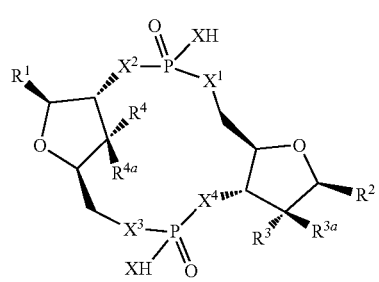 (I)

wherein
X is O;
$X^1$, $X^2$, $X^3$ and $X^4$ are each independently O or NH;

107

R¹ and R² are independently

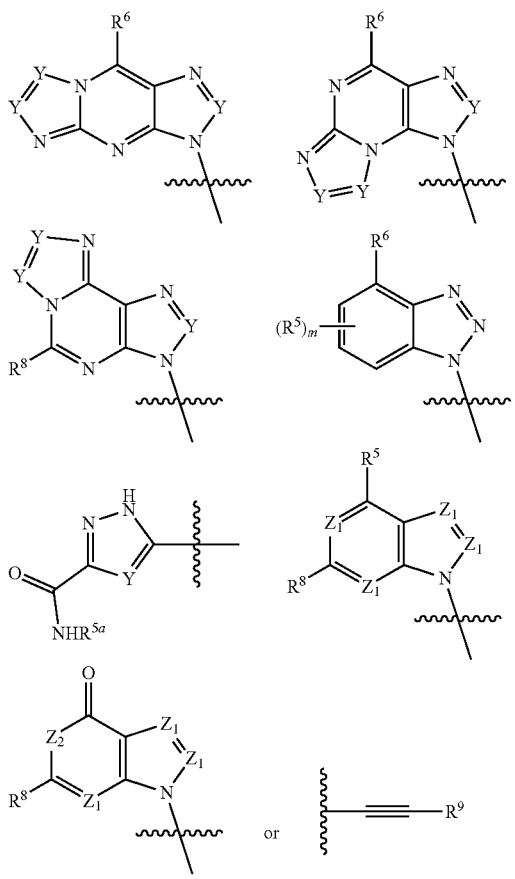

with the proviso that one of R¹ and R² must be

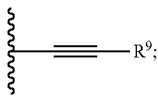

Z¹ is N or CR$^a$;
Z² is NR$^b$;
R$^a$ is H, halogen, C$_{1-6}$ alkyl substituted with 0-6 R⁵, C$_{3-6}$ cycloalkyl substituted with 0-6 R⁵, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R⁵, C$_{3-6}$ cycloalkyl substituted with 0-6 R⁵, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H or C$_{1-3}$ alkyl substituted with 0-6 R⁵;
R³ is H, CH$_3$, and halogen, NH$_2$ or OH;
R$^{3a}$ is H, CH$_3$, halogen, NH$_2$ or OH; or
R³ and R$^{3a}$ may be taken together to form a 3-4 membered carbocycle; or
R³ and R$^{3a}$ may be taken together to form a C=CH$_2$ substituent;
R⁵ is H, halogen, C$_{1-3}$ alkyl substituted with 0-6 R$^a$, C$_{3-6}$ cycloalkyl substituted with 0-6 R$^a$, aryl substi-

108 tuted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R⁵;

R⁶ is H, halogen, C$_{1-3}$ alkyl substituted with 0-6 R⁵, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R⁸ is H, halogen, C$_{1-3}$ alkyl substituted with 0-6 R⁵, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R⁹ is H, C$_{1-6}$ alkyl substituted with 0-6 R⁵, C$_{3-6}$ cycloalkyl substituted with 0-6 R⁵, aryl substituted with 0-6 R⁵ or heteroaryl substituted with 0-6 R⁵;

Y is CR⁵ or N;

or a pharmaceutically acceptable salt, tautomer or stereoisomer thereof.

5. The compound according to claim 1 of the formula

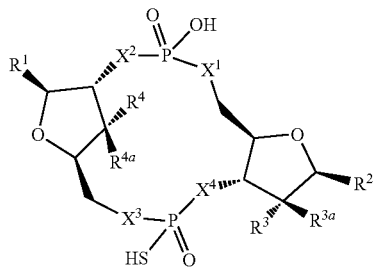

wherein

X¹, X², X³ and X⁴ are each independently O or NH;

R¹ and R² are independently

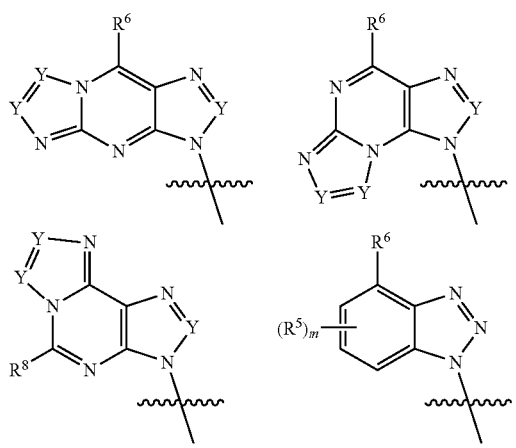

-continued

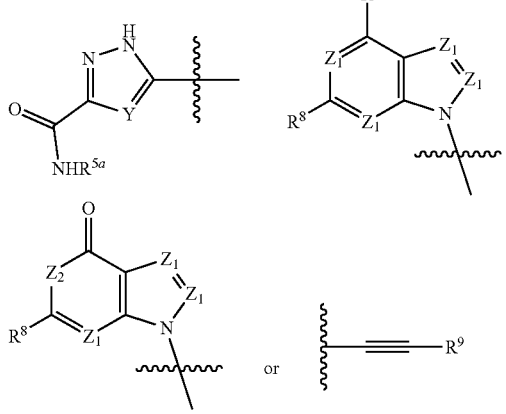

with the proviso that one of $R^1$ and $R^2$ must be

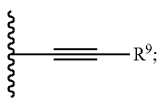

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl substituted with 0-6 $R^5$;
$R^3$ is H, $CH_3$, and halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

6. The compound according to claim 1 of the formula

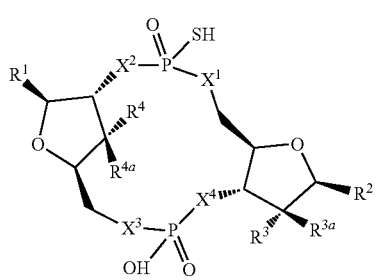

wherein $X^1$, $X^2$, $X^3$ and $X^4$ are each independently O or NH;

$R^1$ and $R^2$ are independently

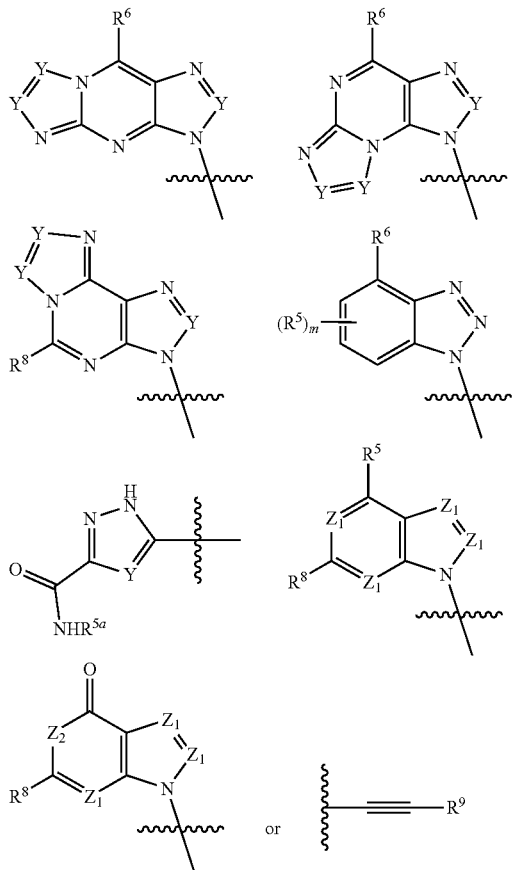

with the proviso that one of $R^1$ and $R^2$ must be

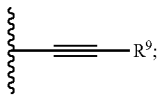

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl substituted with 0-6 $R^5$;

$R^3$ is H, $CH_3$, and halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

7. The compound according to claim 1 of the formula

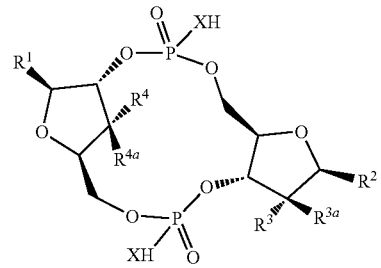

wherein
each X is independently O or S;
$R^1$ and $R^2$ are independently

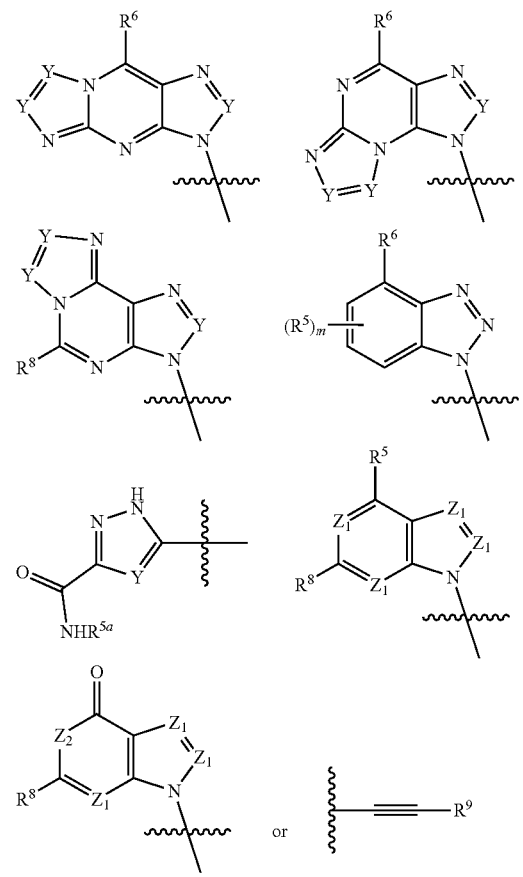

with the proviso that one of $R^1$ and $R^2$ must be

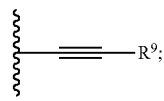

$Z^1$ is N or $CR^a$;

$Z^2$ is NR;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, —NR$^{a1}$C(O)R$^{a1}$, —NR$^{a1}$COOR$^{a1}$, —NR$^{a1}$C(O) NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ is H, CH$_3$, and halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, C$_{1-6}$ alkyl substituted with 0-6 R$^5$, C$_{3-6}$ cycloalkyl substituted with 0-6 R$^5$, aryl substituted with 0-6 R$^5$ or heteroaryl substituted with 0-6 R$^5$;

Y is CR$^5$ or N;

or a pharmaceutically acceptable salt, tautomer or stereoisomer thereof.

8. The compound according to claim 1 of the formula

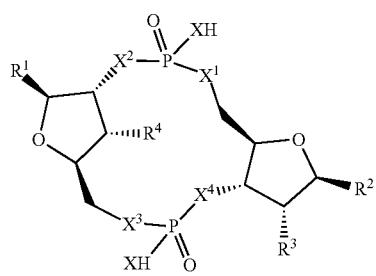

wherein each X is independently O or S;

X$^1$, X$^2$, X$^3$ and X$^4$ are each independently O or NH;

R$^1$ and R$^2$ are independently

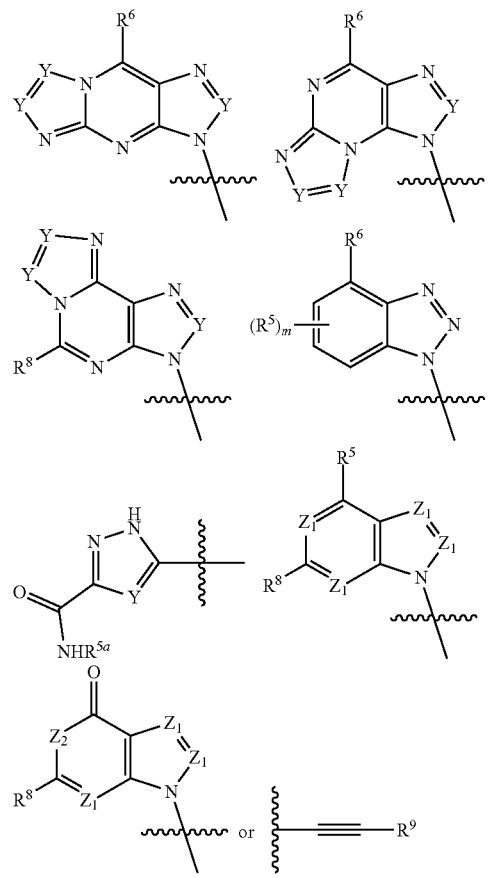

with the proviso that one of R$^1$ and R$^2$ must be

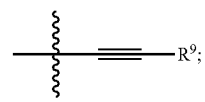

Z$^1$ is N or CR$^a$;

Z$^2$ is NR;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O) NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O) NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^4$ are independently H, CH$_3$, halogen, NH$_2$ or OH;

R$^5$ is H, halogen, C$_{1-3}$ alkyl substituted with 0-6 R$^a$, C$_{3-6}$ cycloalkyl substituted with 0-6 R$^a$, aryl substituted with 0-6 R$^a$ or heteroaryl substituted with 0-6 R$^a$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2 R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2 R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;

or a pharmaceutically acceptable salt, tautomer or stereoisomer thereof.

9. The compound according to claim 1 of the formula

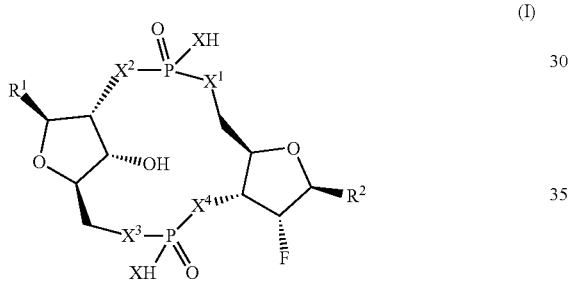

(I)

wherein

X is S;

$X^1$, $X^2$, $X^3$ and $X^4$ are each independently O or NH;

$R^1$ and $R^2$ are independently

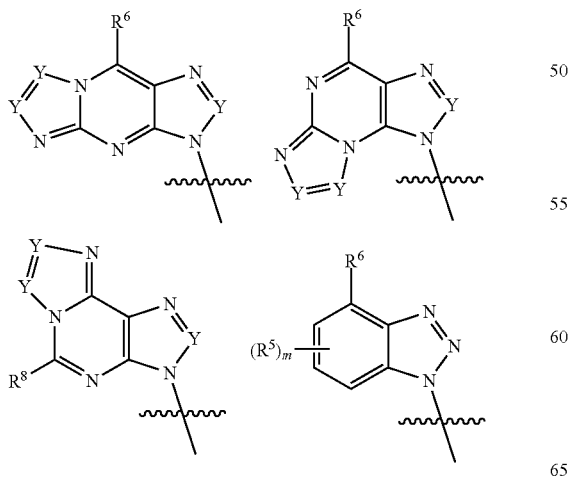

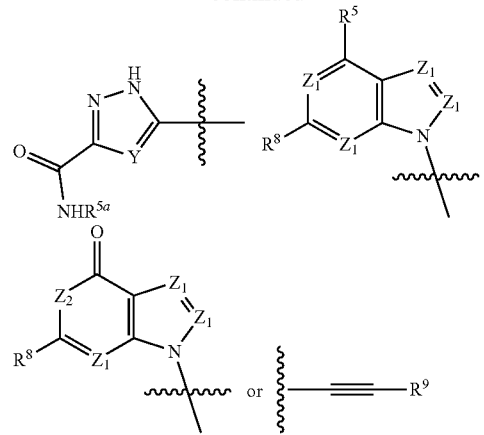

with the proviso that one of $R^1$ and $R^2$ must be

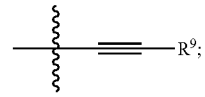

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2 R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2 R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2 R^{a1}$ or $S(O)_2NR^{a1}R^{a1}$;

$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is CR⁵ or N;
or a pharmaceutically acceptable salt, tautomer or stereoisomer thereof.

10. The compound according to claim 1 of the formula

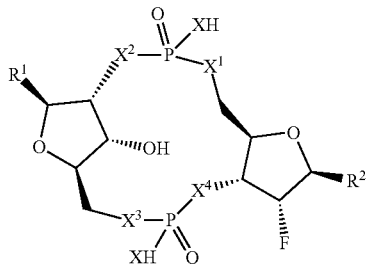

wherein
X is O;
X¹, X², X³ and X⁴ are each independently O or NH;
R¹ and R² are independently

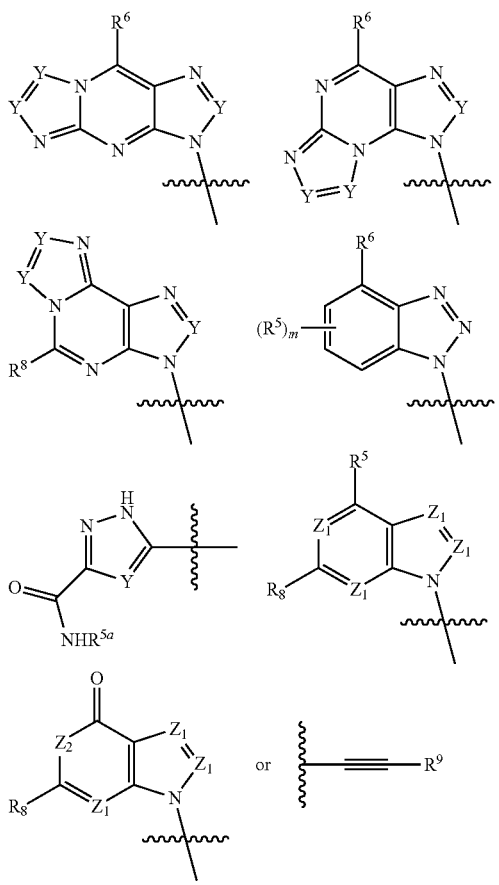

with the proviso that one of R¹ and R² must be

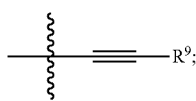

Z¹ is N or CRᵃ;
Z² is NRᵇ;
Rᵃ is H, halogen, C₁₋₆ alkyl substituted with 0-6 R⁵, C₃₋₆ cycloalkyl substituted with 0-6 R⁵, CN, NO₂, OH, ORᵃ¹, SRᵃ¹, —C(O)NRᵃ¹Rᵃ¹, —COORᵃ¹, —OC(O)Rᵃ¹, —OC(O)NRᵃ¹Rᵃ¹, —NRᵃ¹Rᵃ¹, —NRᵃ¹C(O)Rᵃ¹, —NRᵃ¹COORᵃ¹, —NRᵃ¹C(O)NRᵃ¹Rᵃ¹, —NRᵃ¹S(O)₂Rᵃ¹, —NRᵃ¹S(O)₂NRᵃ¹Rᵃ¹, —S(O)Rᵃ¹, —S(O)NRᵃ¹Rᵃ¹, —S(O)₂Rᵃ¹ or S(O)₂NRᵃ¹Rᵃ¹;
Rᵇ is H, C₁₋₆ alkyl substituted with 0-6 R⁵, C₃₋₆ cycloalkyl substituted with 0-6 R⁵, —C(O)Rᵃ¹, —C(O)NRᵃ¹Rᵃ¹, —S(O)₂Rᵃ¹ or S(O)₂NRᵃ¹Rᵃ¹;
Rᵃ¹ is H or C₁₋₃ alkyl substituted with 0-6 R⁵;
R⁵ is H, halogen, C₁₋₃ alkyl substituted with 0-6 Rᵃ, C₃₋₆ cycloalkyl substituted with 0-6 Rᵃ, aryl substituted with 0-6 Rᵃ or heteroaryl substituted with 0-6 Rᵃ, CN, NO₂, OH, ORᵃ¹, SRᵃ¹, —C(O)NRᵃ¹Rᵃ¹, —COORᵃ¹, —OC(O)Rᵃ¹, —OC(O)NRᵃ¹Rᵃ¹, —NRᵃ¹Rᵃ¹, —NRᵃ¹C(O)Rᵃ¹, —NRᵃ¹COORᵃ¹, —NRᵃ¹C(O)NRᵃ¹Rᵃ¹, —NRᵃ¹S(O)₂Rᵃ¹, —NRᵃ¹S(O)₂NRᵃ¹Rᵃ¹, —S(O)Rᵃ¹, —S(O)NRᵃ¹Rᵃ¹, —S(O)₂Rᵃ¹ or S(O)₂NRᵃ¹Rᵃ¹;
R⁵ᵃ is H or C₁₋₃ alkyl substituted with 0-6 R⁵;
R⁶ is H, halogen, C₁₋₃ alkyl substituted with 0-6 R⁵, CN, NO₂, OH, ORᵃ¹, SRᵃ¹, —C(O)NRᵃ¹Rᵃ¹, —COORᵃ¹, —OC(O)Rᵃ¹, —OC(O)NRᵃ¹Rᵃ¹, —NRᵃ¹Rᵃ¹, —NRᵃ¹C(O)Rᵃ¹, —NRᵃ¹COORᵃ¹, —NRᵃ¹C(O)NRᵃ¹Rᵃ¹, —NRᵃ¹S(O)₂Rᵃ¹, —NRᵃ¹S(O)₂NRᵃ¹Rᵃ¹, —S(O)Rᵃ¹, —S(O)NRᵃ¹Rᵃ¹, —S(O)₂Rᵃ¹ or S(O)₂NRᵃ¹Rᵃ¹;
R⁸ is H, halogen, C₁₋₃ alkyl substituted with 0-6 R⁵, CN, NO₂, OH, ORᵃ¹, SRᵃ¹, —C(O)NRᵃ¹Rᵃ¹, —COORᵃ¹, —OC(O)Rᵃ¹, —OC(O)NRᵃ¹Rᵃ¹, —NRᵃ¹Rᵃ¹, —NRᵃ¹C(O)Rᵃ¹, —NRᵃ¹COORᵃ¹, —NRᵃ¹C(O)NRᵃ¹Rᵃ¹, —NRᵃ¹S(O)₂Rᵃ¹, —NRᵃ¹S(O)₂NRᵃ¹Rᵃ¹, —S(O)Rᵃ¹, —S(O)NRᵃ¹Rᵃ¹, —S(O)₂Rᵃ¹ or S(O)₂NRᵃ¹Rᵃ¹;
R⁹ is H, C₁₋₆ alkyl substituted with 0-6 R⁵, C₃₋₆ cycloalkyl substituted with 0-6 R⁵, aryl substituted with 0-6 R⁵ or heteroaryl substituted with 0-6 R⁵;
Y is CR⁵ or N;
or a pharmaceutically acceptable salt, tautomer or stereoisomer thereof.

11. The compound according to claim 1 of the formula

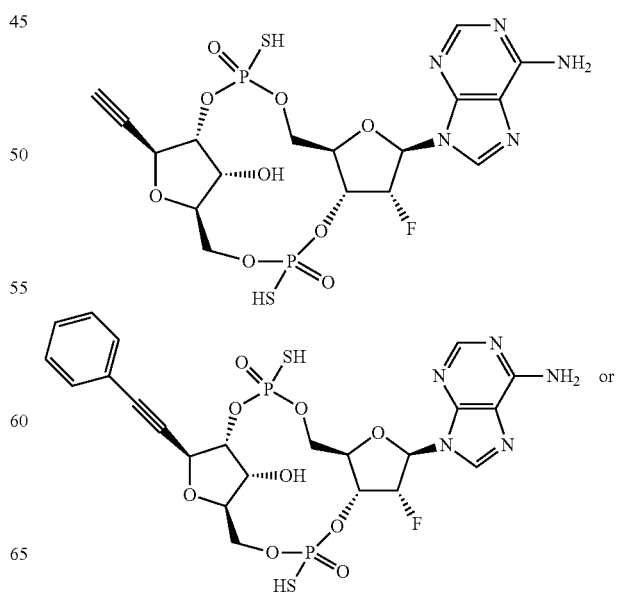

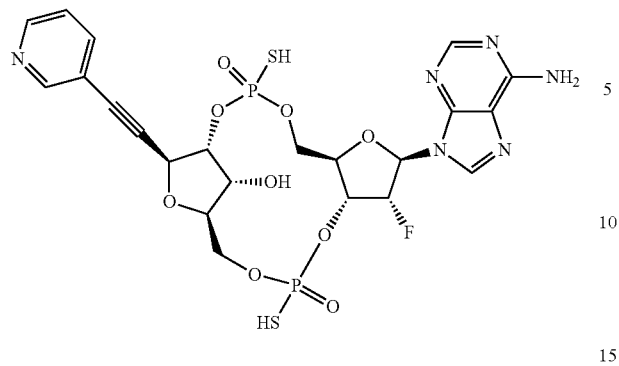

or a pharmaceutically acceptable salt, tautomer or stereoisomer thereof.

12. The compound according to claim 1 of the formula

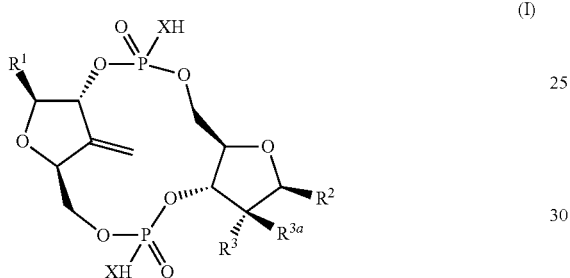

(I)

wherein
each X is independently O or S;
$R^1$ and $R^2$ are independently

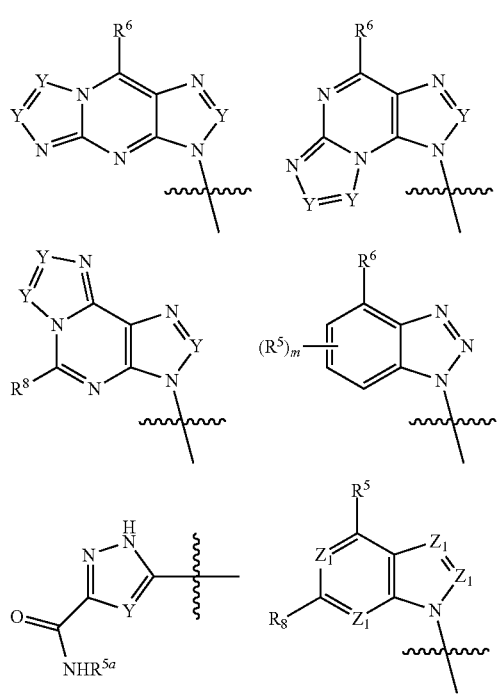

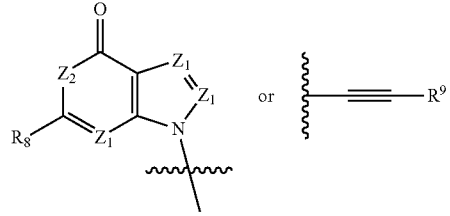

or 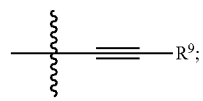

with the proviso that one of $R^1$ and $R^2$ must be $\underset{\xi}{\xi}\!\!-\!\!\equiv\!\!-R^9;$ $Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl substituted with 0-6 $R^5$;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;

Y is $CR^5$ or N;
m is 0, 1, 2 or 3;
or a pharmaceutically acceptable salt, tautomer or stereoisomer thereof.

13. The compound according to claim 1 of the formula

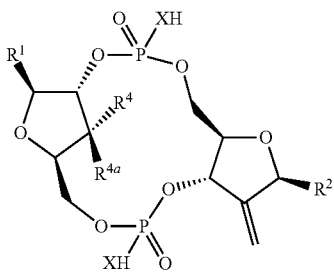

wherein
each X is independently O or S;
$R^1$ and $R^2$ are independently

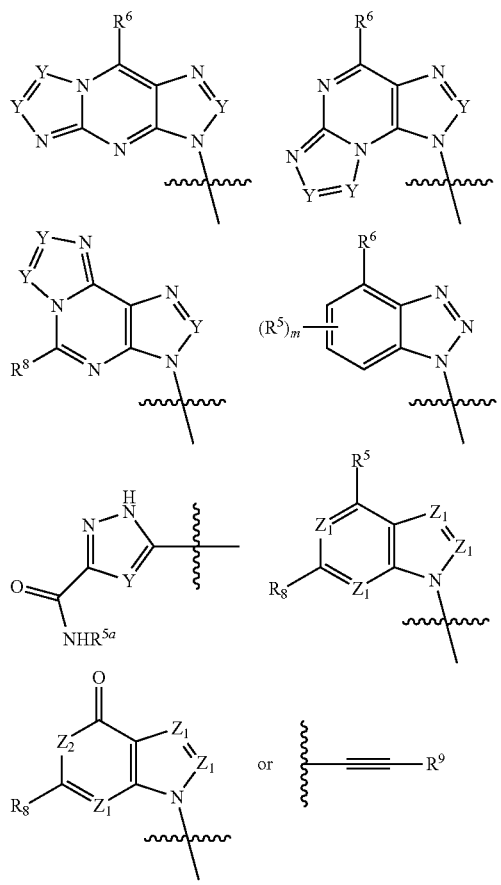

with the proviso that one of $R^1$ and $R^2$ must be

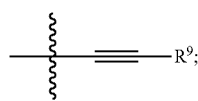

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl substituted with 0-6 $R^5$;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl substituted with 0-6 $R^a$, $C_{3-6}$ cycloalkyl substituted with 0-6 $R^a$, aryl substituted with 0-6 $R^a$ or heteroaryl substituted with 0-6 $R^a$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, $C_{1-6}$ alkyl substituted with 0-6 $R^5$, $C_{3-6}$ cycloalkyl substituted with 0-6 $R^5$, aryl substituted with 0-6 $R^5$ or heteroaryl substituted with 0-6 $R^5$;
Y is $CR^5$ or N;
m is 0, 1, 2 or 3;
or a pharmaceutically acceptable salt, tautomer or stereoisomer thereof.

14. The compound according to claim 1 which is (1R,6R,8R,9R,10R,15R,17S,18R)-8-(6-amino-9H-purin-9-yl)-17-ethynyl-9-fluoro-18-hydroxy-3,12-disulfanyl-2,4,7,11,13,16-hexaoxa-3$\lambda^5$,12$\lambda^5$-diphosphatricyclo[13.2.1.0$^{6,10}$]octadecane-3,12-dione,
(1R,6R,8R,9R,10R,15R,17S,18R)-8-(6-amino-9H-purin-9-yl)-9-fluoro-3,12,18-trihydroxy-17-(2-phenylethynyl)-2,4,7,11,13,16-hexaoxa-3$\lambda^5$,12$\lambda^5$-diphosphatricyclo[13.2.1.0$^{6,10}$]octadecane-3,12-dithione, or
(1R,6R,8R,9R,10R,15R,17S,18R)-8-(6-amino-9H-purin-9-yl)-9-fluoro-3,12,18-trihydroxy-17-[2-(pyridin-3-yl)ethynyl]-2,4,7,11,13,16-hexaoxa-3$\lambda^5$,12$\lambda^5$-diphosphatricyclo[13.2.1.0$^{6,10}$]octadecane-3,12-dithione
or a pharmaceutically acceptable salt or stereoisomer thereof.

15. A pharmaceutical composition comprising a compound according to claim 1 or a pharmaceutically acceptable salt thereof and one or more pharmaceutically acceptable carriers, diluents or excipients.

16. A method of treating diseases and conditions in which the modulation of STING is indicated in a subject which comprises administering a compound according to claim 1 or a pharmaceutically acceptable salt thereof.

17. A method of treating cancer comprising administering one or more compounds according to claim 1 or a pharmaceutically acceptable salt thereof.

18. The method of claim 17 wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers.

19. The method of claim 18 wherein the cancer is small cell lung cancer, non-small cell lung cancer, colorectal cancer, melanoma, renal cell carcinoma, head and neck cancer, Hodgkin's lymphoma or bladder cancer.

20. A method for treating cancer in a subject, comprising administering a compound, according to claim 1, or a pharmaceutically acceptable salt thereof, in combination with the administration of one or more immuno-oncology agents.

21. A method for treating a subject afflicted with cancer comprising administering to the subject:
   a) a compound according to claim 1, or a pharmaceutically acceptable salt thereof, and
   b) an anti-cancer agent which is an antibody or an antigen-binding portion thereof that binds specifically to a Programmed Death-1 (PD-1) receptor and inhibits PD-1 activity.

22. The method of claim 21, wherein the anti-PD-1 antibody is nivolumab or pembrolizumab.

23. The method of claim 22, wherein the anti-PD-1 antibody is nivolumab.

* * * * *